United States Patent
Kim et al.

(10) Patent No.: US 10,032,999 B2
(45) Date of Patent: Jul. 24, 2018

(54) COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

(71) Applicants: SAMSUNG SDI CO., LTD., Yongin-si, Gyeonggi-do (KR); SAMSUNG ELECTRONICS CO., LTD., Suwon-si, Gyeonggi-do (KR)

(72) Inventors: Byungku Kim, Suwon-si (KR); Dong Min Kang, Suwon-si (KR); Changwoo Kim, Suwon-si (KR); Jaejin Oh, Suwon-si (KR); Eun Sun Yu, Suwon-si (KR); Yuna Jang, Suwon-si (KR); Sung-Hyun Jung, Suwon-si (KR); Jinseok Hong, Suwon-si (KR)

(73) Assignees: Samsung SDI Co., Ltd., Yongin-si, Gyeonggi-do (KR); Samsung Electronics Co., Ltd., Suwon-Si, Gyeonggi-do (KR)

( * ) Notice: Subject to any disclaimer, the term of this patent is extended or adjusted under 35 U.S.C. 154(b) by 0 days.

(21) Appl. No.: 15/678,397

(22) Filed: Aug. 16, 2017

(65) Prior Publication Data
US 2018/0090690 A1    Mar. 29, 2018

(30) Foreign Application Priority Data
Sep. 29, 2016  (KR) .......................... 10-2016-0125668

(51) Int. Cl.
*C07D 487/04* (2006.01)
*H01L 51/00* (2006.01)
*C09K 11/02* (2006.01)
*C09K 11/06* (2006.01)
*C07D 519/00* (2006.01)
*H01L 51/50* (2006.01)

(52) U.S. Cl.
CPC ........ *H01L 51/0072* (2013.01); *C07D 487/04* (2013.01); *C07D 519/00* (2013.01); *C09K 11/025* (2013.01); *C09K 11/06* (2013.01); *H01L 51/0052* (2013.01); *H01L 51/0054* (2013.01); *H01L 51/0067* (2013.01); *H01L 51/0073* (2013.01); *H01L 51/0074* (2013.01); *H01L 51/0085* (2013.01); *C09K 2211/1007* (2013.01); *C09K 2211/1029* (2013.01); *C09K 2211/185* (2013.01); *H01L 51/5016* (2013.01); *H01L 51/5056* (2013.01); *H01L 51/5072* (2013.01)

(58) Field of Classification Search
CPC .................................................. C07D 487/04
See application file for complete search history.

(56) References Cited

FOREIGN PATENT DOCUMENTS

| KR | 10-2012-0072784 A | 7/2012 |
|---|---|---|
| KR | 10-1196093 B1 | 11/2012 |
| KR | 10-1219492 B1 | 1/2013 |
| KR | 10-2013-0050237 A | 5/2013 |
| KR | 10-2013-0057397 A | 5/2013 |
| KR | 10-1456521 B1 | 10/2014 |
| KR | 10-1470055 B1 | 12/2014 |

*Primary Examiner* — Shawquia Jackson
(74) *Attorney, Agent, or Firm* — Lee & Morse, P.C.

(57) ABSTRACT

Disclosed are a compound for an organic optoelectric device represented by Chemical Formula 1, a composition for an organic optoelectric device, an organic optoelectric device including the same, and a display device. Details of Chemical Formula 1 are the same as those defined in the specification.

21 Claims, 1 Drawing Sheet

COMPOUND FOR ORGANIC OPTOELECTRIC DEVICE, COMPOSITION FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0125668 filed in the Korean Intellectual Property Office on Sep. 29, 2016, the entire contents of which are incorporated herein by reference.

BACKGROUND OF THE INVENTION

1. Field of the Invention

A compound for an organic optoelectric device, a composition for an organic optoelectric device, an organic optoelectric device, and a display device are disclosed.

2. Description of the Related Art

An organic optoelectric device (organic optoelectric diode) is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

The organic optoelectric device may for example include an organic photoelectric device, an organic light emitting diode, an organic solar cell, an organic photo conductor drum, and the like.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides a composition for an organic optoelectric device including the compound for an organic optoelectric device.

Yet another embodiment provides an organic optoelectric device including the compound.

Still another embodiment provides a display device including the organic optoelectric device.

According to an embodiment, a compound for an organic optoelectric device represented by Chemical Formula 1 is provided.

[Chemical Formula 1]

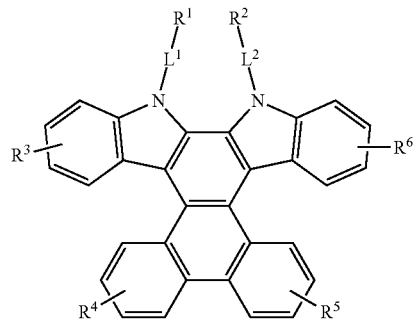

In Chemical Formula 1, $R^1$ and $R^2$ are independently a substituted or unsubstituted C6 to C30 aryl group, a substituted or unsubstituted C2 to C30 heterocyclic group, or a combination thereof, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, $L^1$ and $L^2$ are independently a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

According to another embodiment, a composition for an organic optoelectric device includes a first compound for an organic optoelectric device represented by Chemical Formula 1A; and a second compound for an organic optoelectric device represented by Chemical Formula 1B.

[Chemical Formula 1A]

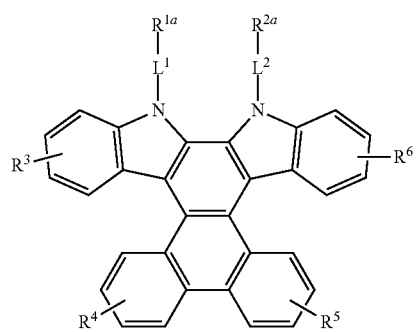

-continued

[Chemical Formula 1B]

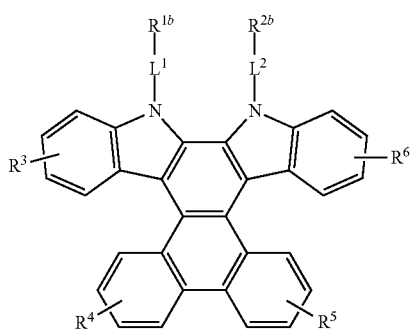

In Chemical Formula 1A and Chemical Formula 1B, $R^{1a}$ and $R^{2a}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, a substituted or unsubstituted benzonaphthothiophenyl group, or a substituted or unsubstituted benzoquinazolinyl group, at least one of $R^{1a}$ and $R^{2a}$ is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, or a substituted or unsubstituted benzoquinazolinyl group, $R^{1b}$ and $R^{2b}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

According to another embodiment, a composition for an organic optoelectric device includes the first compound for an organic optoelectric device; and at least one second compound for an organic optoelectric device selected from a compound represented by Chemical Formula 2 and a compound consisting of a combination of a moiety represented by Chemical Formula 3 and a moiety represented by Chemical Formula 4.

[Chemical Formula 2]

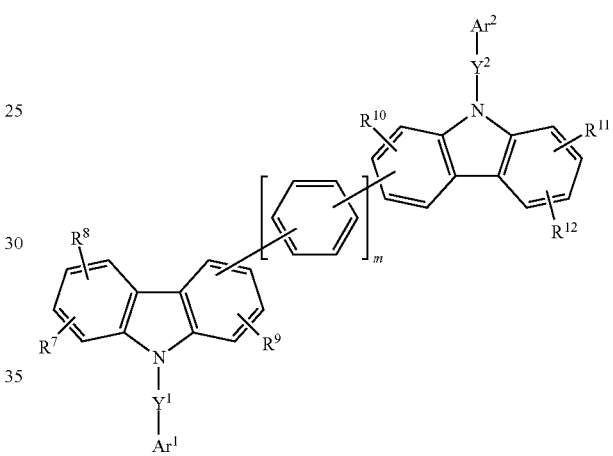

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^7$ to $R^{12}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2;

[Chemical Formula 3]

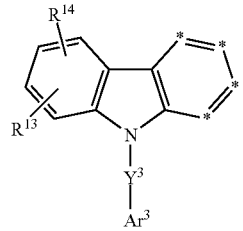

-continued

[Chemical Formula 4]

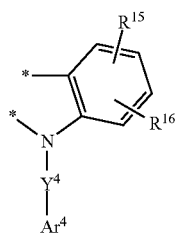

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{13}$ to $R^{16}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 are bound to two adjacent *'s of Chemical Formula 4 to provide a fused ring and *'s of not providing the fused ring in Chemical Formula 3 are independently $CR^a$, and $R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

According to another embodiment, an organic optoelectric device includes an anode and a cathode facing each other and at least one organic layer disposed between the anode and the cathode, wherein the organic layer includes the compound for an organic optoelectric device or the composition for an organic optoelectric device.

According to another embodiment, a display device includes the organic optoelectric device.

An organic optoelectric device having high efficiency and a long life-span may be realized.

DETAILED DESCRIPTION

Figure 1:
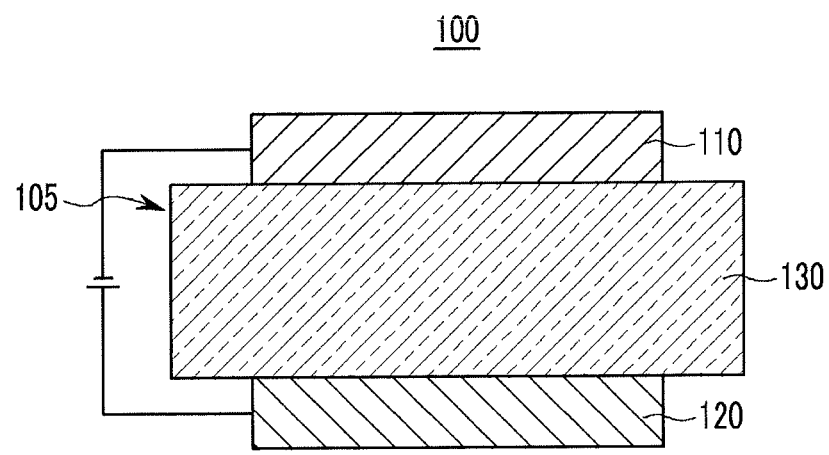
FIGS. 1 and 2 are cross-sectional views showing organic light emitting diodes according to embodiments.

Hereinafter, embodiments of the present disclosure are described in detail. However, these embodiments are exemplary, the present disclosure is not limited thereto and the present disclosure is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group, or a cyano group.

In one example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C6 to C30 heteroaryl group. In addition, in specific examples of the present disclosure, the "substituted" refers to replacement of at least one hydrogen of a substituent or a compound by deuterium, a C1 to C30 alkyl group, a C6 to C18 aryl group, or a C6 to C20 heteroaryl group. In addition, in more specific examples of the present disclosure, the "substituted" refers to replacement of at least one hydrogen of a substituent or a compound by deuterium, a C1 to C4 alkyl group, a C6 to C18 aryl group, or a C2 to C18 heteroaryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted fluoranthenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, a substituted or unsubstituted benzonaphthothiophenyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

As used herein, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectric device according to an embodiment is described.

A compound for an organic optoelectric device according to an embodiment is represented by Chemical Formula 1.

[Chemical Formula 1]

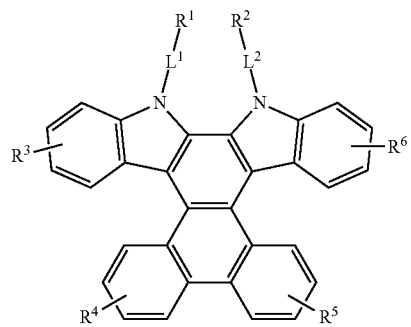

In Chemical Formula 1, $R^1$ and $R^2$ are independently a substituted or unsubstituted C6 to C30 aryl group, a substituted or unsubstituted C2 to C30 heterocyclic group, or a combination thereof, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, $L^1$ and $L^2$ are independently a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

A compound for an organic optoelectric device according to an embodiment has a structure that phenanthrene is fused with indolocarbazole and thus may show device performance of a low driving voltage and high efficiency since excellent hole characteristics of the indolocarbazole are not only used, but holes are also transferred much faster due to the additionally fused moiety.

In particular, when triphenylene is introduced, HOMO energy of the compound becomes further shallow, the holes are transferred into a dopant without a trap, and thus a fast driving voltage may be secured.

In an example embodiment, $R^1$ and $R^2$ of Chemical Formula 1 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, a substituted or unsubstituted benzonaphthothiophenyl group, or a substituted or unsubstituted benzoquinazolinyl group.

In a specific example embodiment, Chemical Formula 1 may be represented by Chemical Formula 1A or Chemical Formula 1B according to characteristics of $R^1$ and $R^2$ of Chemical Formula 1 and each of Chemical Formula 1A and Chemical Formula 1B may be defined as follows.

[Chemical Formula 1A]

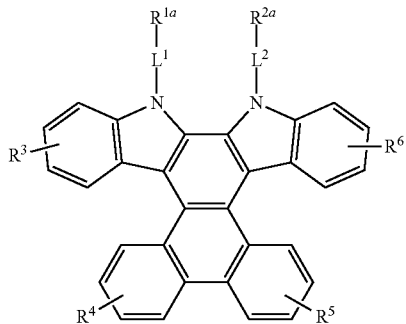

In Chemical Formula 1A, $R^{1a}$ and $R^{2a}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, a substituted or unsubstituted benzonaphthothiophenyl group, or a substituted or unsubstituted benzoquinazolinyl group, at least one of $R^{1a}$ and $R^{2a}$ is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, or a substituted or unsubstituted benzoquinazolinyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

[Chemical Formula 1B]

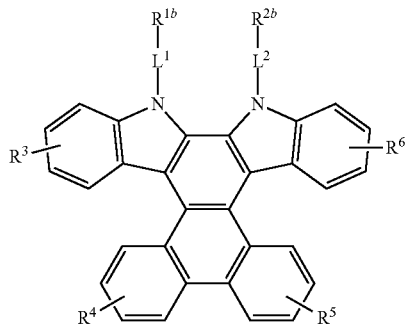

In Chemical Formula 1B, $R^{1b}$ and $R^{2b}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

For example, $R^1$ and $R^2$ may independently be selected from substituents of Group I.

[Group I]

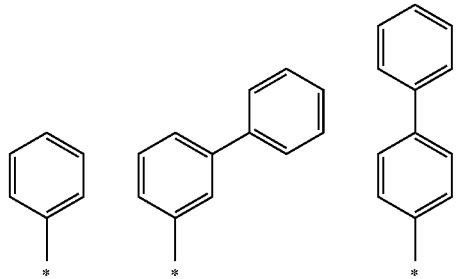

-continued
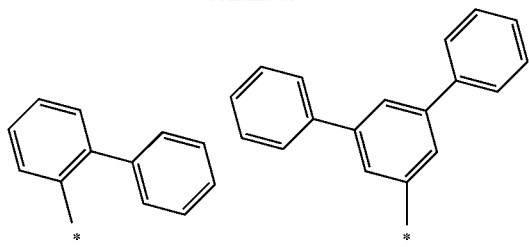
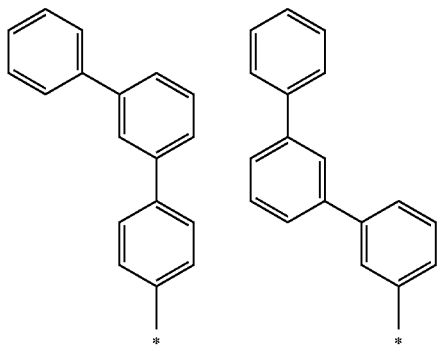
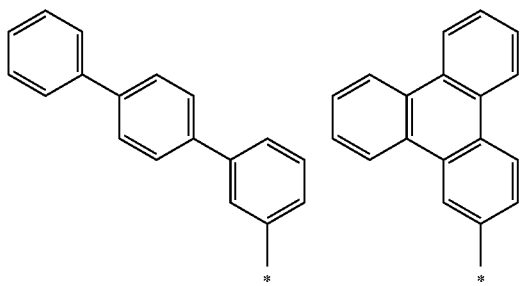
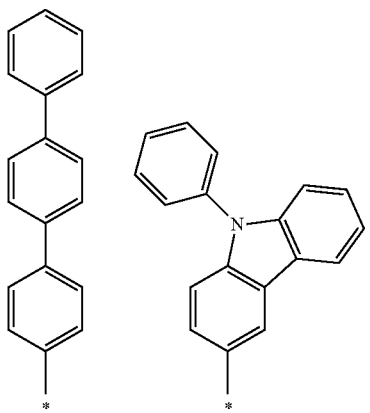
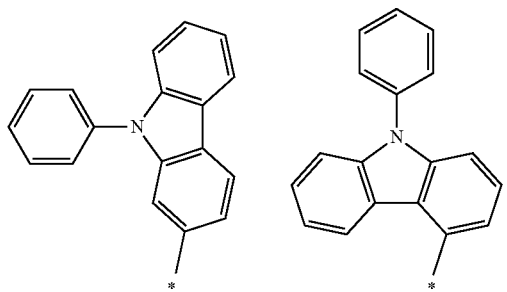
-continued
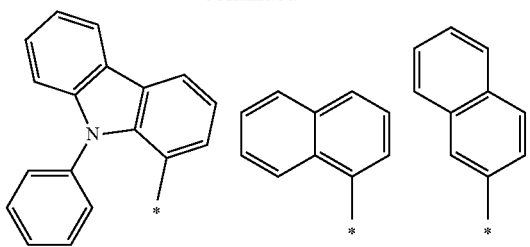
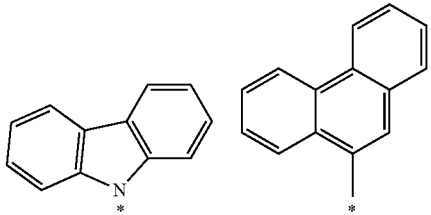
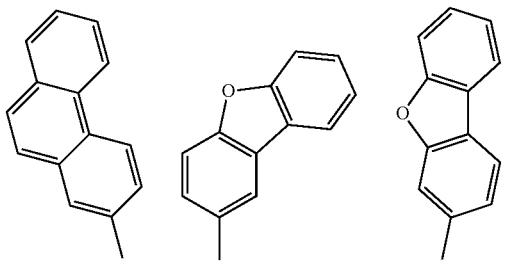
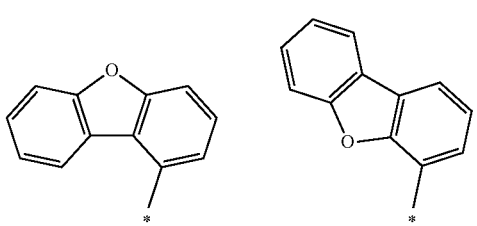
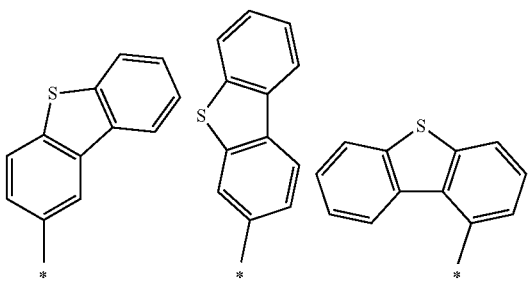
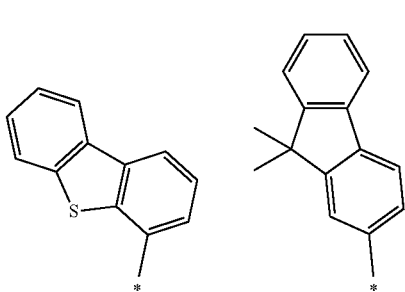

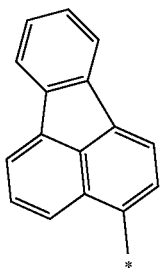 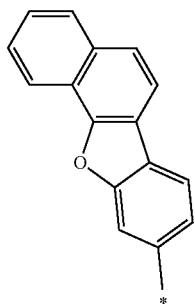 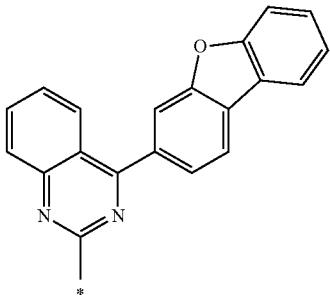
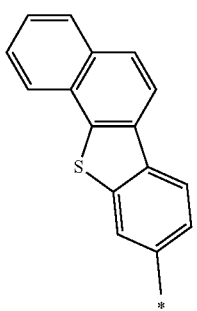 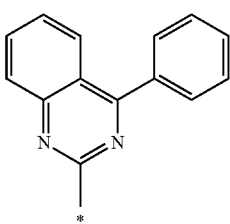 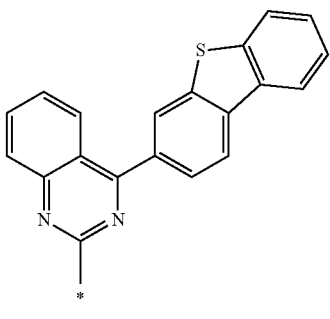
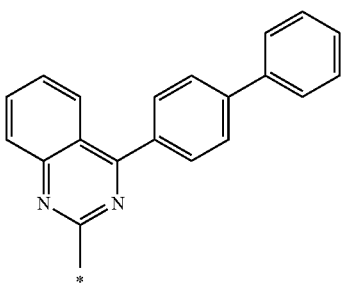 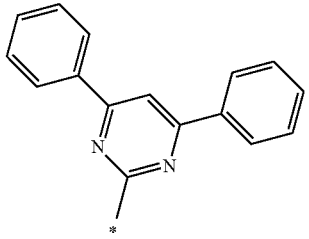
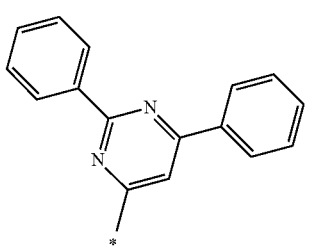
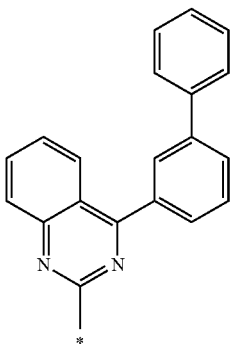 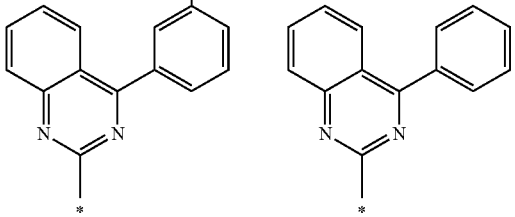 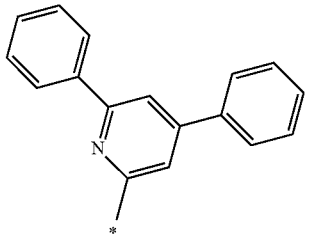
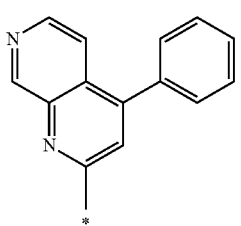 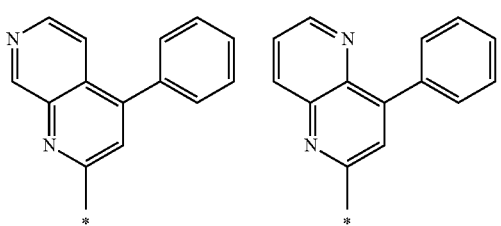 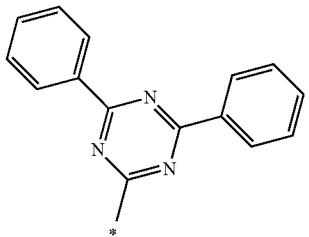

-continued

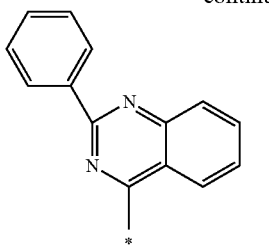
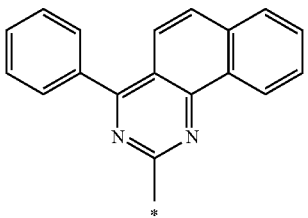
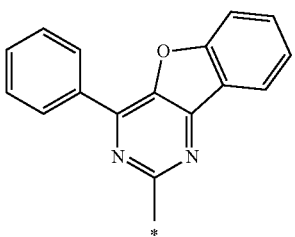
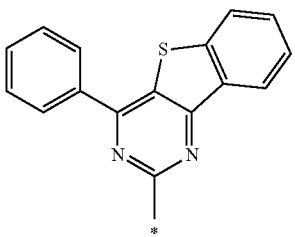
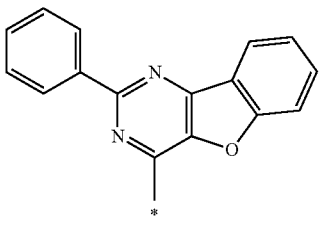
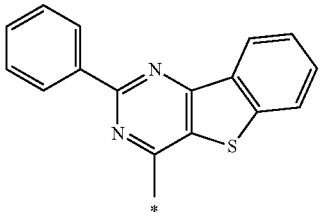
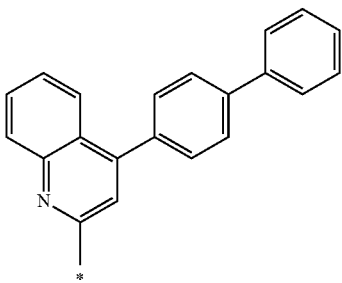

-continued

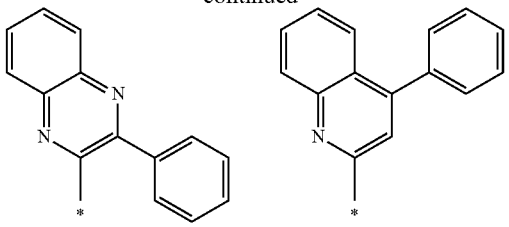

In Group I, * is a binding site with an adjacent atom.

In a specific example embodiment, $R^1$ and $R^2$ of Chemical Formula 1 may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group.

In addition, in an example embodiment, $L^1$ and $L^2$ of Chemical Formula 1 may independently be a single bond, a substituted or unsubstituted phenylene group, a substituted or unsubstituted biphenylene group, or a substituted or unsubstituted terphenylene group, or may be for example selected from a single bond or a substituted or unsubstituted linking groups of Group II.

[Group II]

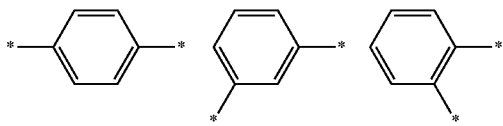
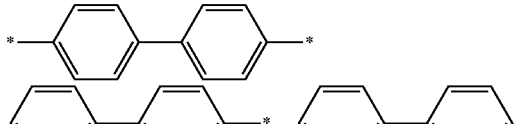

In Group II, * is a binding site with an adjacent atom.

In an example embodiment, $R^3$ to $R^6$ of Chemical Formula 1 may independently be hydrogen, deuterium, a substituted or unsubstituted C1 to C10 alkyl group, a substituted or unsubstituted C6 to C20 aryl group, and specifically hydrogen, deuterium, a substituted or unsubstituted C1 to C4 alkyl group, or a substituted or unsubstituted C6 to C12 aryl group and for example each of $R^3$ to $R^6$ may be hydrogen.

In a most specific example embodiment, $R^1$ and $R^2$ may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted quinazolinyl group, or a substituted or unsubstituted benzofuranpyrimidinyl group, or a substituted or unsubstituted benzothiophenepyrimidinyl group, $L^1$ and $L^2$ may independently be a single bond, or phenylene group, $R^3$ to $R^6$ are all hydrogen, and the "substituted" refers to replacement of at least one hydrogen by deuterium, a C1 to C4 alkyl group, a phenyl group, a biphenyl group, a dibenzofuranyl group, or a dibenzothiophenyl group.

The compound for an organic optoelectric device represented by Chemical Formula 1 may be for example selected from compounds of Group 1, but is not limited thereto.

[Group 1]

1

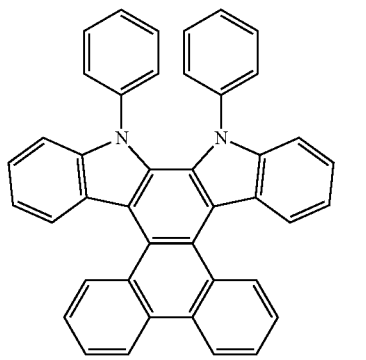

2

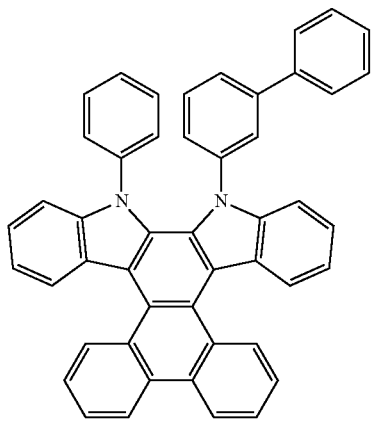

3

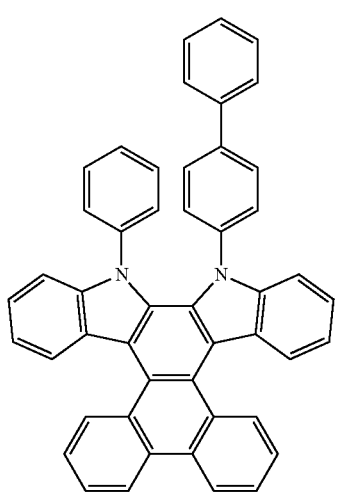

-continued

4

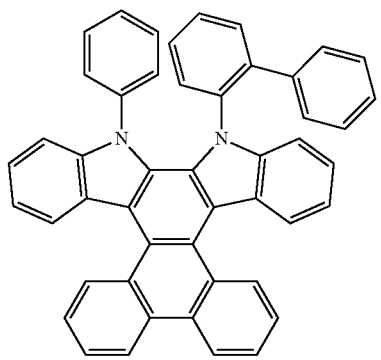

5

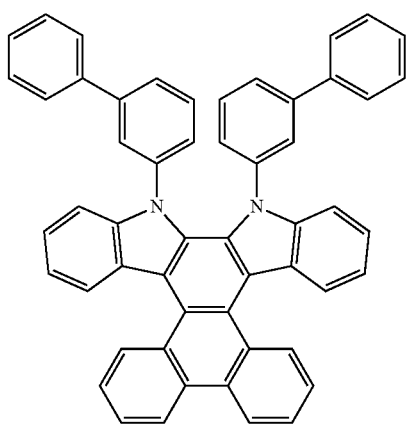

6

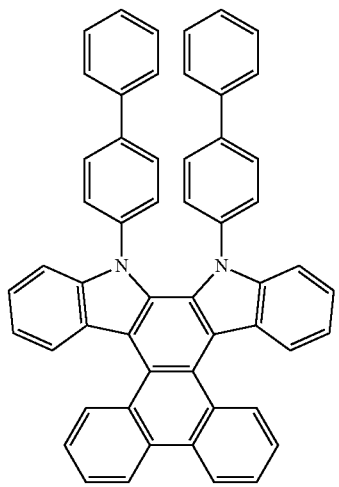

7

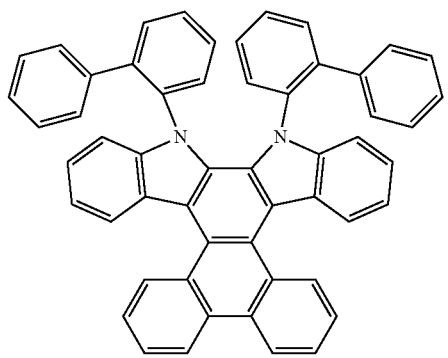

8
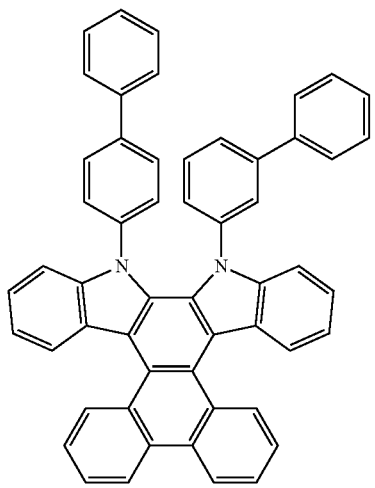
9
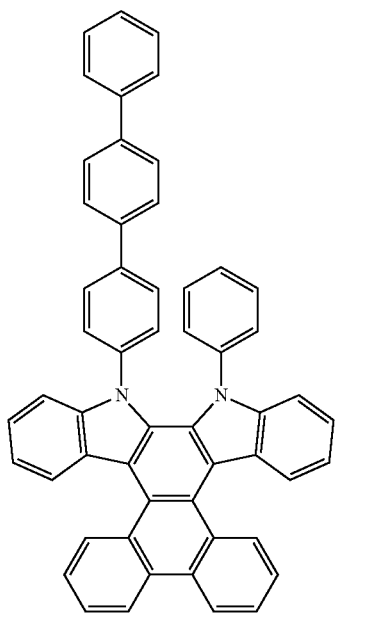
10
11
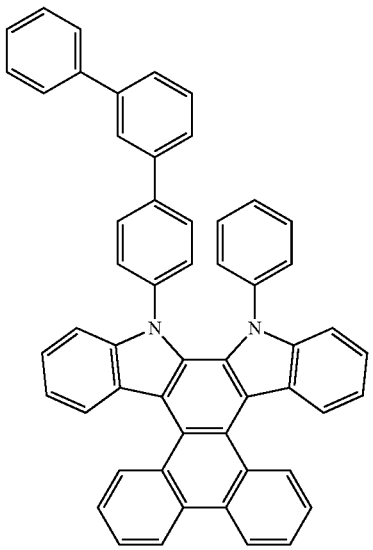
12
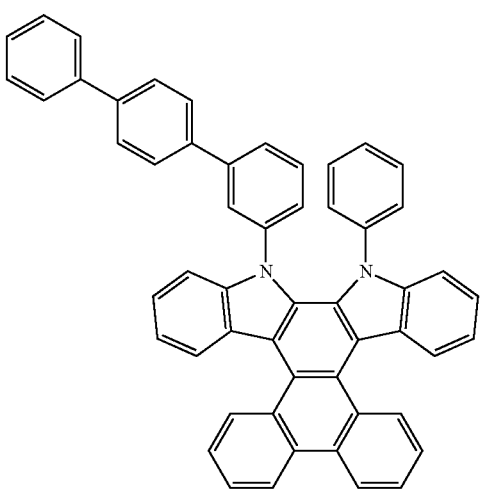
13
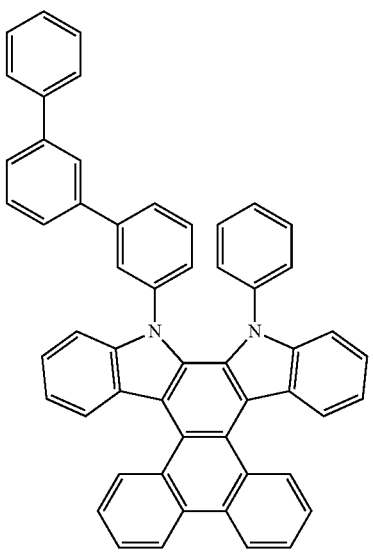

14
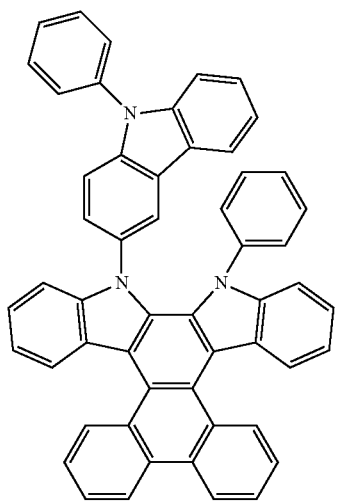
15
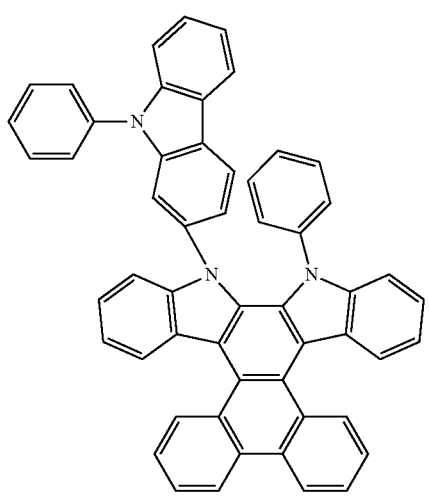
16
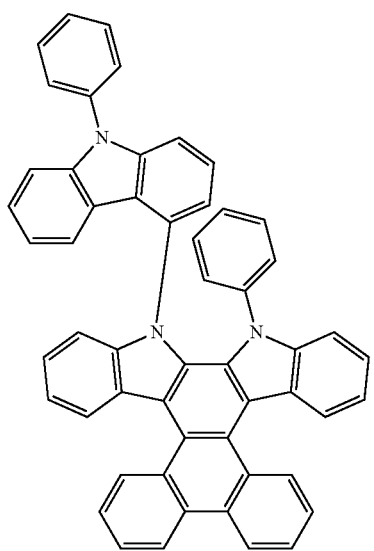
17
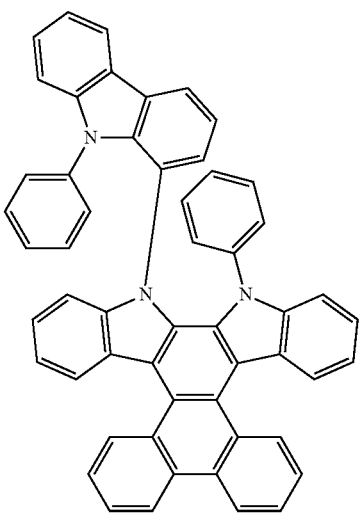
18
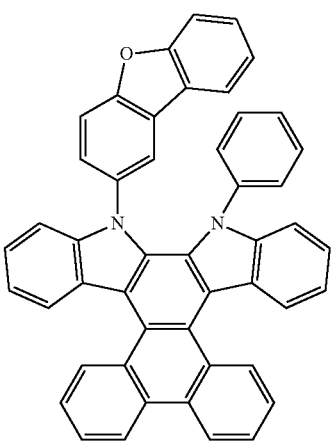
19
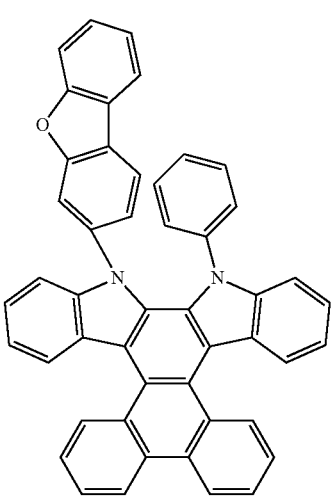

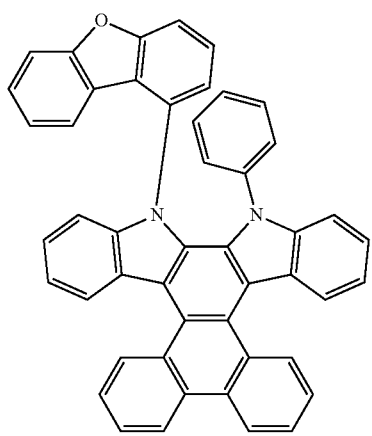
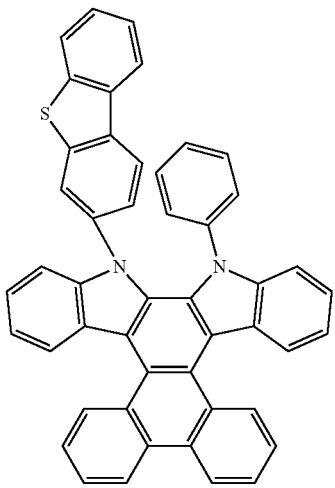
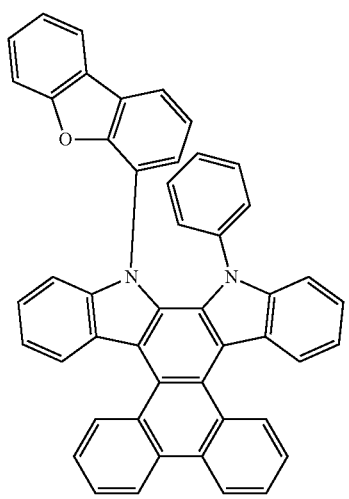
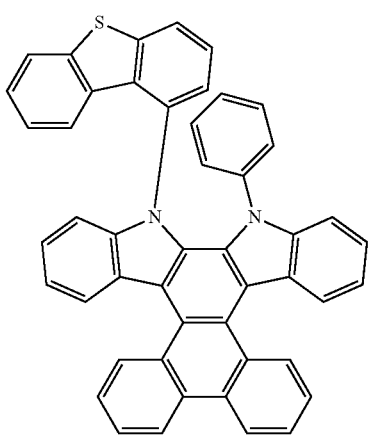
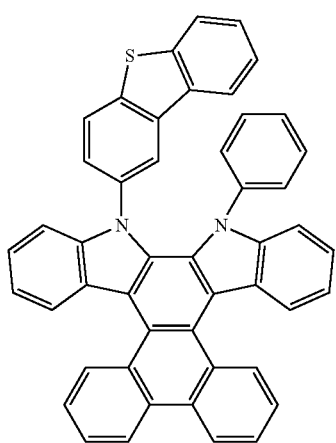
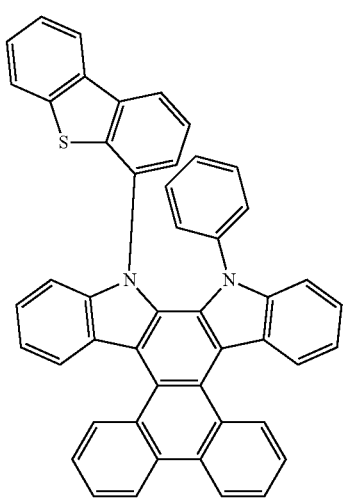

25
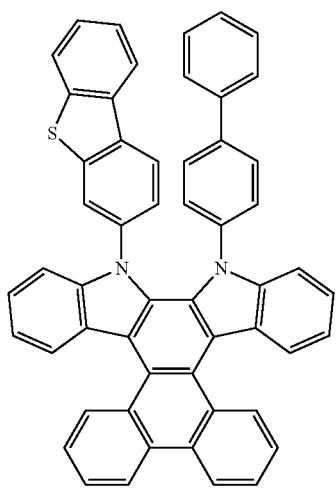
26
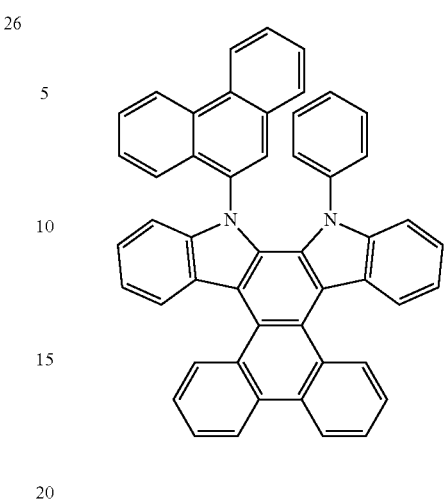
27
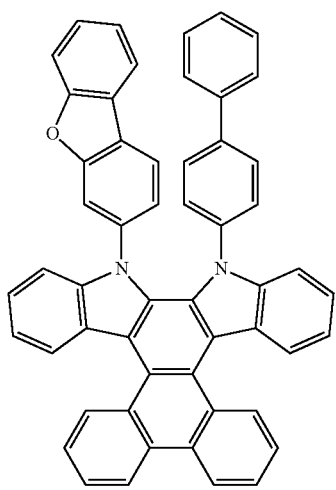
29
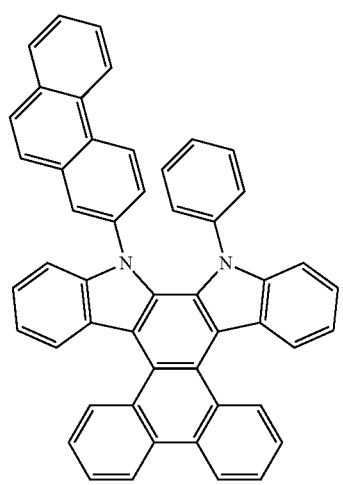
28
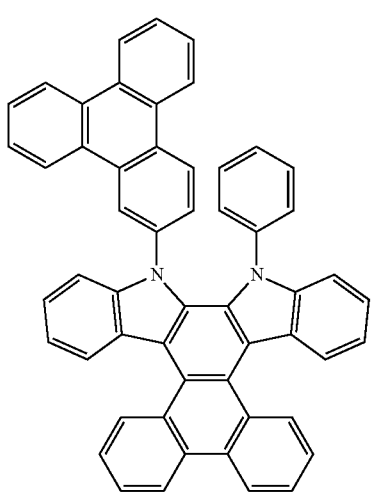
31
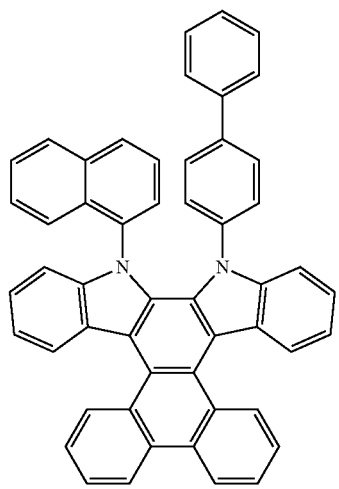

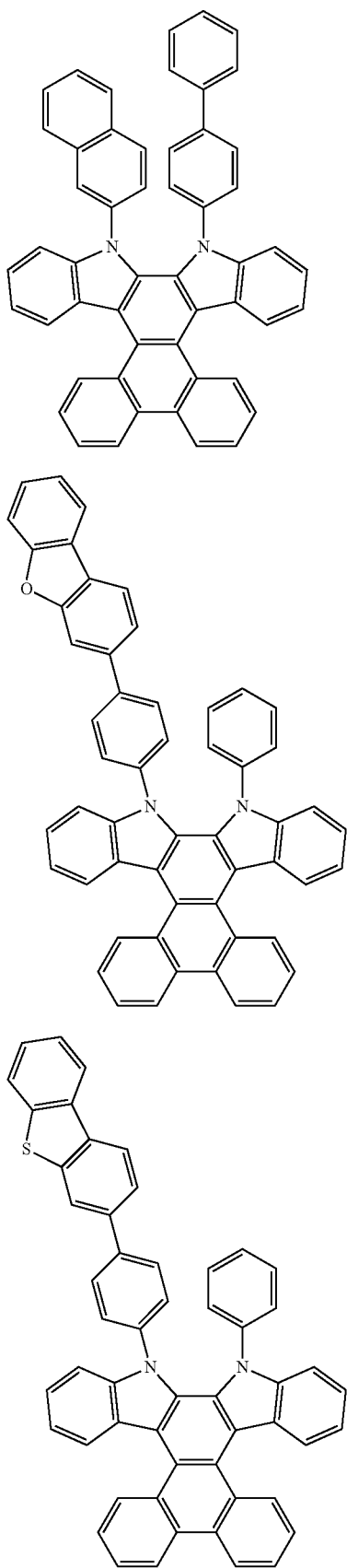
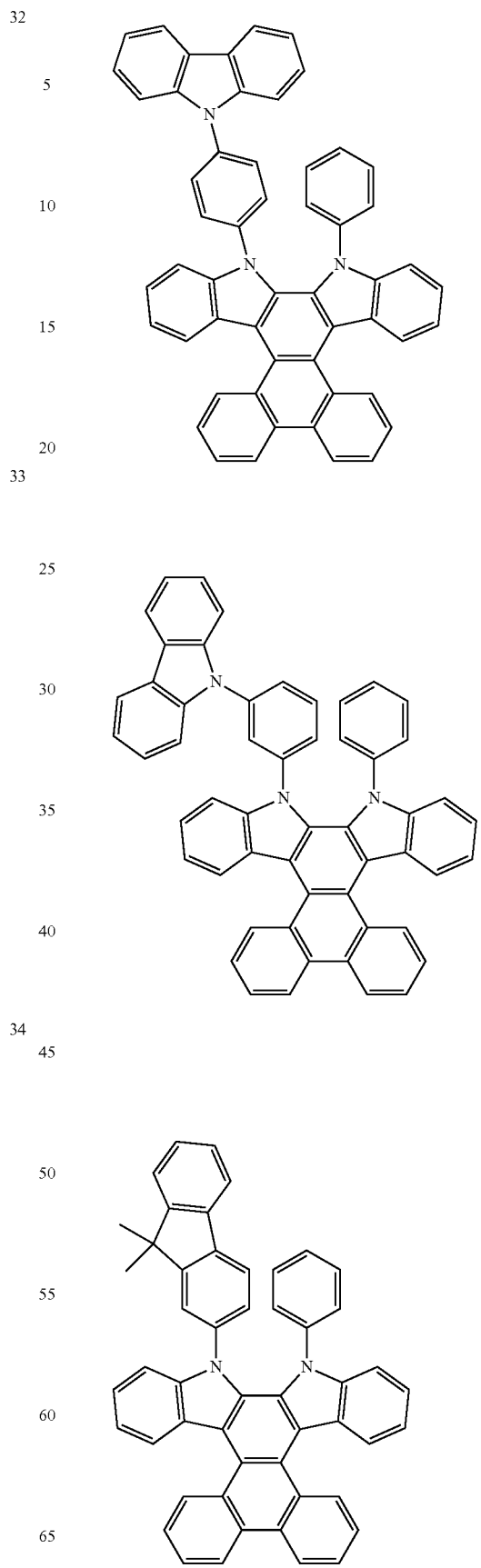

38
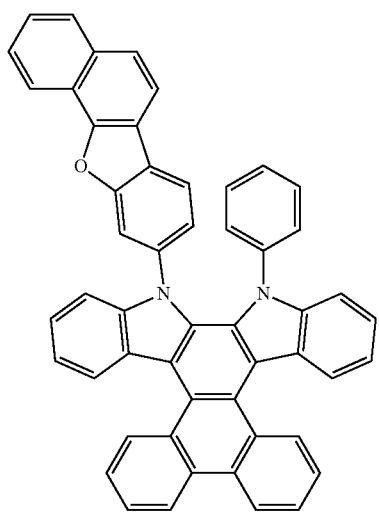
39
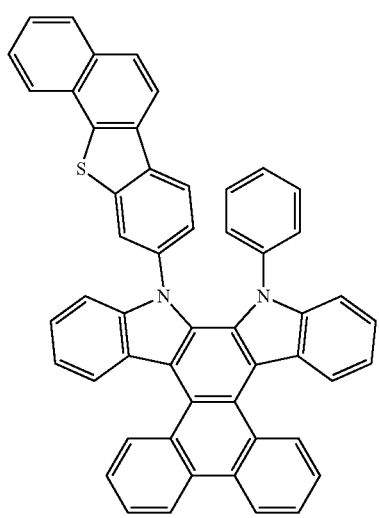
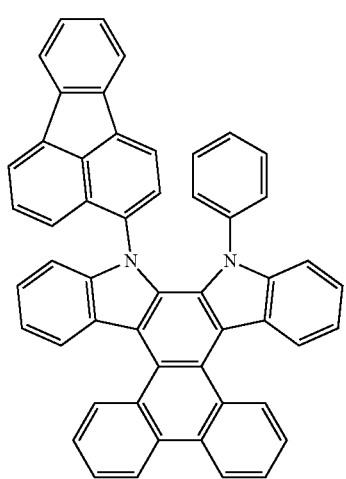
41
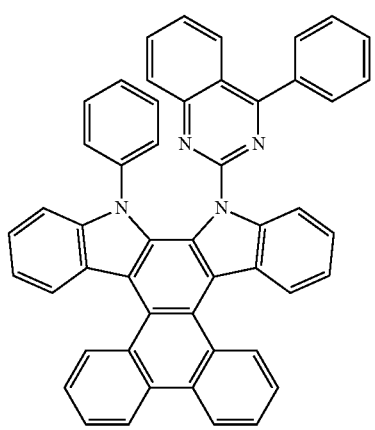
42
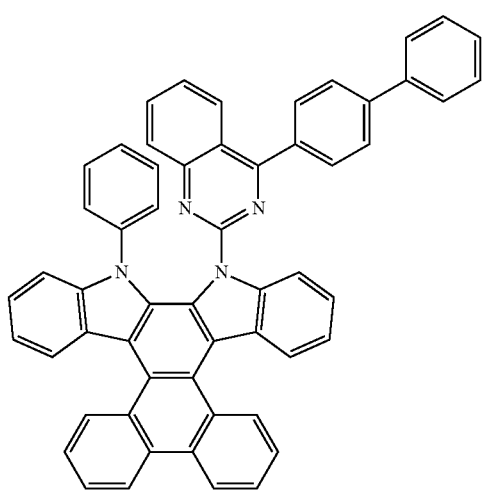
43
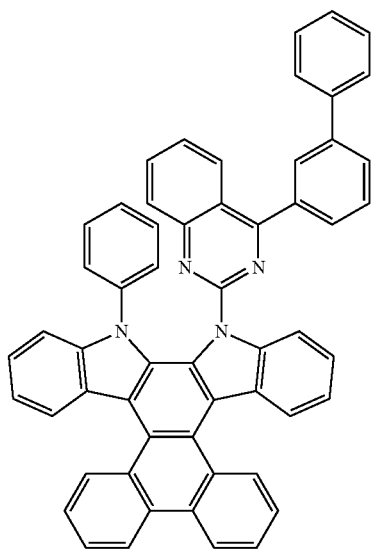

-continued
43
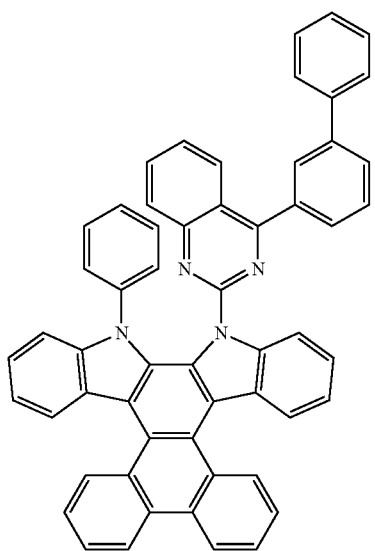
44
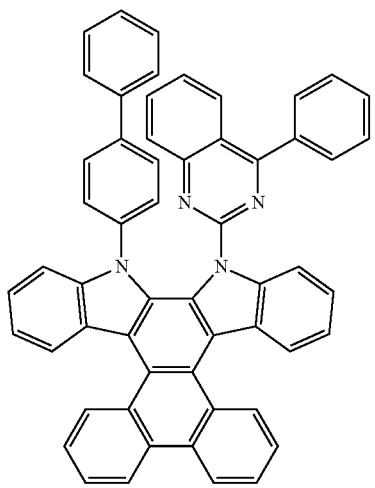
45
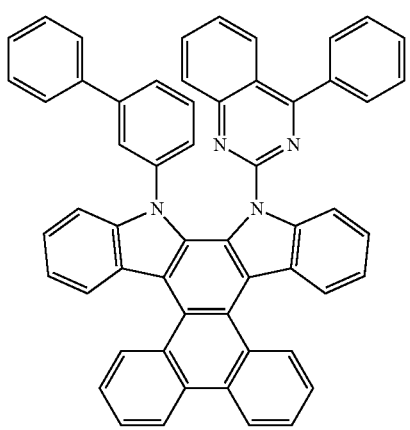
-continued
46
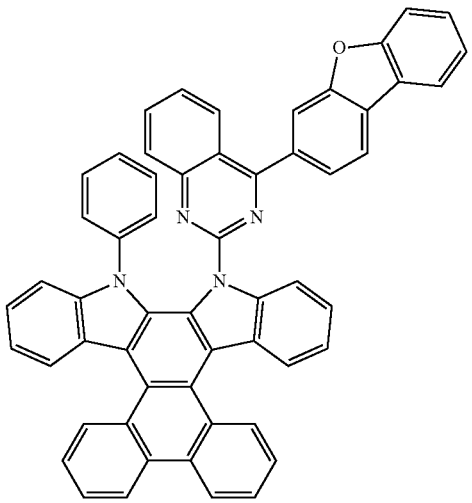
47
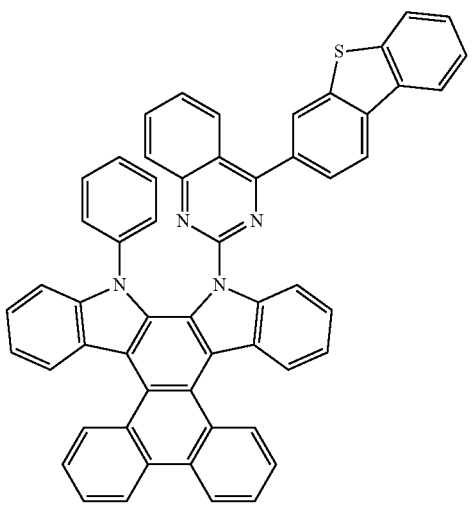
48
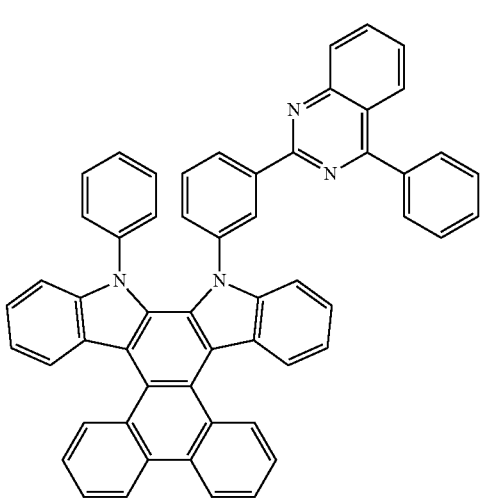

49
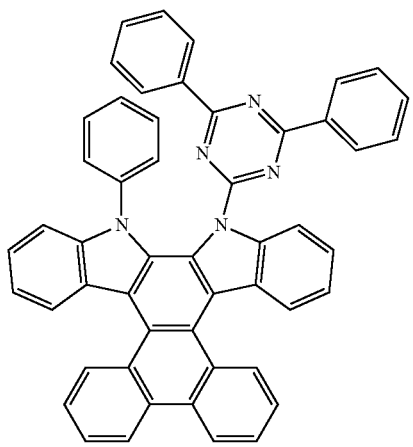
50
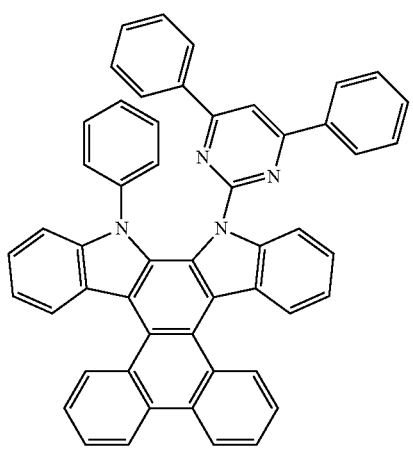
51
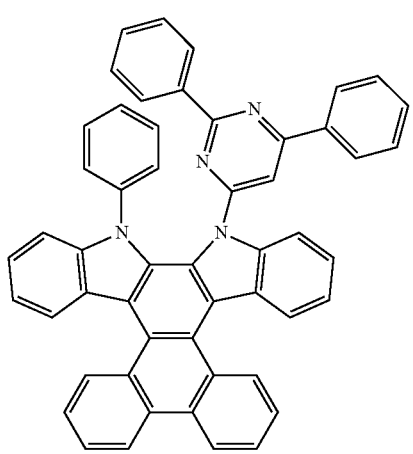
52
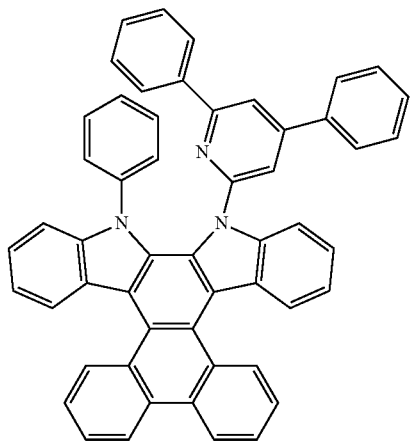
53
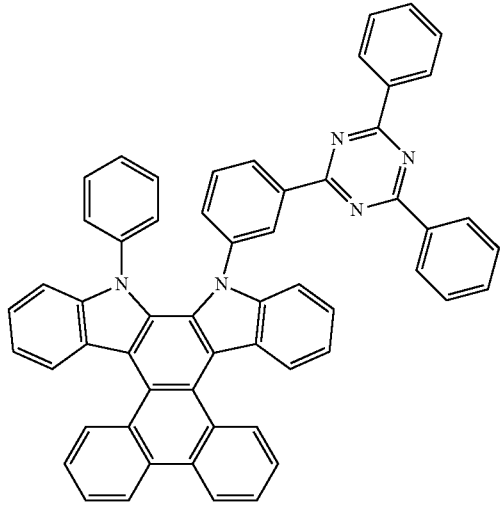
54
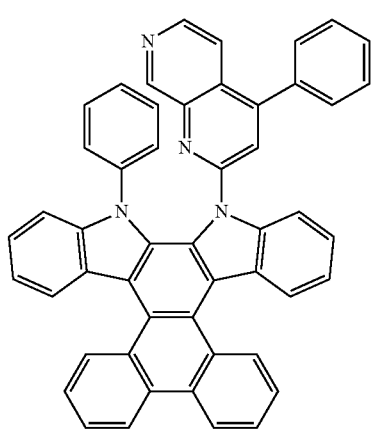

35
-continued
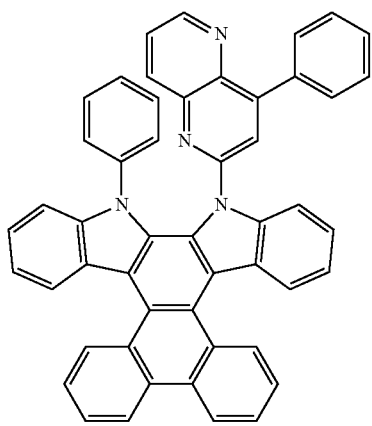
56
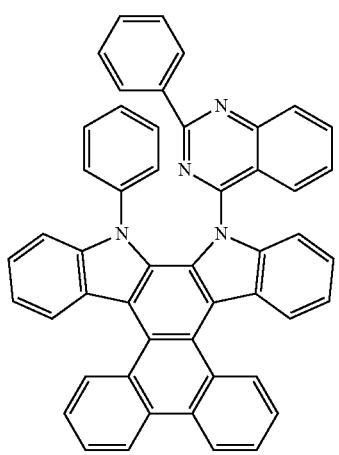
57
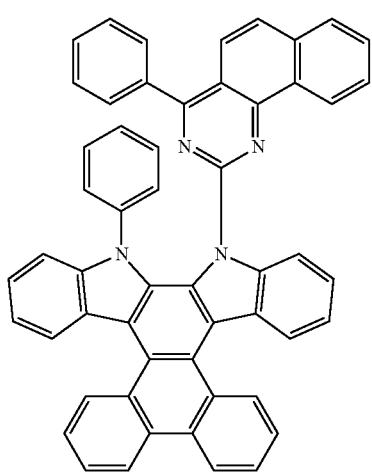
36
-continued
58
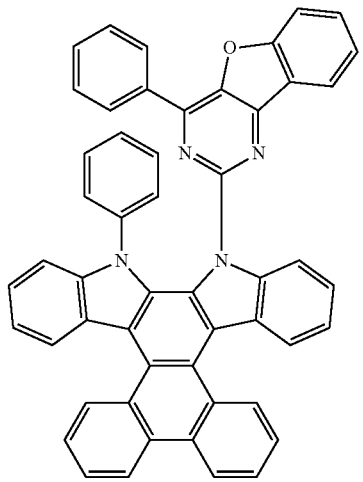
59
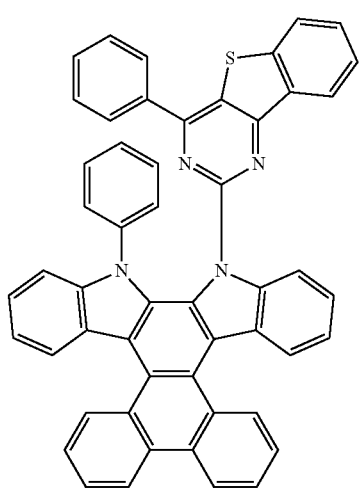
60
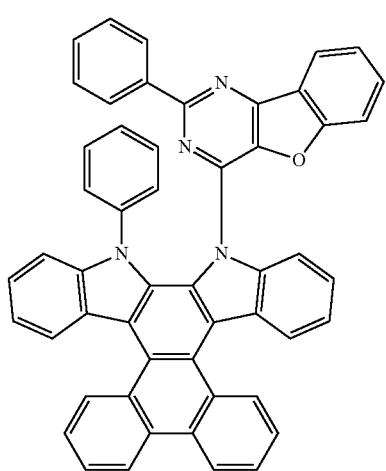

61

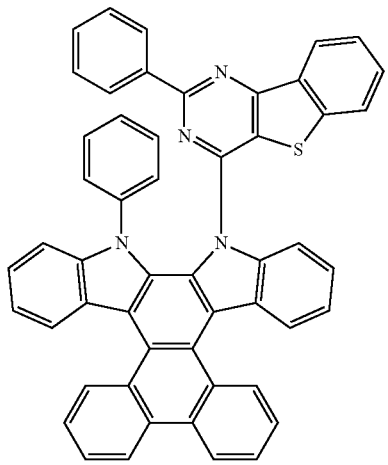

62

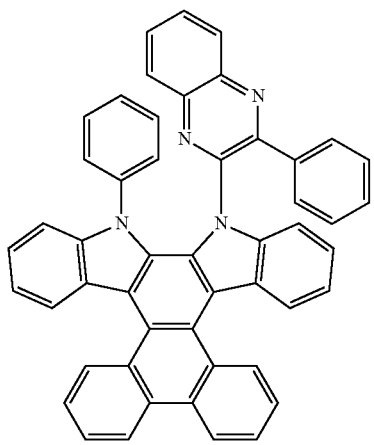

63

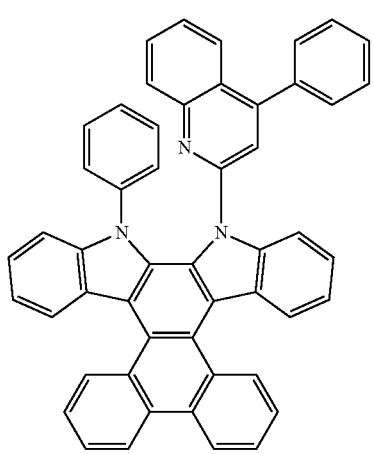

64

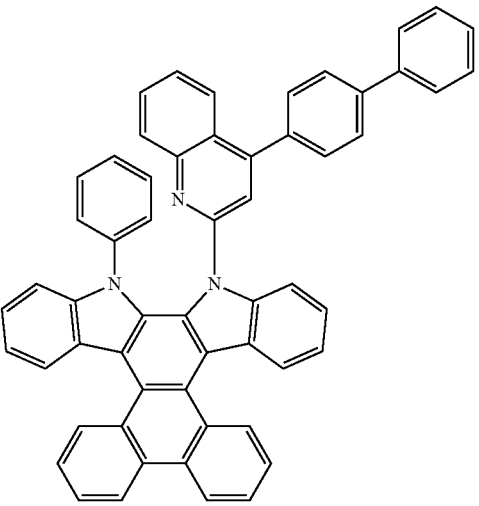

The compound for an organic optoelectric device may be applied to an organic optoelectric device and may be applied to an organic optoelectric device in a form of a compound for an organic optoelectric device or a composition for an organic optoelectric device.

Hereinafter, one example of a composition for an organic optoelectric device including the compound for an organic optoelectric device is described.

A composition for an organic optoelectric device according to another embodiment includes a compound represented by Chemical Formula 1A as a first compound for an organic optoelectric device and a compound represented by Chemical Formula 1B as a second compound for an organic optoelectric device.

In an example embodiment, $R^{1a}$ and $R^{2a}$ of Chemical Formula 1A may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, at least one of $R^{1a}$ and $R^{2a}$ may be a substituted or unsubstituted pyrimidinyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, and $R^{1b}$ and $R^{2b}$ of Chemical Formula 1B may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, or a substituted or unsubstituted dibenzothiophenyl group.

In Chemical Formula 1A and Chemical Formula 1B, definitions of $R^3$ to $R^6$, $L^1$, $L^2$, and "substituted" are the same as in Chemical Formula 1.

A composition for an organic optoelectric device according to yet another embodiment includes the first compound for an organic optoelectric device; and at least one second compound for an organic optoelectric device selected from a compound represented by Chemical Formula 2 and a compound consisting of a combination of a moiety represented by Chemical Formula 3 and a moiety represented by Chemical Formula 4.

[Chemical Formula 2]

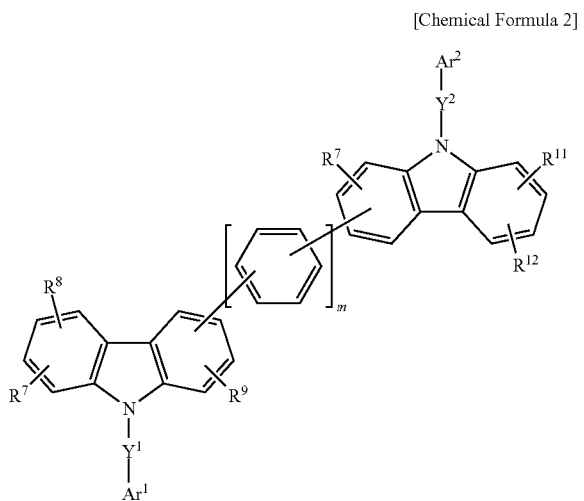

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^2$ are independently a substituted or unsubstituted C6 to C30 aryl group, a substituted or unsubstituted C2 to C30 heterocyclic group, or a combination thereof, $R^7$ to $R^{12}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2;

[Chemical Formula 3]

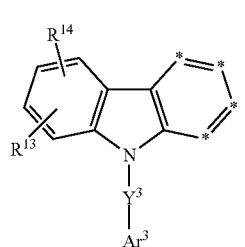

[Chemical Formula 4]

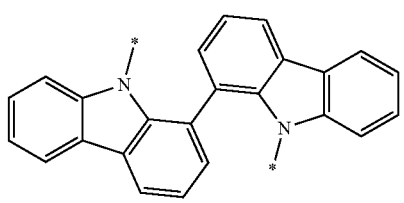

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{13}$ to $R^{16}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 are bound to two adjacent *'s of Chemical Formula 4 to provide a fused ring and *'s of not providing the fused ring in Chemical Formula 3 are independently $CR^a$, and $R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

In an example embodiment, $Y^1$ and $Y^2$ of Chemical Formula 2 may independently be a single bond, or a substituted or unsubstituted C6 to C18 arylene group.

In an example embodiment, $Ar^1$ and $Ar^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

In an example embodiment, $R^7$ to $R^{12}$ of Chemical Formula 2 may independently be hydrogen, deuterium, or a substituted or unsubstituted C6 to C12 aryl group.

In an example embodiment, m of Chemical Formula 2 may be 0 or 1.

In a specific example embodiment, Chemical Formula 2 may be one of structures of Group III and *—$Y^1$—$Ar^1$ and *—$Y^2$—$Ar^2$ may be one of substituents of Group IV.

[Group III]

C-1

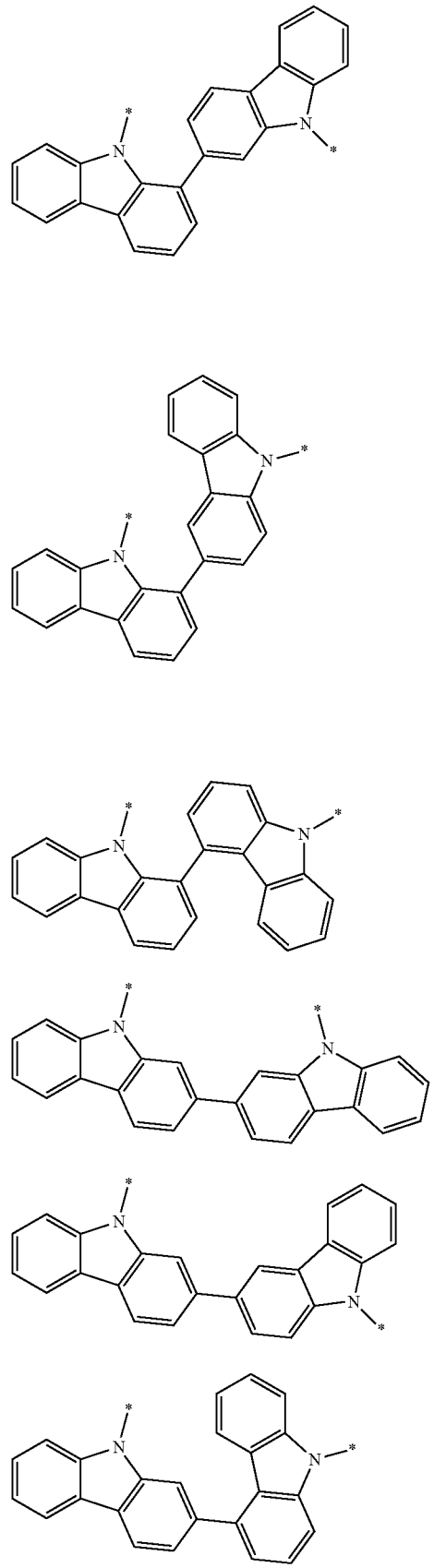
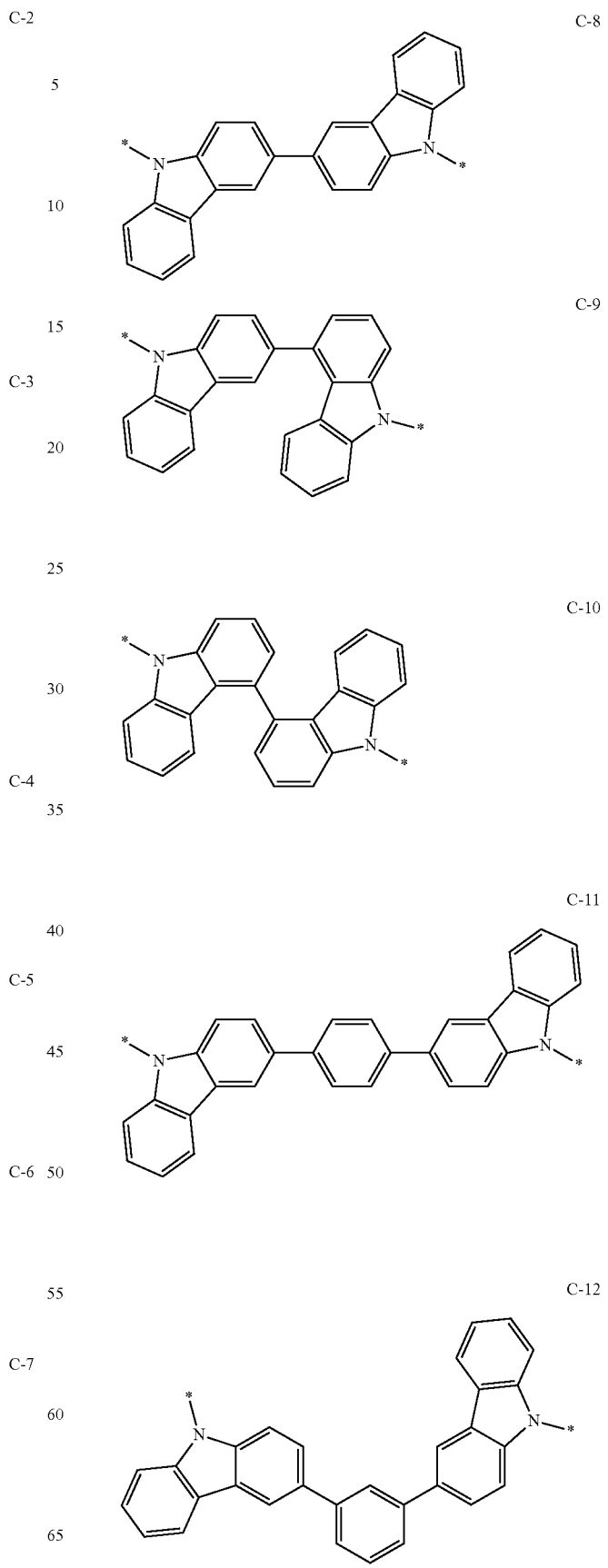

C-13
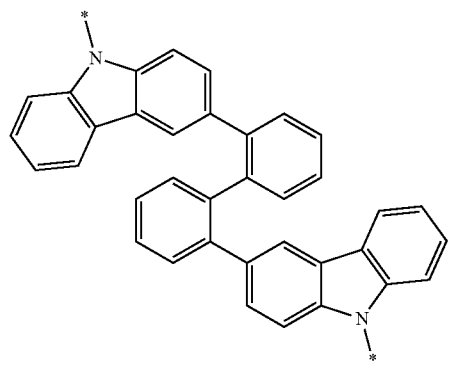
C-18
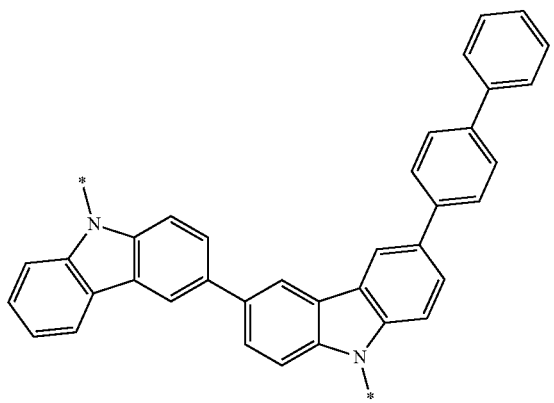
C-14
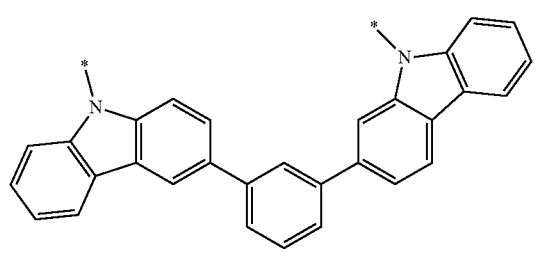
[Group IV]
B-1
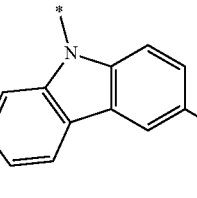
B-2
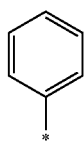
C-15
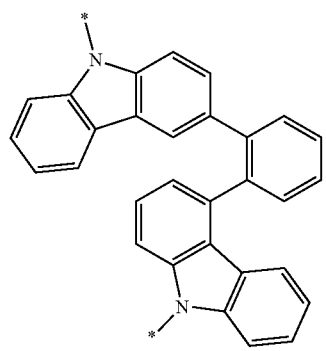
B-3
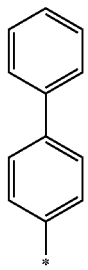
C-16
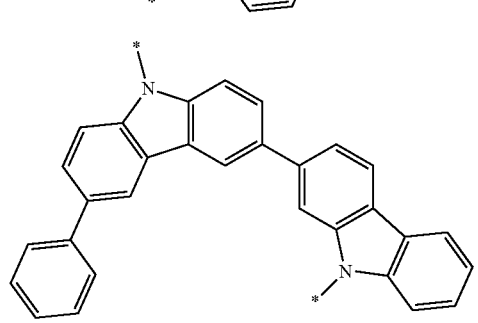
B-4
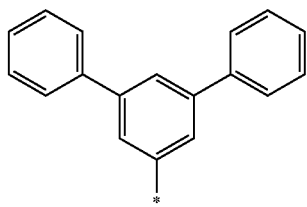
C-17
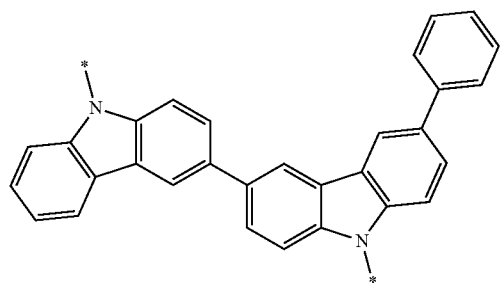
B-5
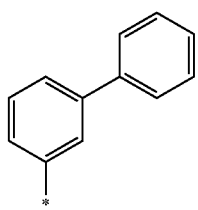
B-6
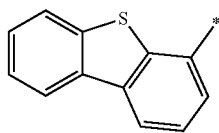

-continued
B-7 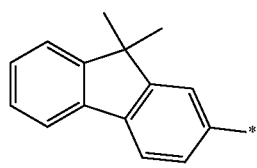
B-8 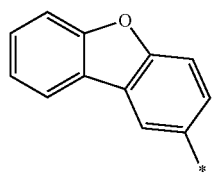
B-9 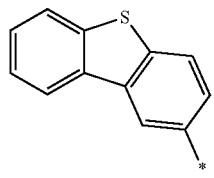
B-10 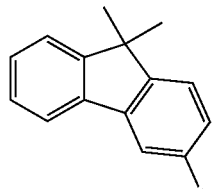
B-11 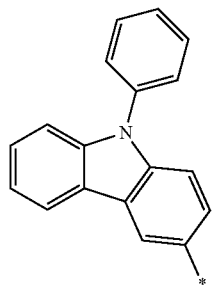
B-12 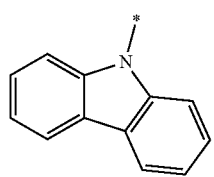
B-13 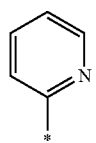
B-14 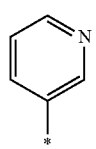
B-15 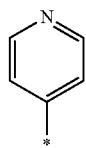
B-16 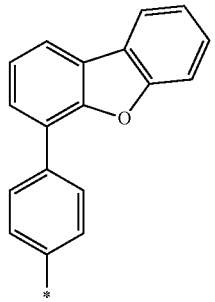
B-17 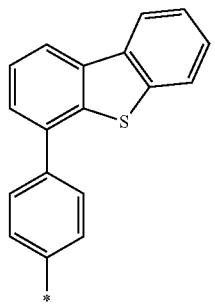
B-18 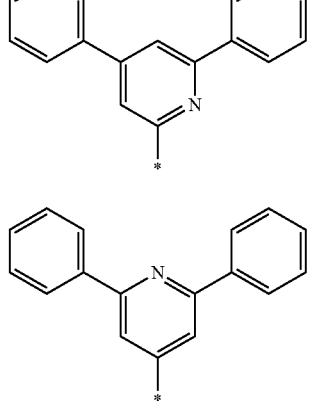
B-19 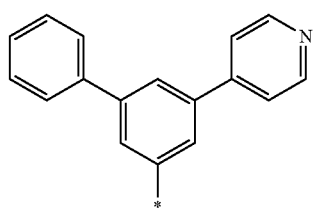
B-20 
B-21 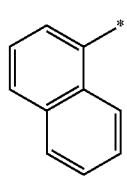

-continued

B-22
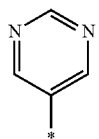

B-23
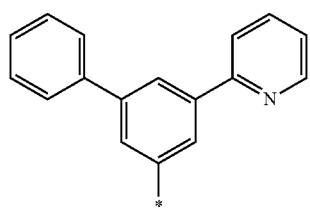

B-24
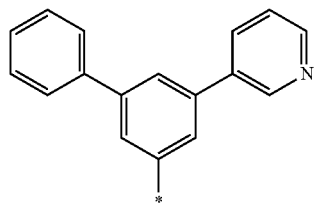

B-25
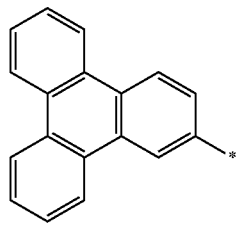

-continued

B-26
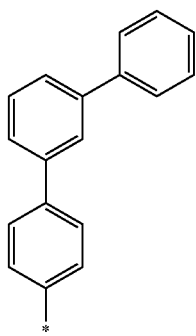

B-27
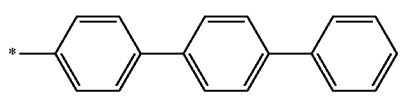

B-28
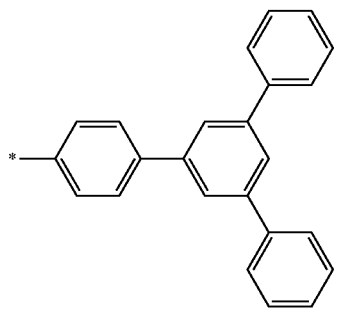

In Group III and Group IV, * is a linking point.

In a most specific example embodiment, Chemical Formula 2 may be represented by C-8 or C-17 of Group III and *—Y¹—Ar¹ and *—Y²—Ar² of Chemical Formula 2 may independently be B-1 to B-3 of Group IV.

The second compound for an organic optoelectric device represented by Chemical Formula 2 may be for example compounds of Group 2, but is not limited thereto.

[Group 2]

[B-1]
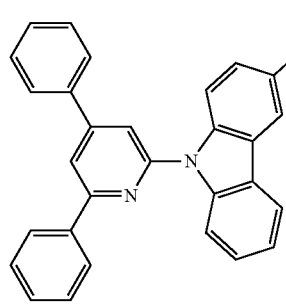

[B-2]
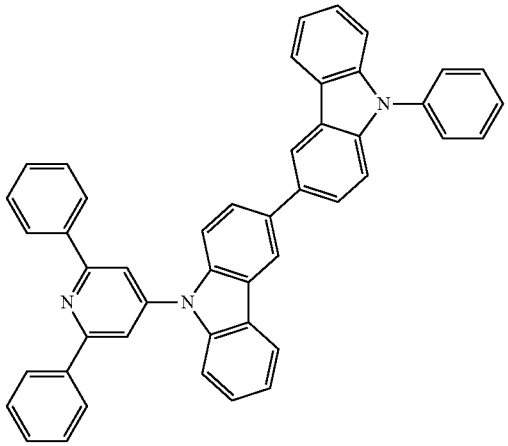

-continued
[B-3]
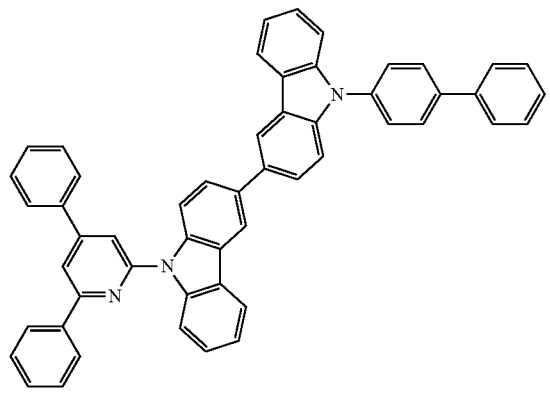
[B-4]
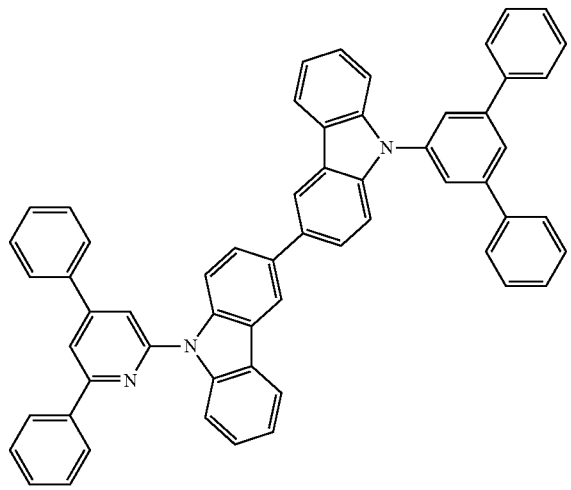
[B-5]
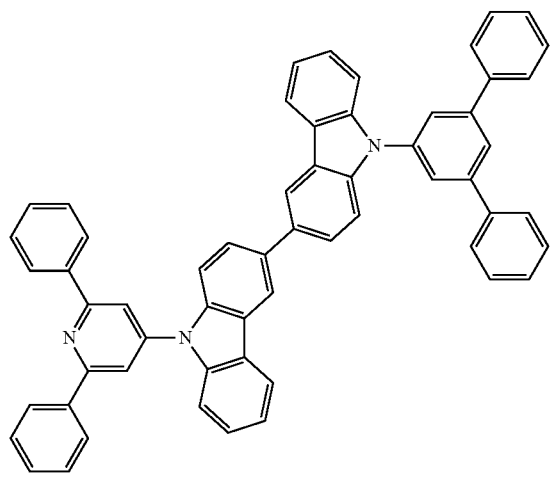
[B-6]
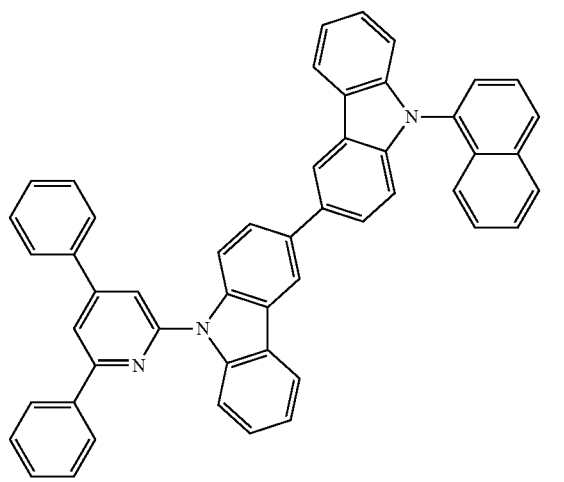
[B-7]
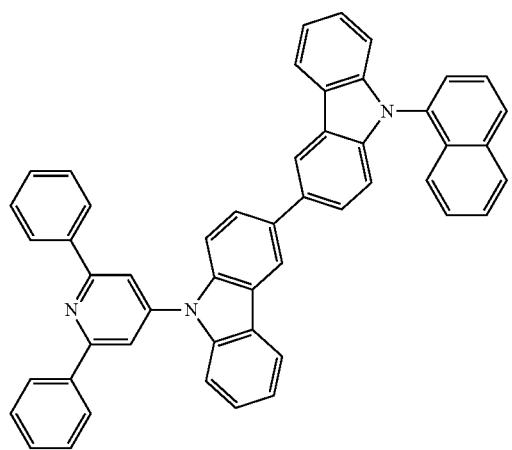
[B-8]
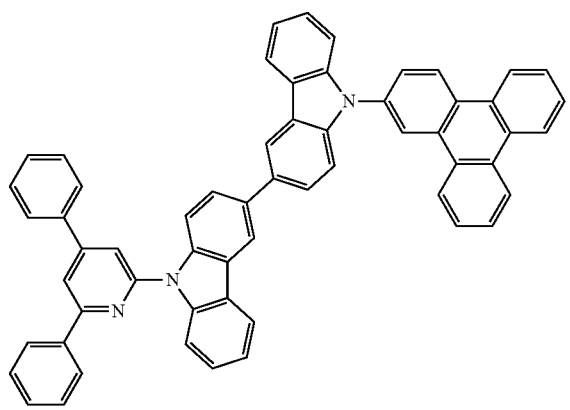

-continued
[B-9]
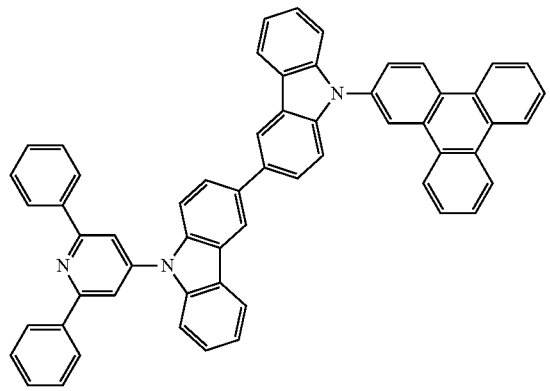
[B-10]
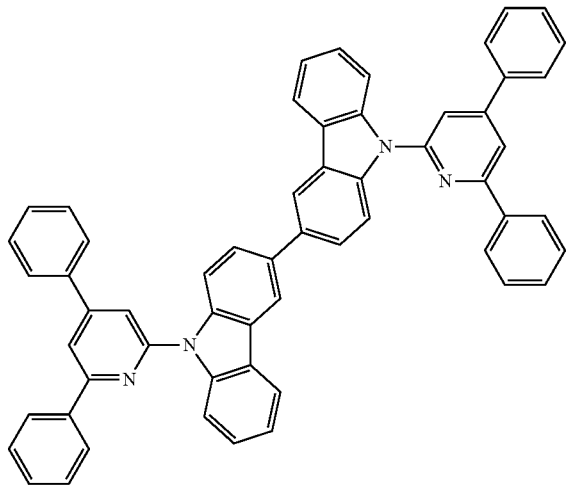
[B-11]
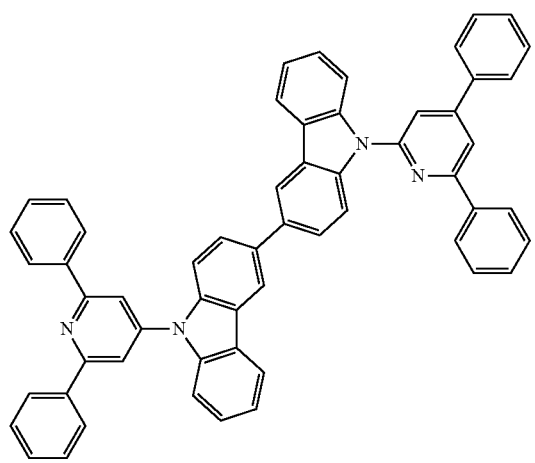
[B-12]
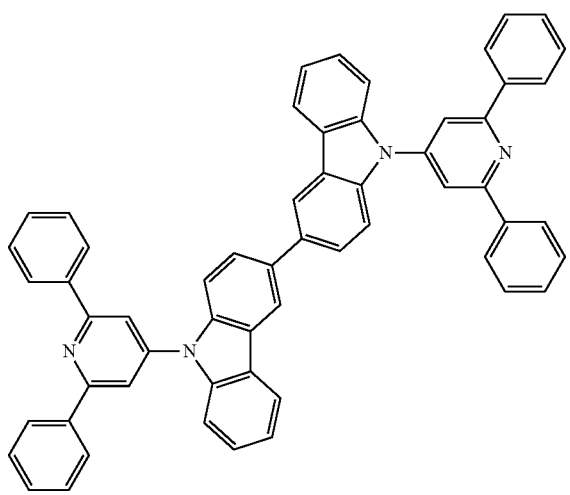
[B-13]
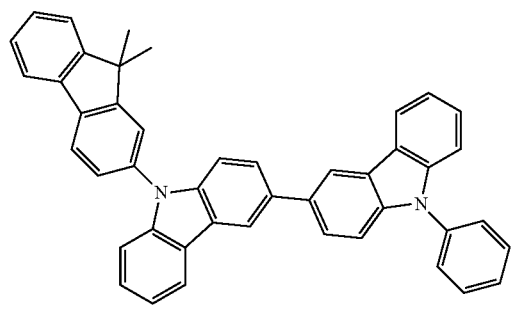
[B-14]
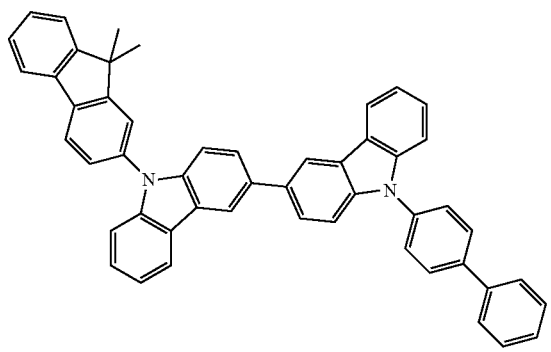

-continued
[B-15]
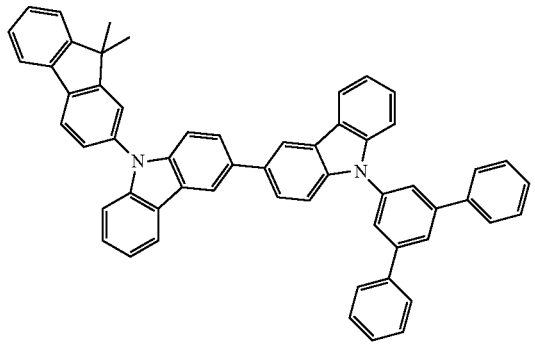
[B-16]
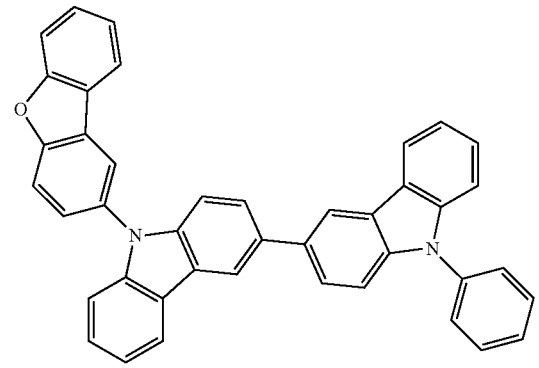
[B-17]
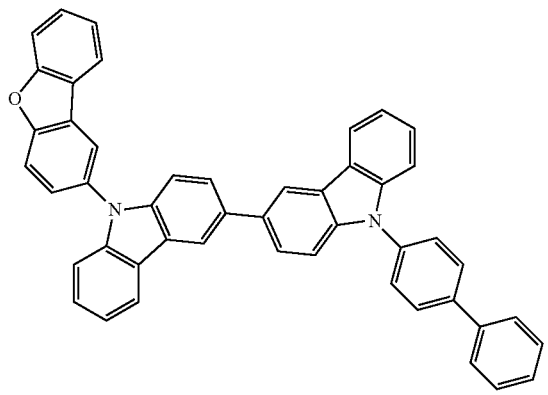
[B-18]
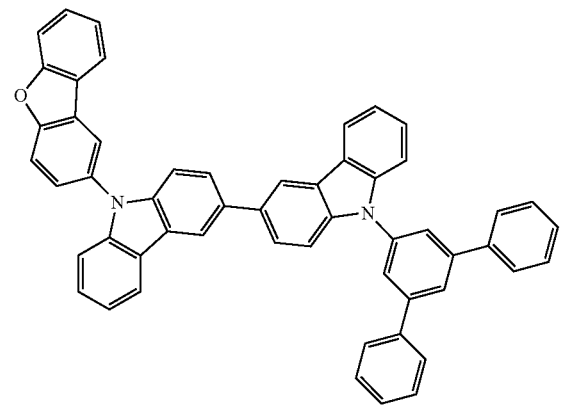
[B-19]
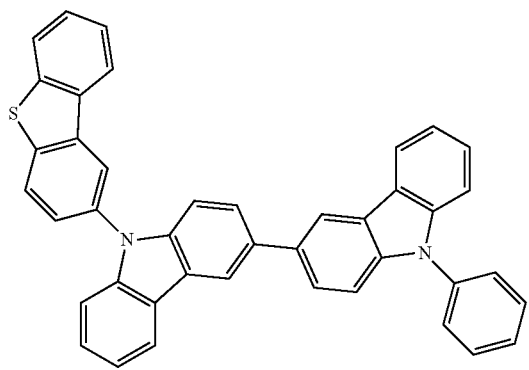
[B-20]
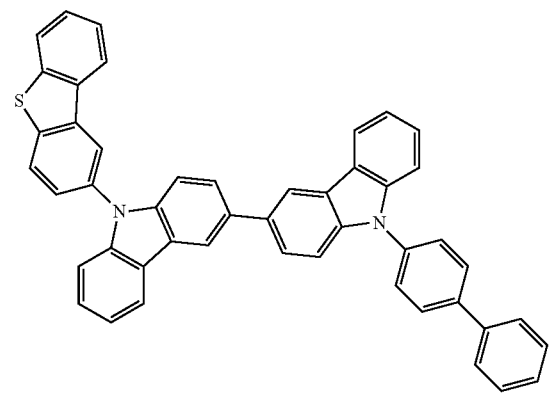

-continued
[B-21]
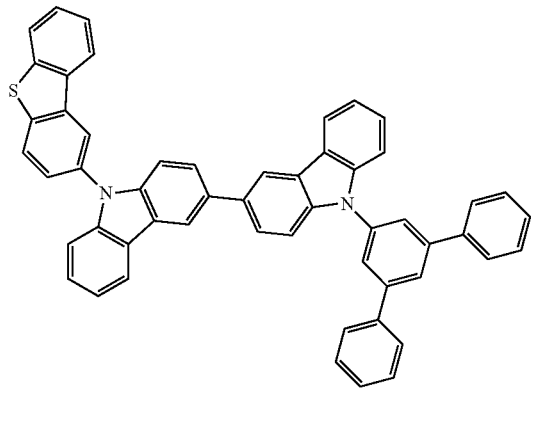
[B-22]
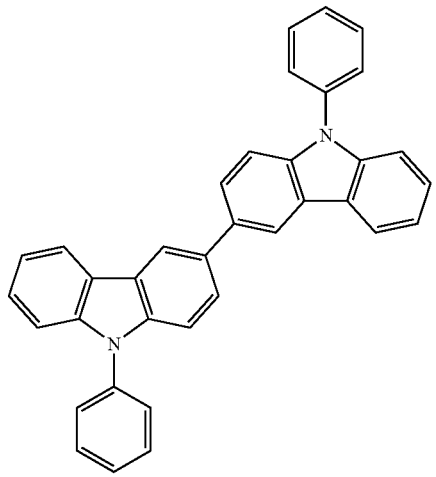
[B-23]
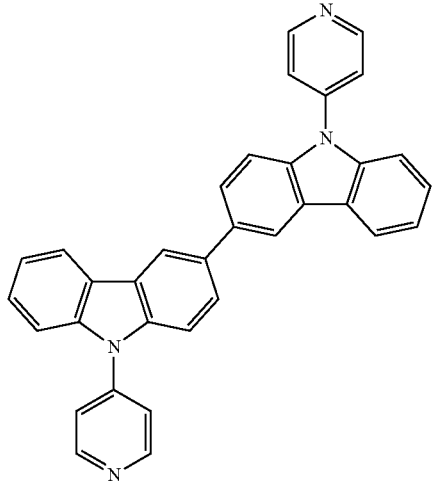
[B-24]
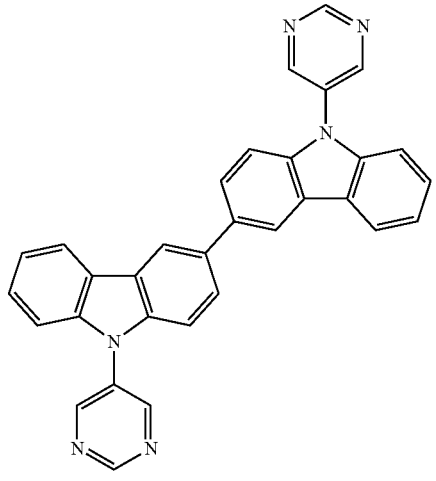
[B-25]
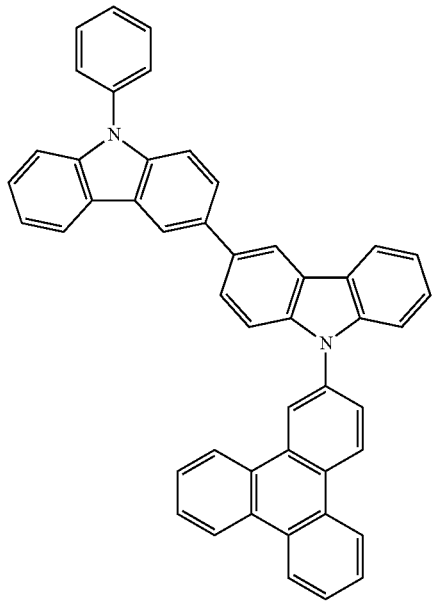
[B-26]
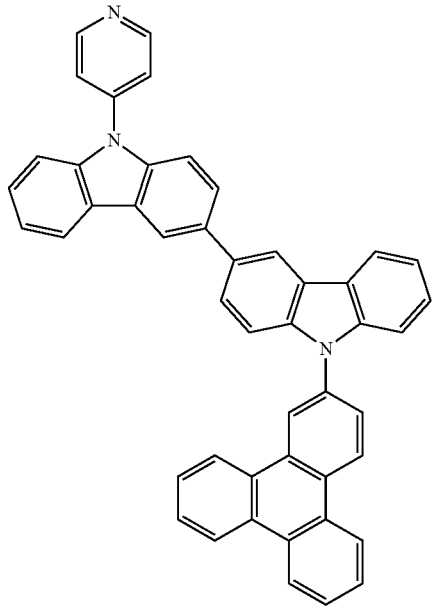

-continued
[B-27]
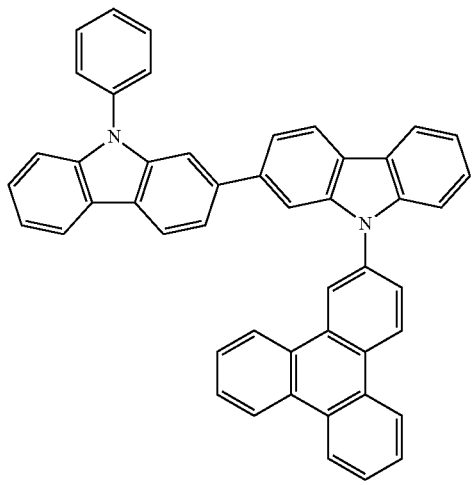
[B-28]
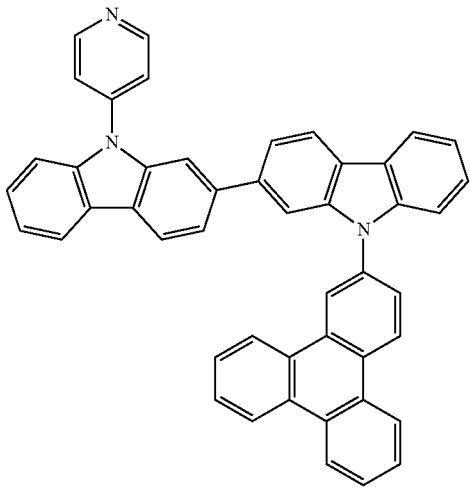
[B-29]
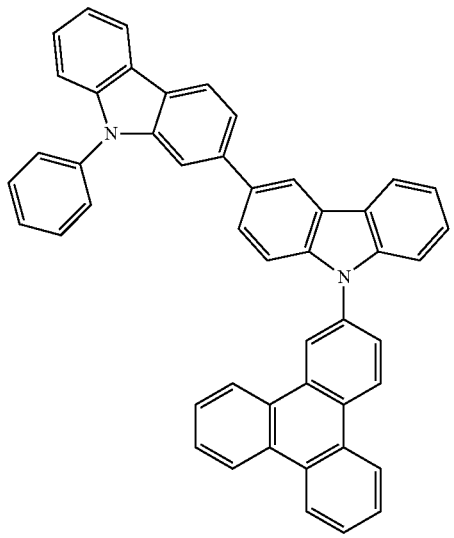
[B-30]
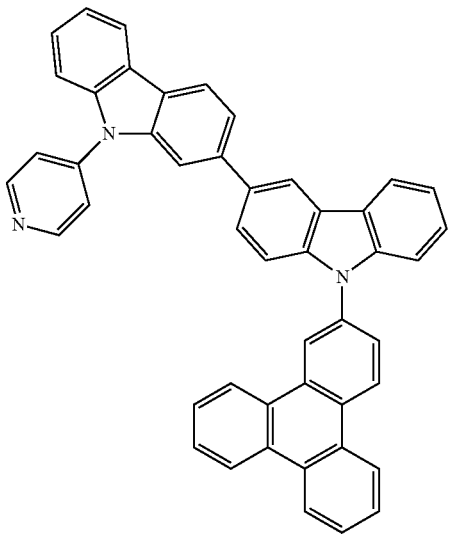
[B-31]
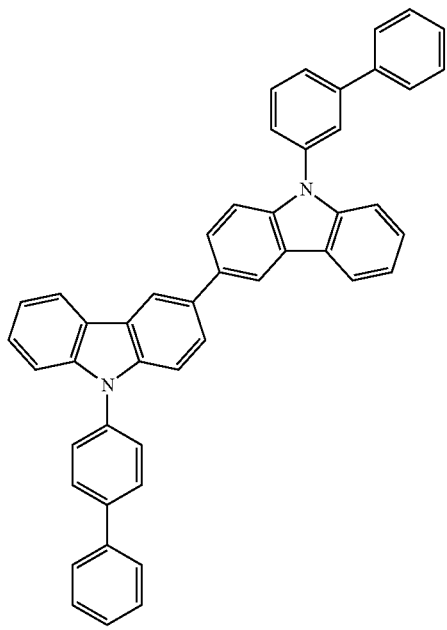
[B-32]
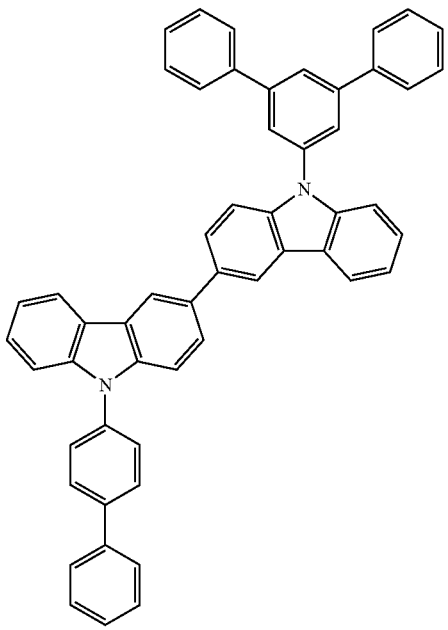

-continued
[B-33]
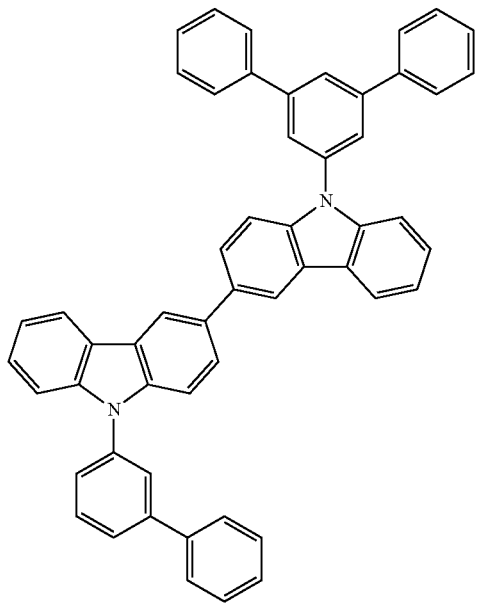
[B-34]
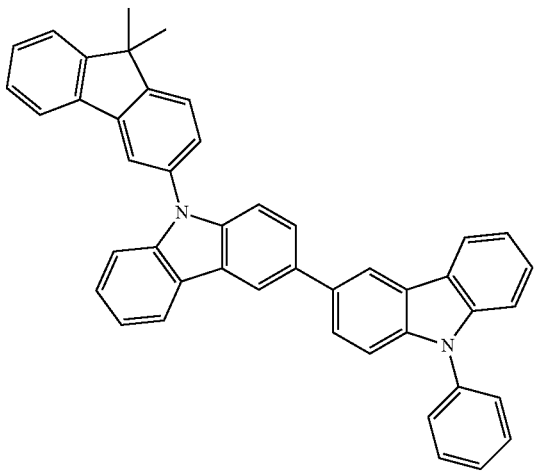
[B-35]
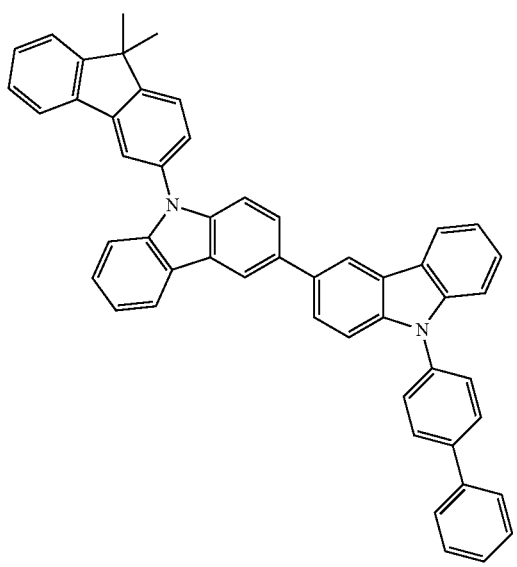
[B-36]
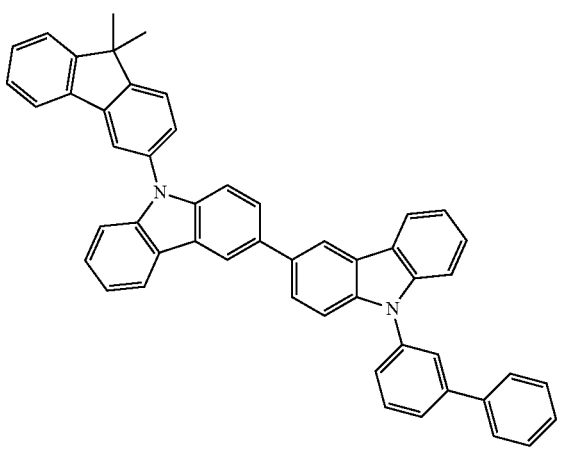

-continued
[B-37]
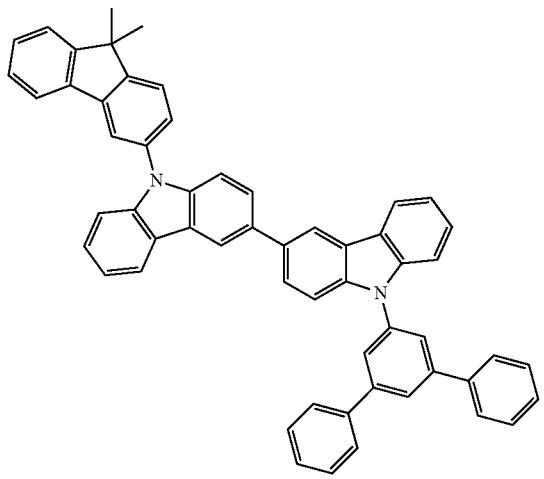
[B-38]
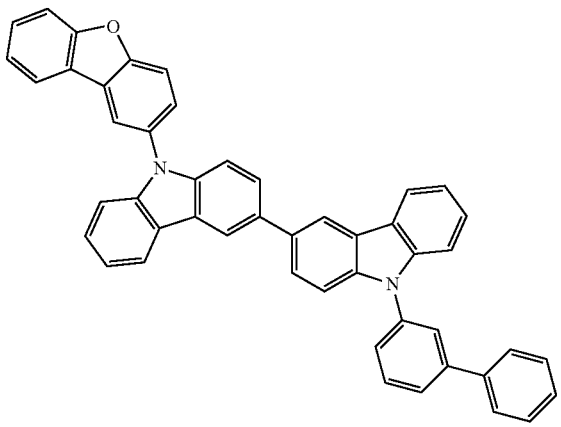
[B-39]
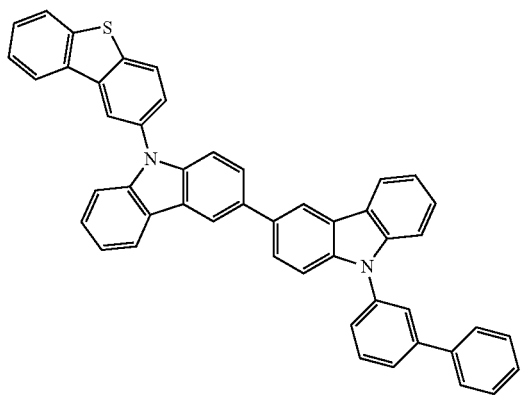
[B-40]
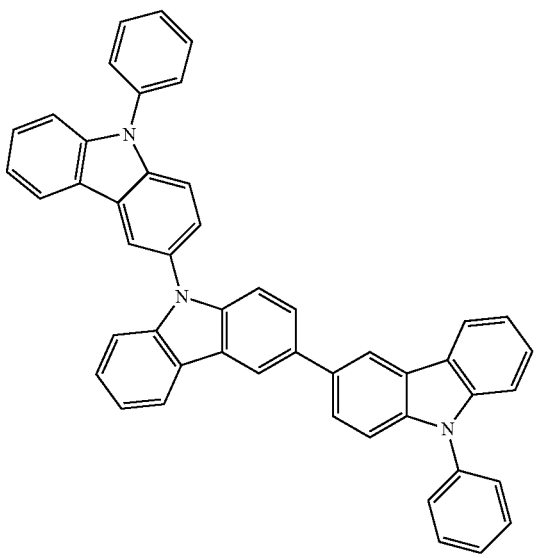
[B-41]
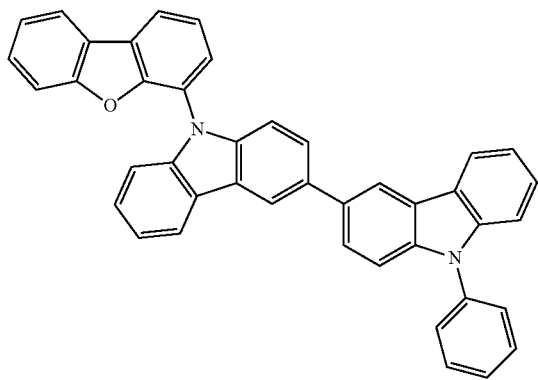
[B-42]
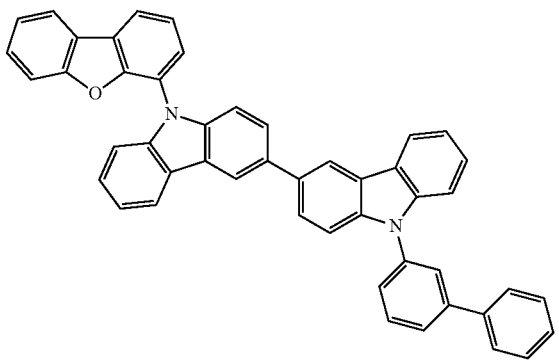

-continued
[B-43]
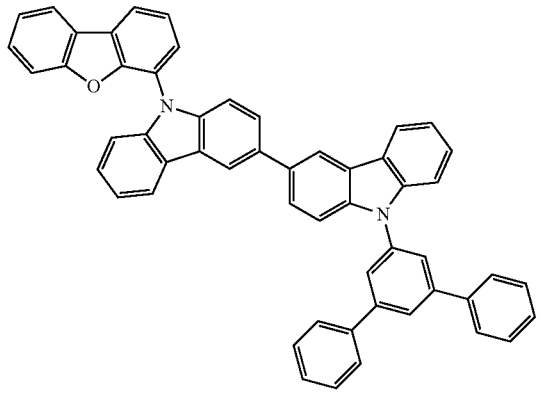
[B-44]
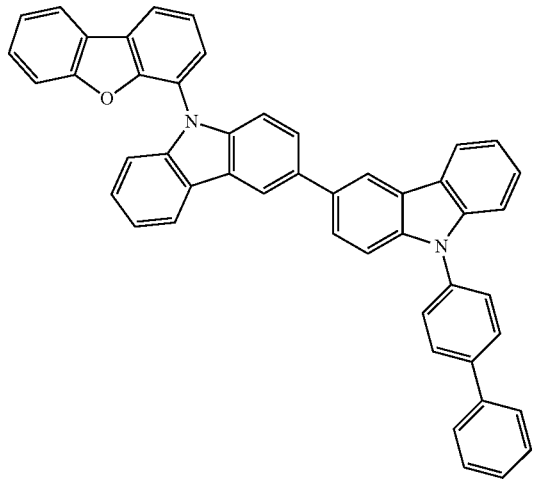
[B-45]
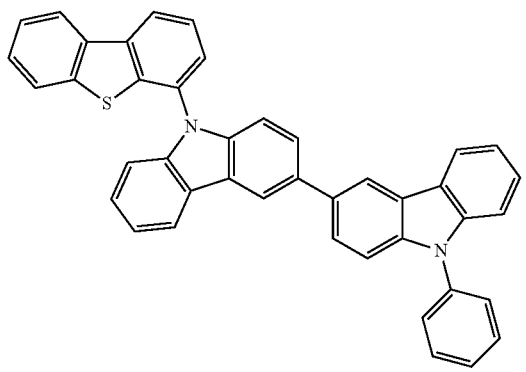
[B-46]
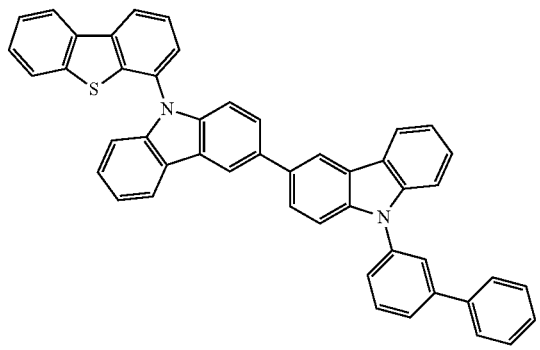
[B-47]
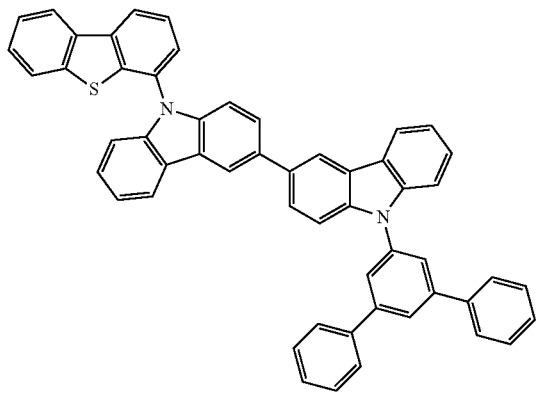
[B-48]
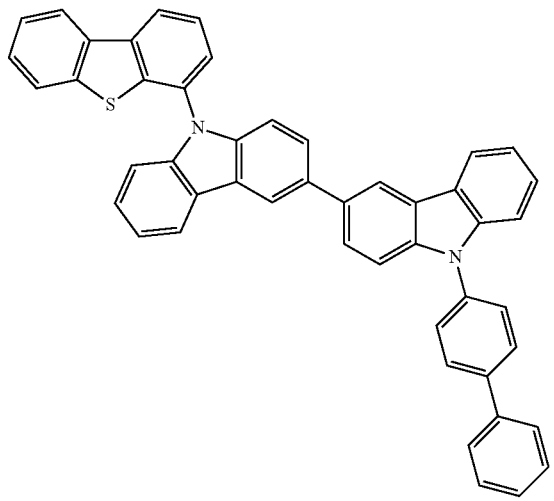

-continued
[B-49]
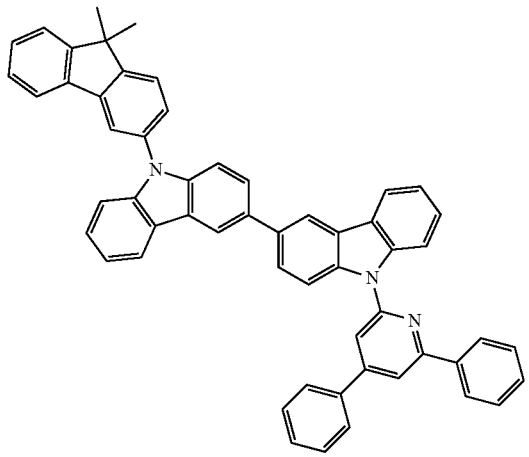
[B-50]
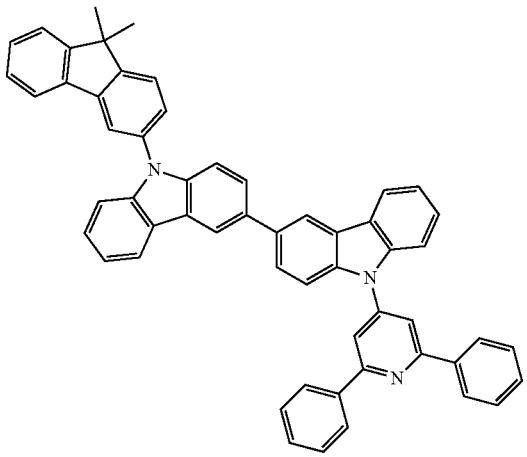
[B-51]
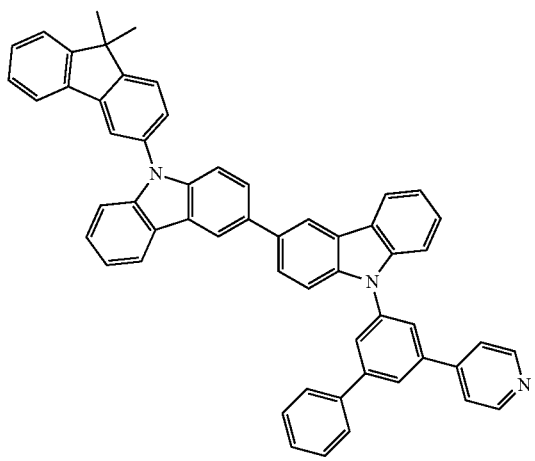
[B-52]
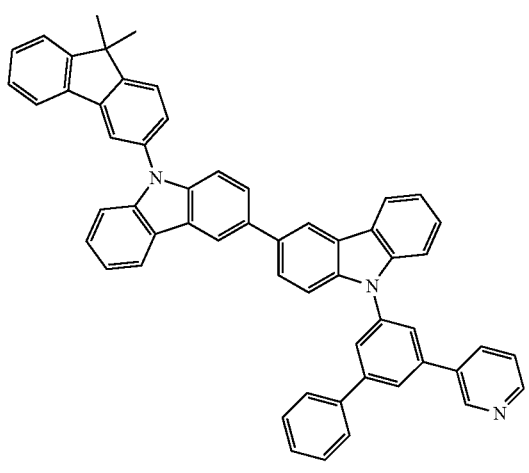
[B-53]
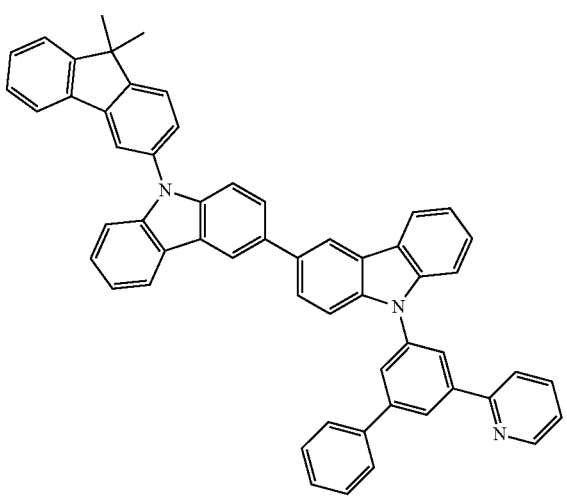

-continued
[B-54]
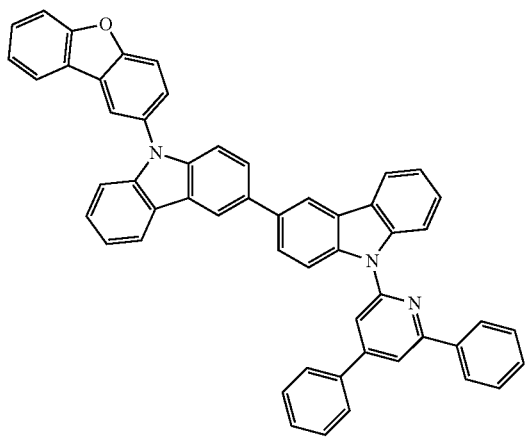
[B-55]
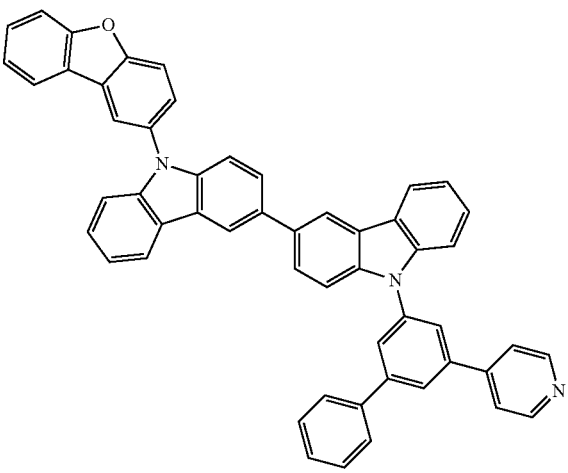
[B-56]
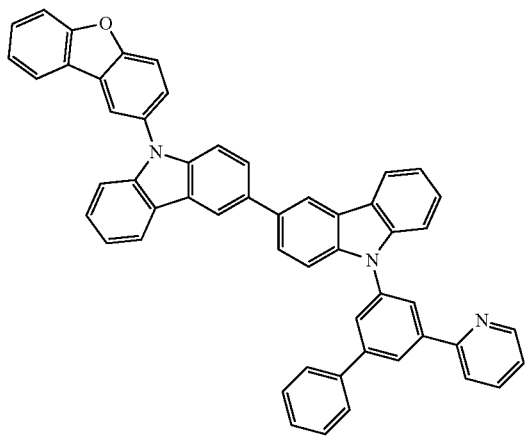
[B-57]
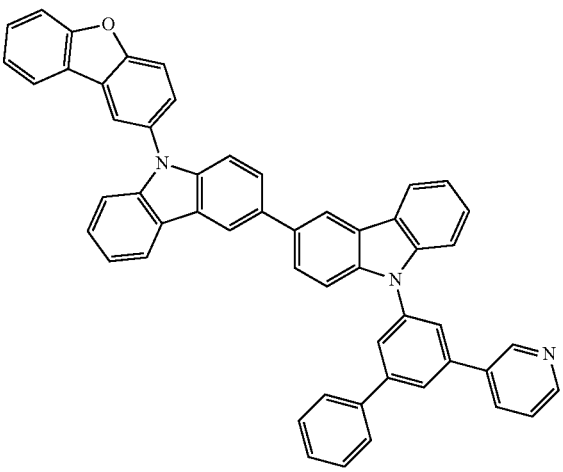
[B-58]
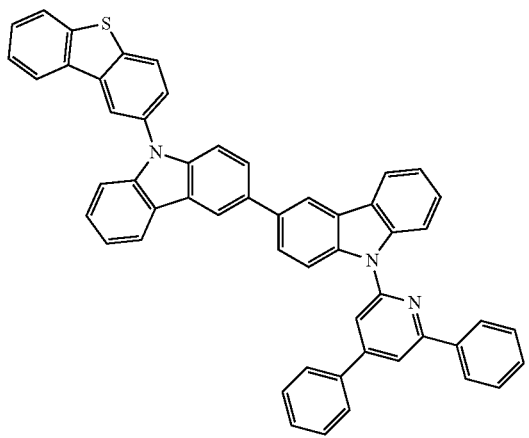
[B-59]
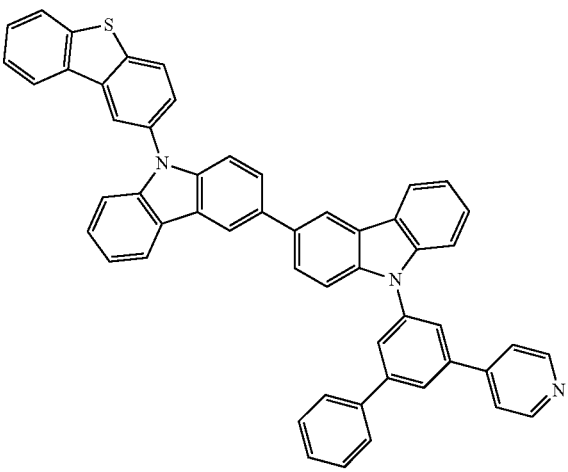

-continued
[B-60]
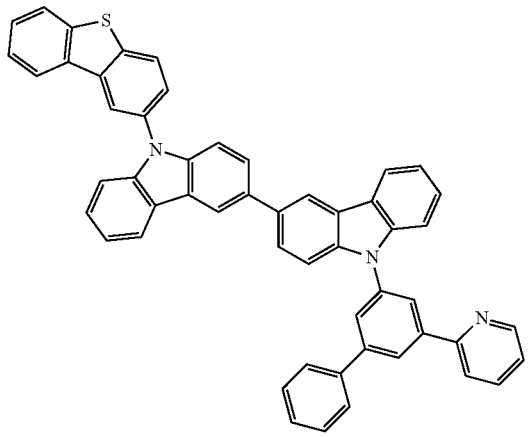
[B-61]
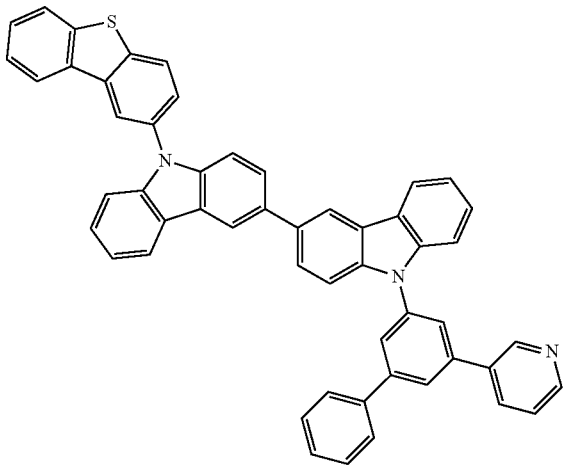
[B-62]
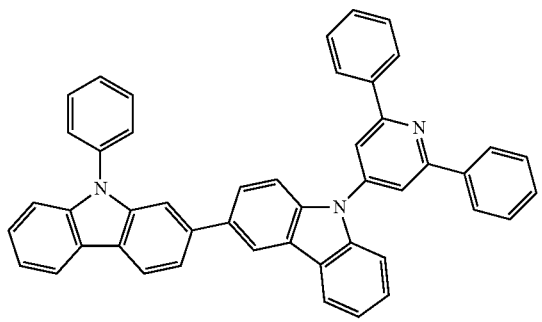
[B-63]
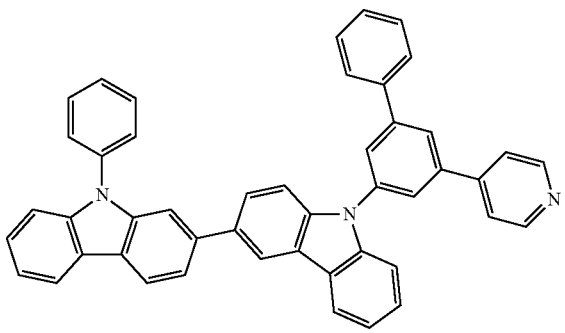
[B-64]
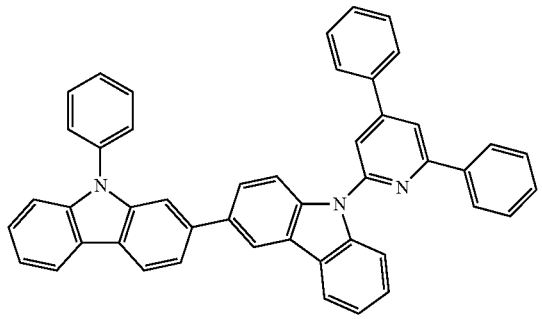
[B-65]
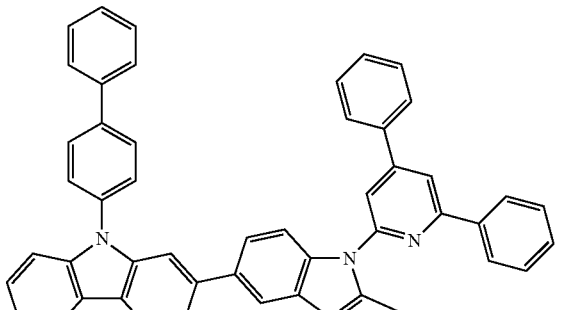
[B-66]
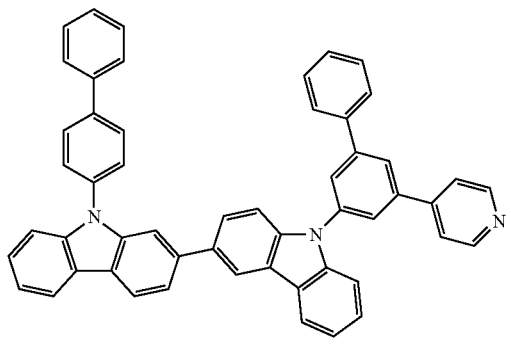
[B-67]
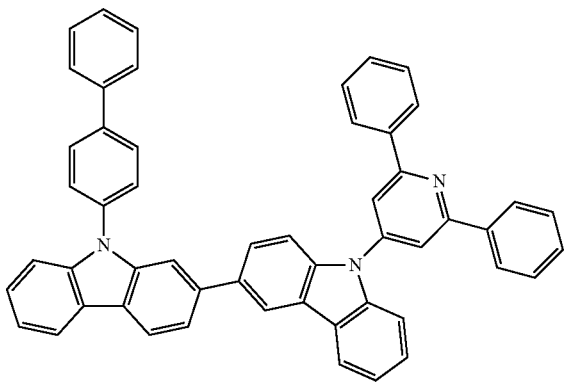

-continued
[B-68]
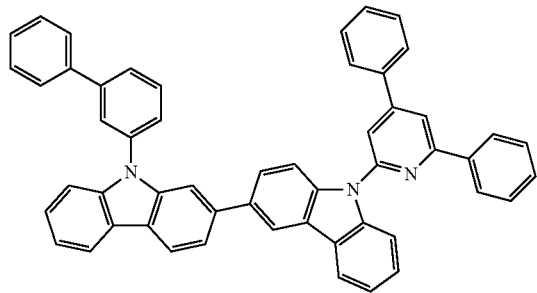
[B-69]
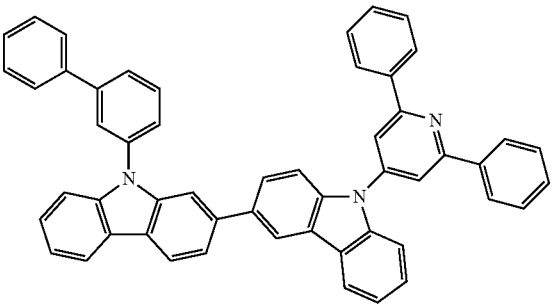
[B-70]
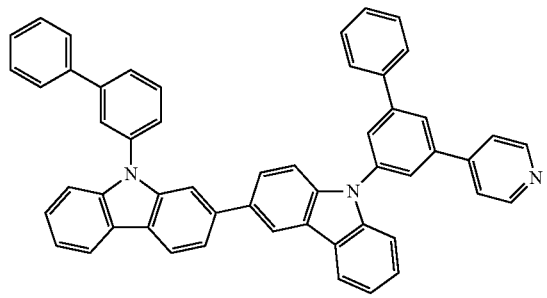
[B-71]
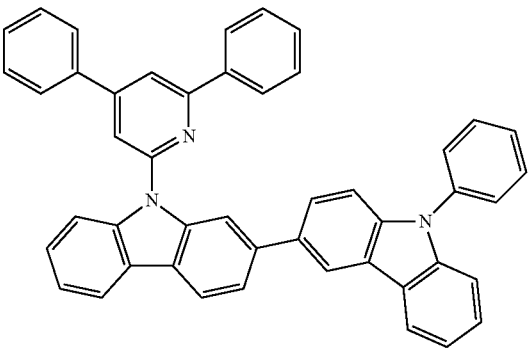
[B-72]
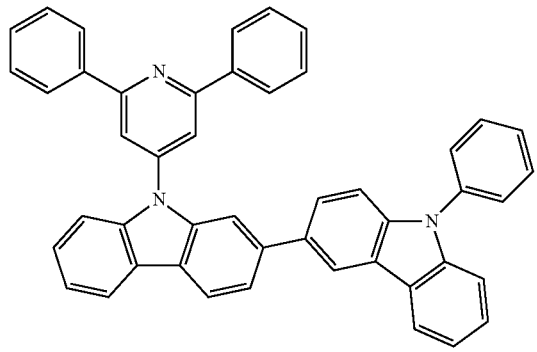
[B-73]
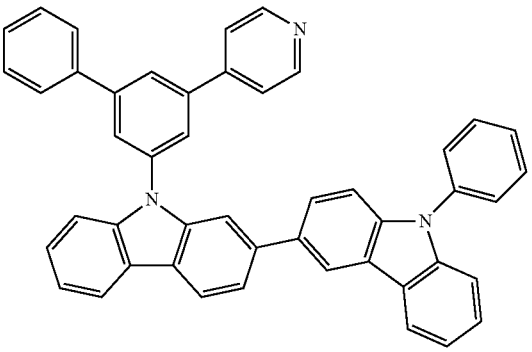
[B-74]
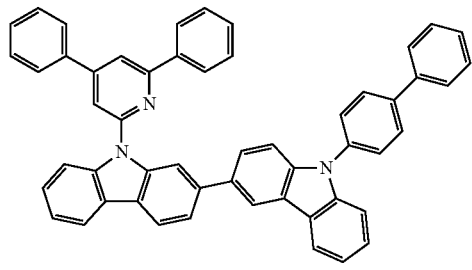
[B-75]
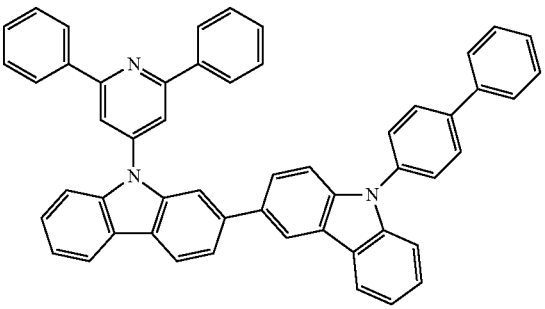

-continued
[B-76]
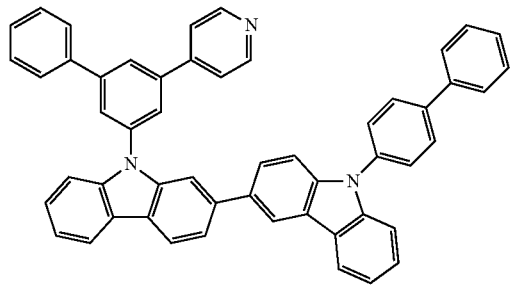
[B-77]
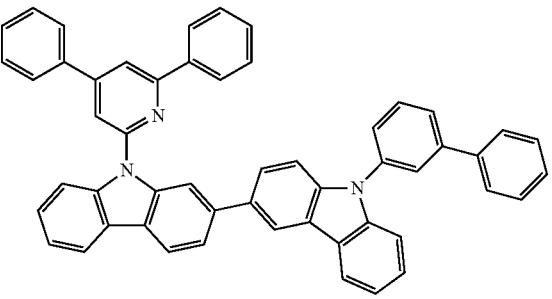
[B-78]
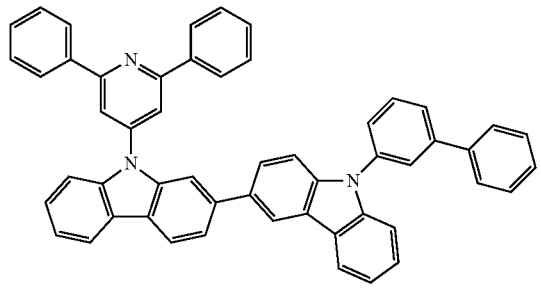
[B-79]
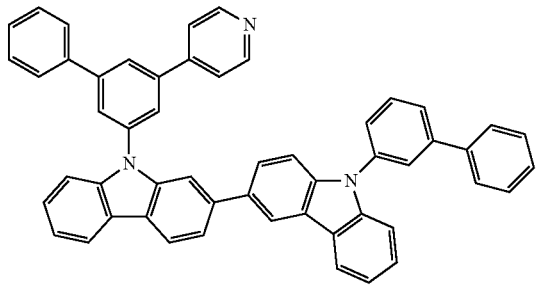
[B-80]
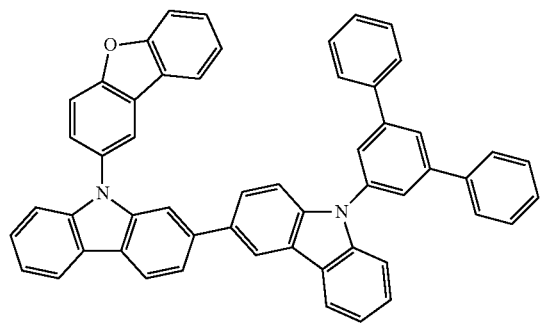
[B-81]
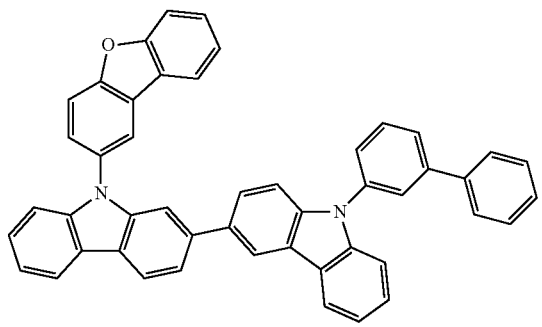
[B-82]
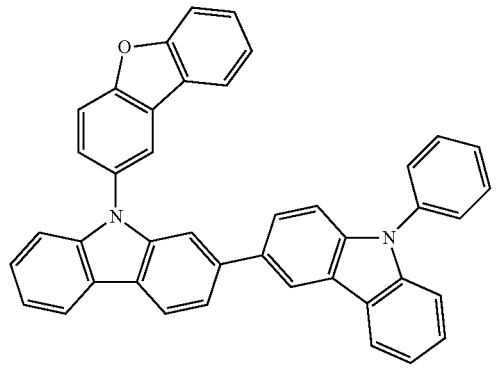
[B-83]
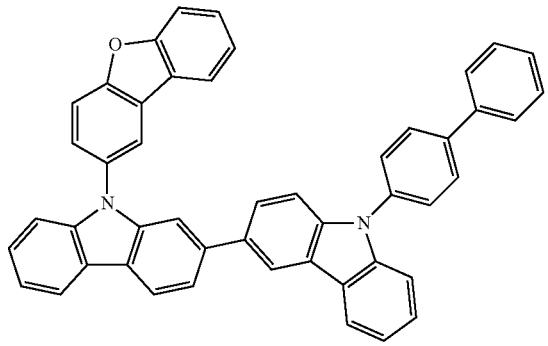

-continued
[B-84]
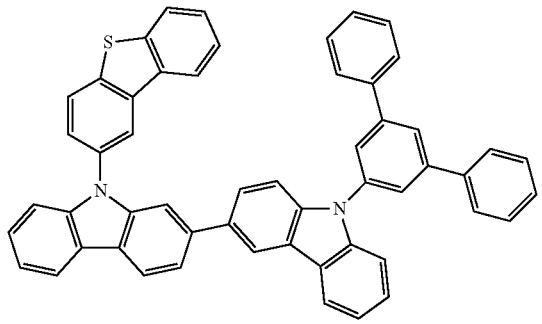
[B-85]
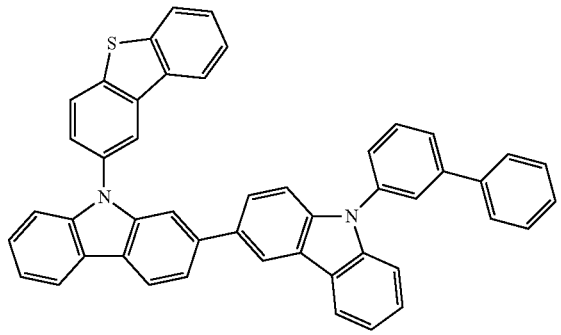
[B-86]
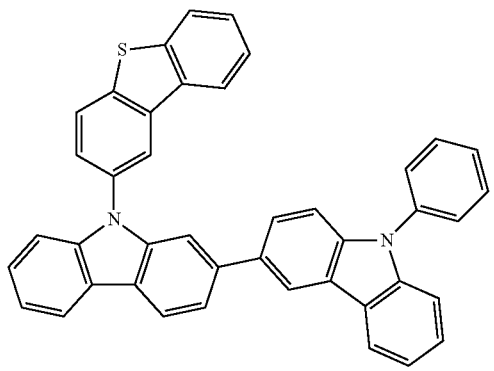
[B-87]
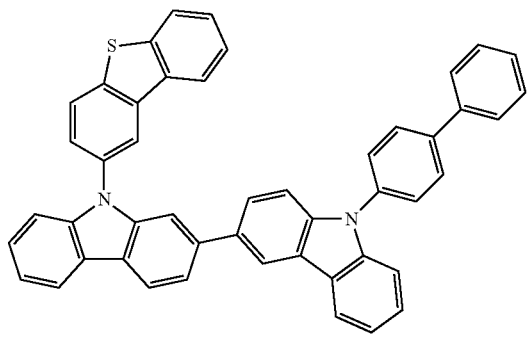
[B-88]
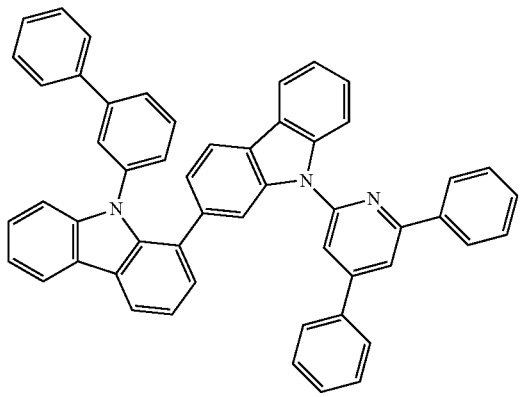
[B-89]
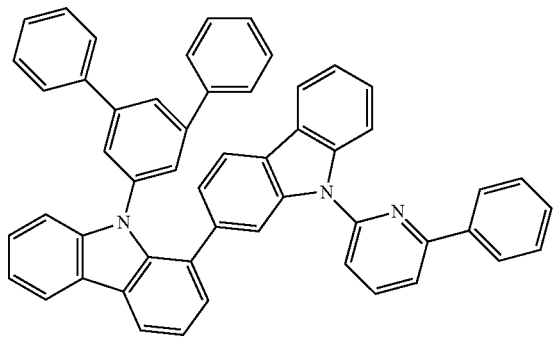
[B-90]
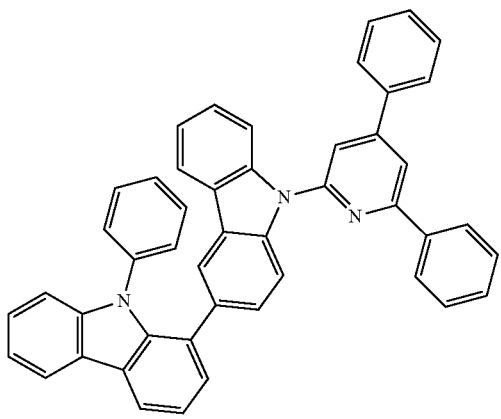
[B-91]
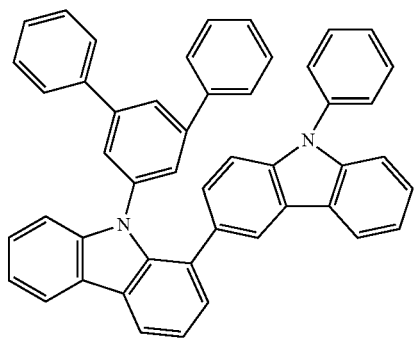

-continued
[B-92]
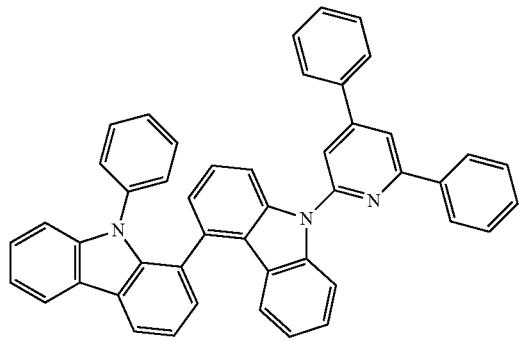
[B-93]
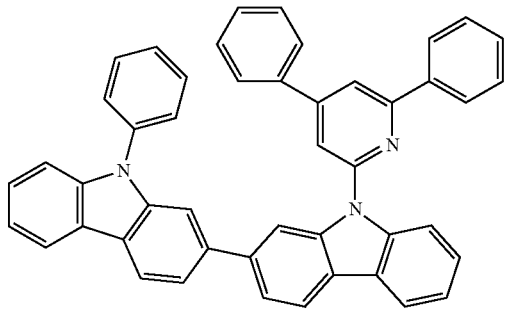
[B-94]
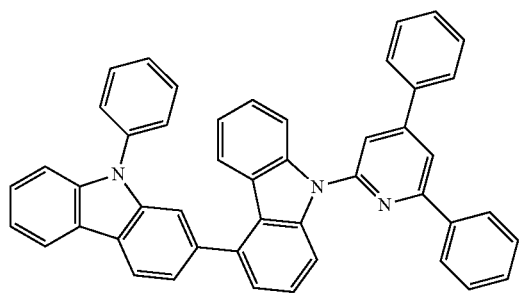
[B-95]
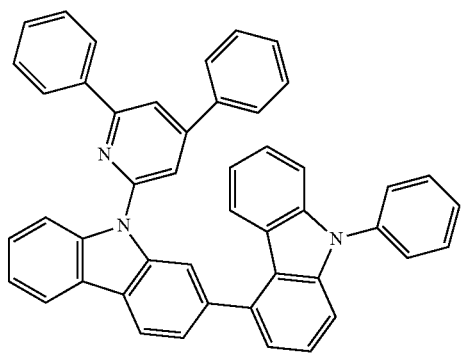
[B-96]
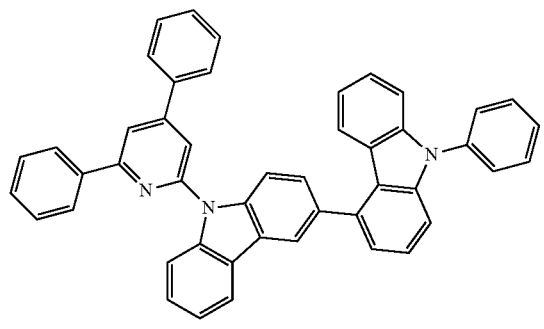
[B-97]
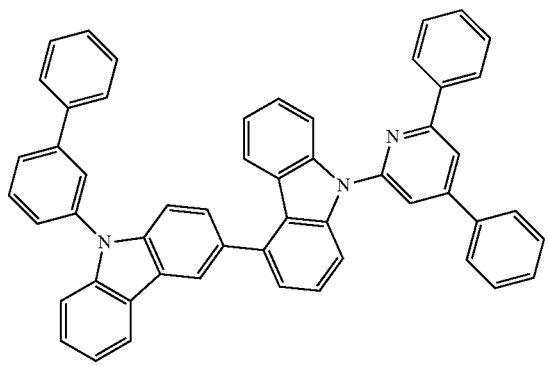

-continued
[B-98]
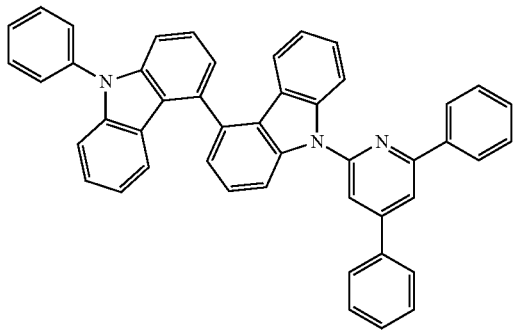
[B-99]
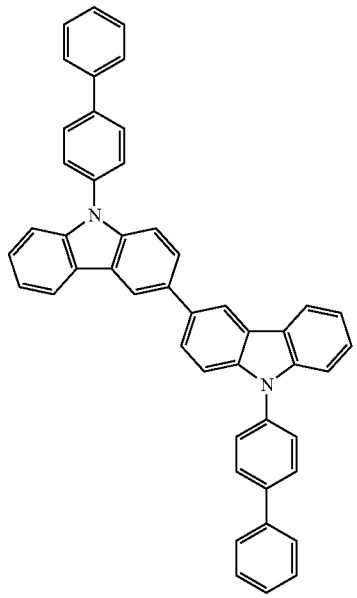
[B-100]
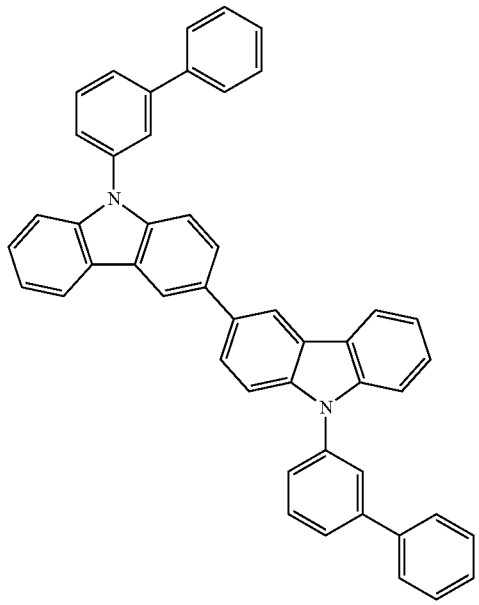
[B-101]
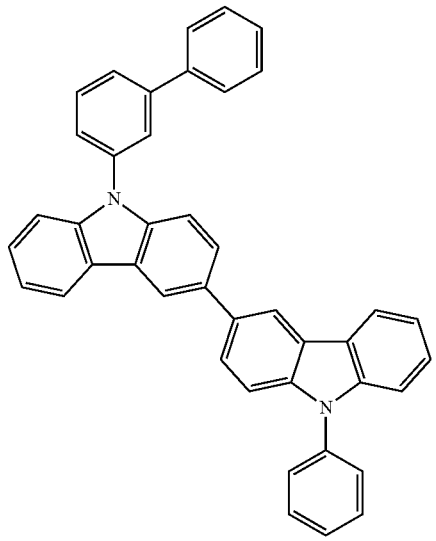
[B-102]
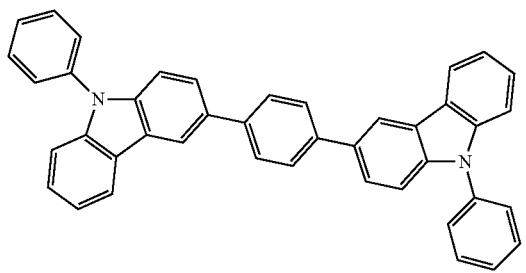
[B-103]
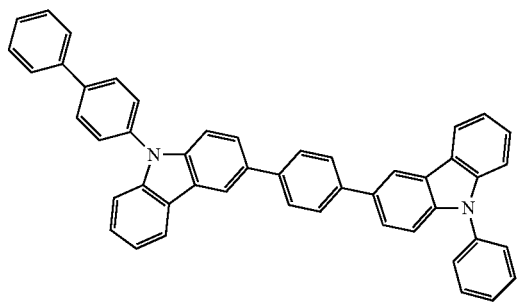

[B-104]
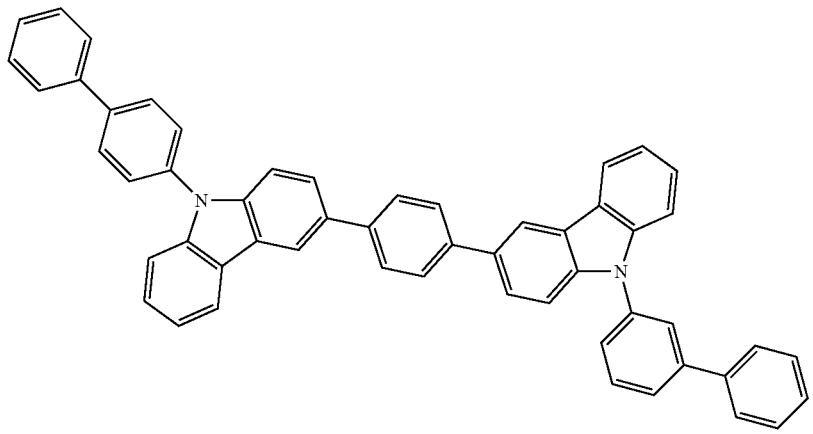
[B-105]     [B-106]
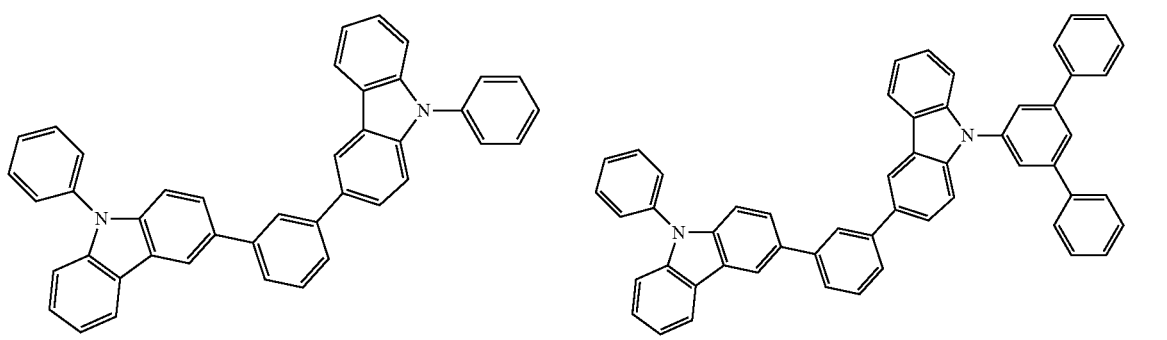
[B-107]
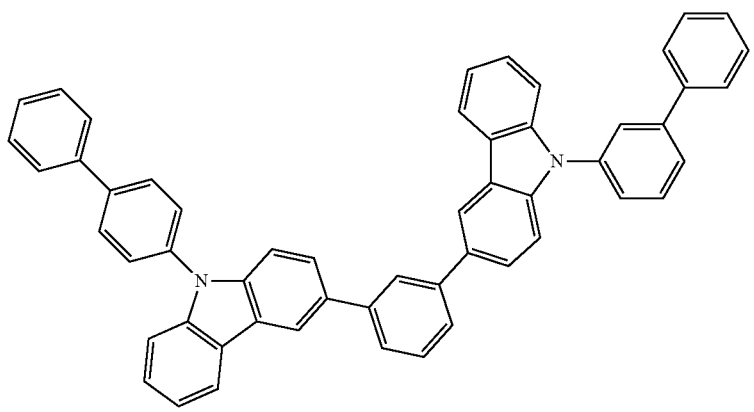
[B-108]     [B-109]
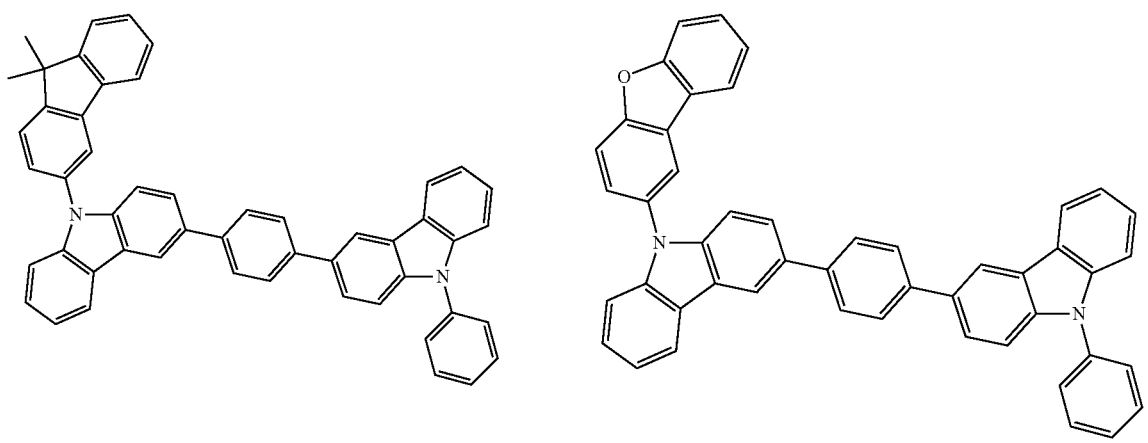

-continued
[B-110]
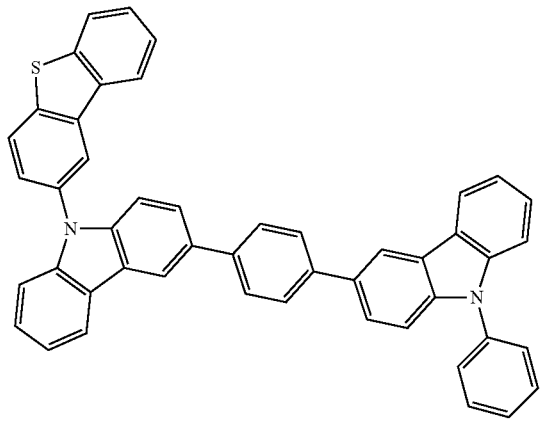
[B-111]
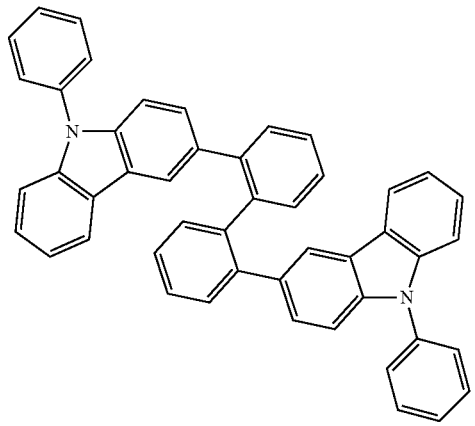
[B-112]
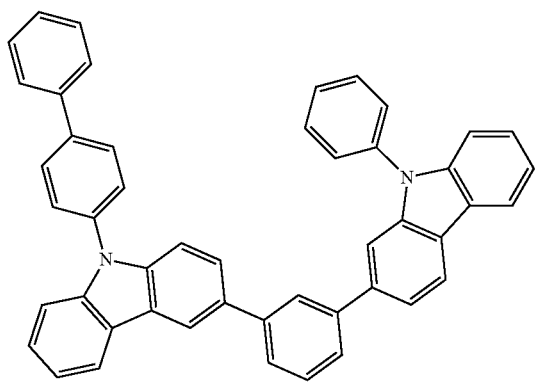
[B-113]
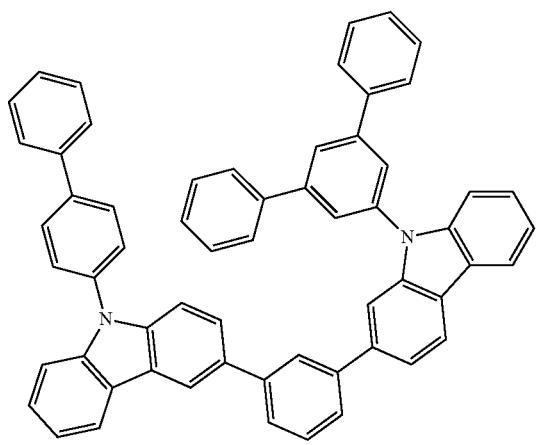
[B-114]
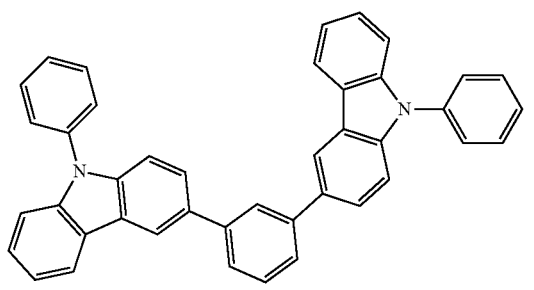
[B-115]
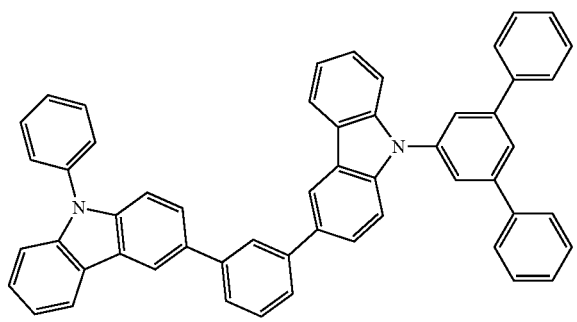

-continued
[B-116] [B-117]
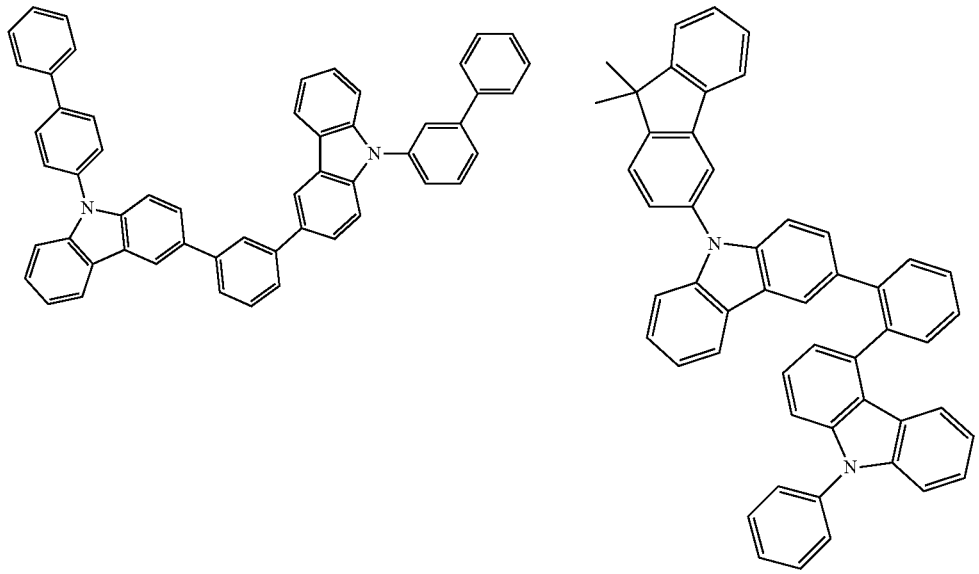
[B-118] [B-119]
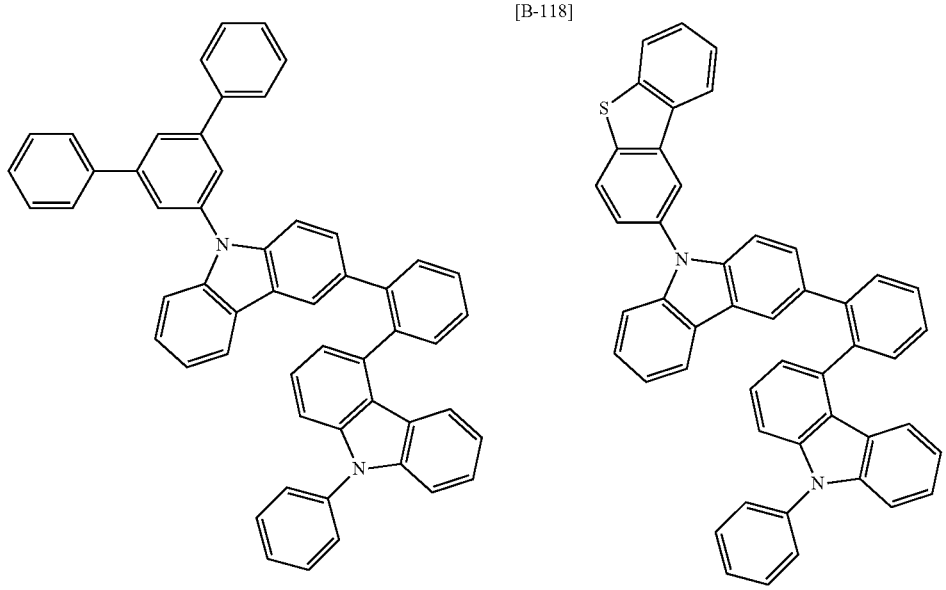
[B-120] [B-121]
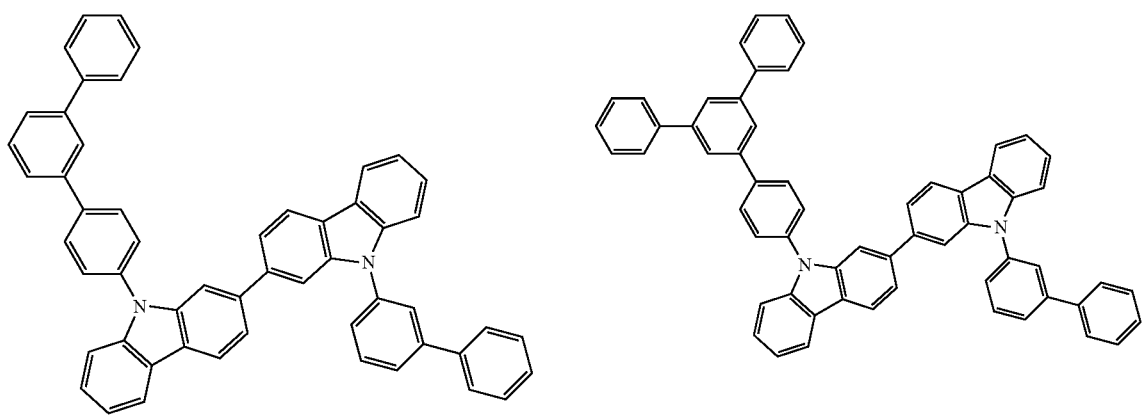

[B-122]
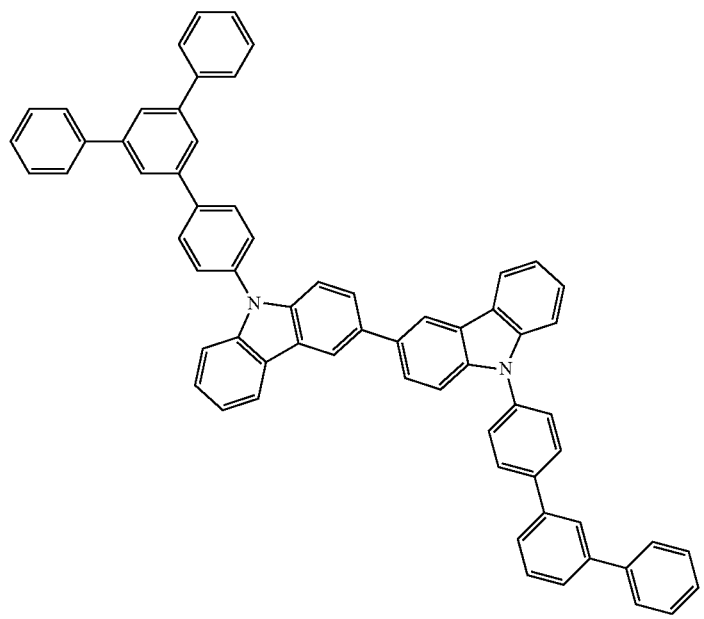
[B-123]
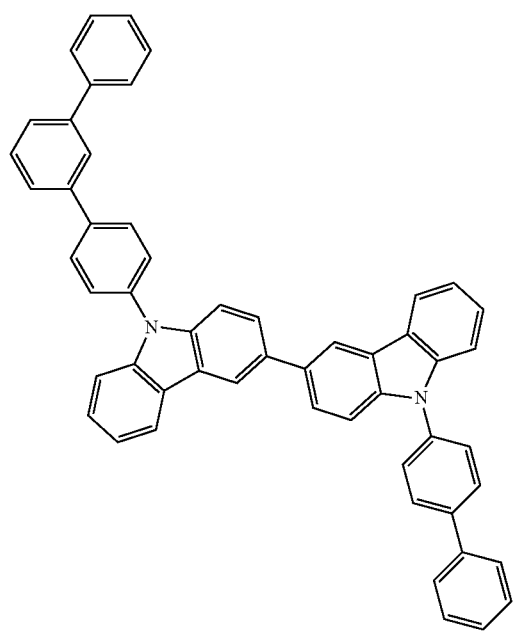

-continued
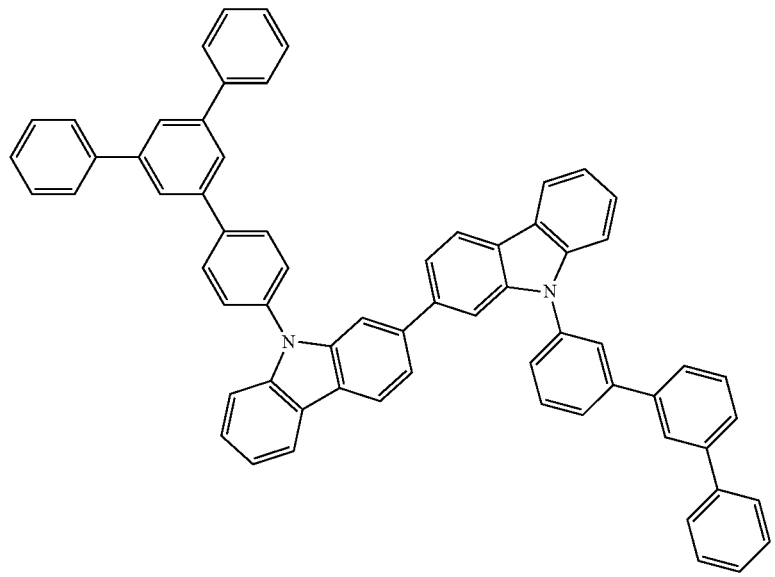
[B-124]
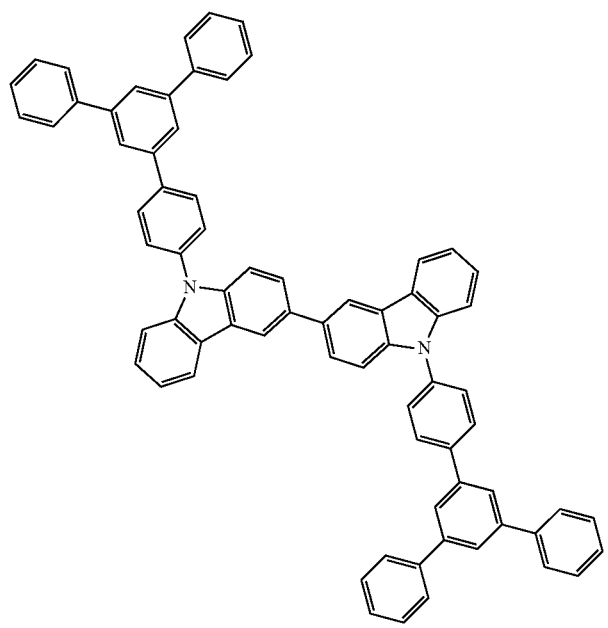
[B-125]

[B-126]
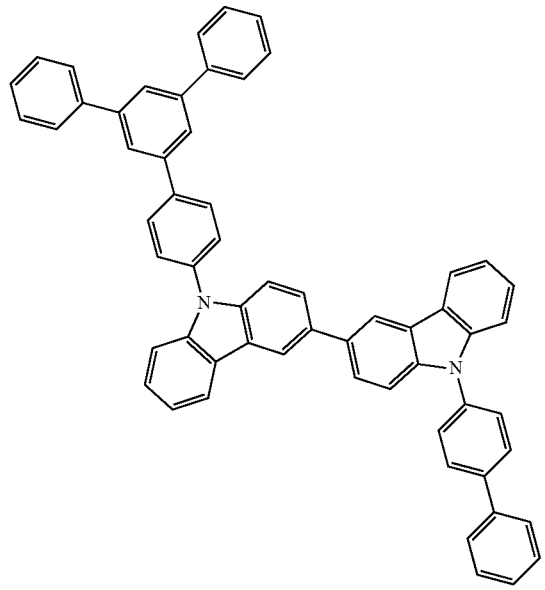
[B-127]
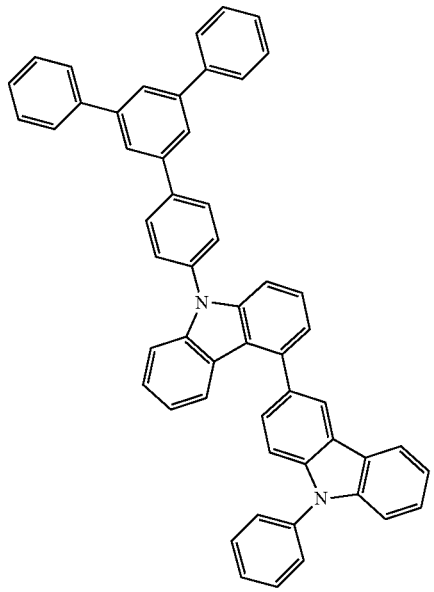
[B-128]
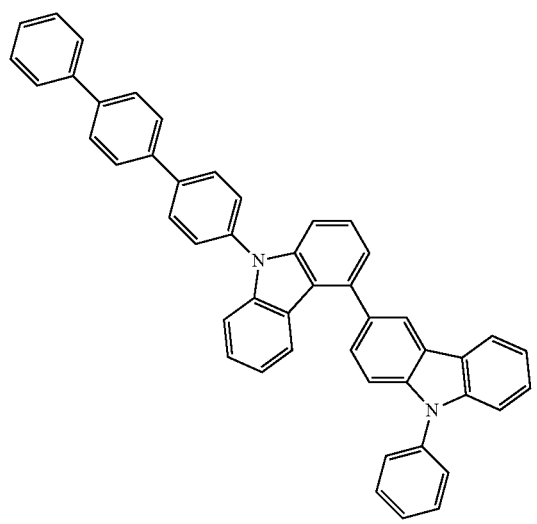
[B-129]
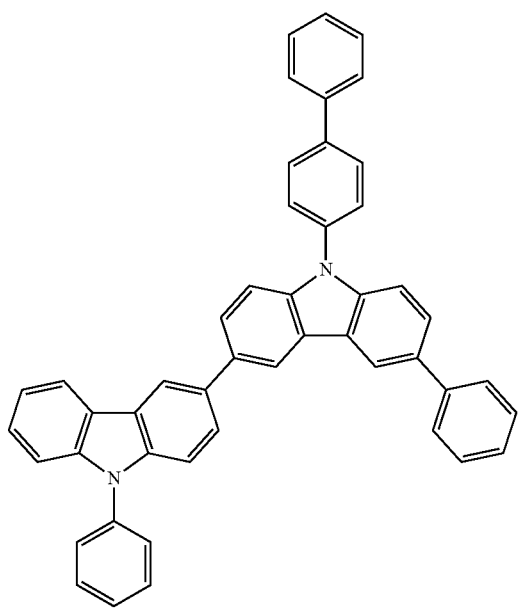

-continued
[B-130]
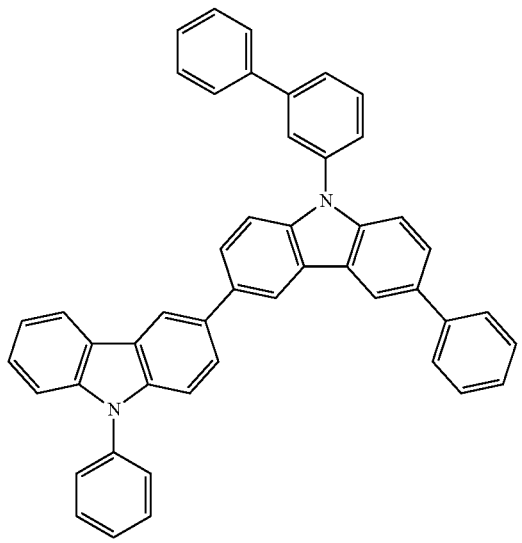
[B-131]
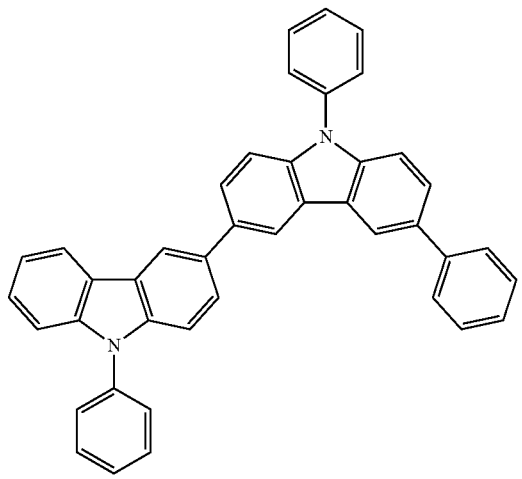
[B-132]
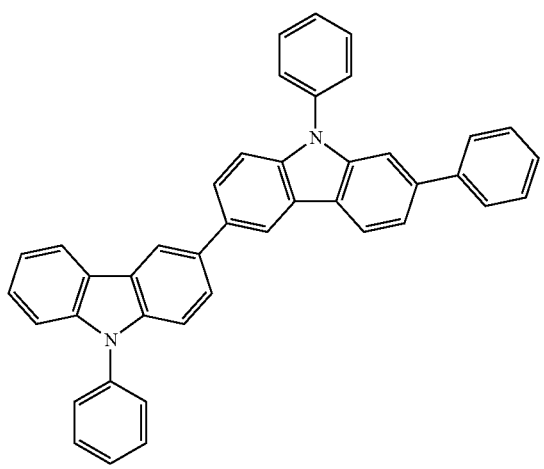
[B-133]
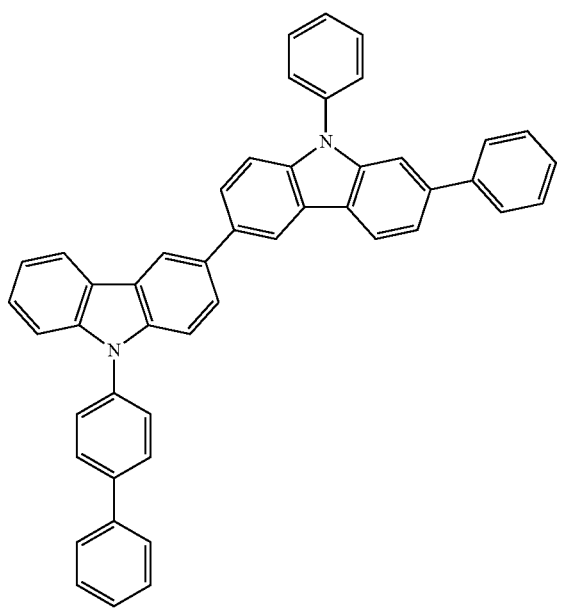

[B-134]
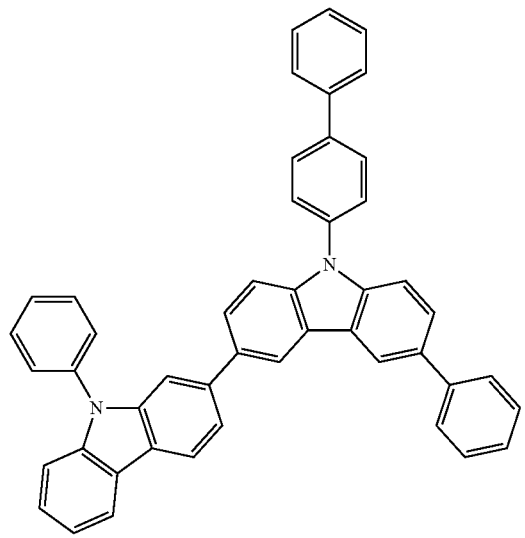
[B-135]
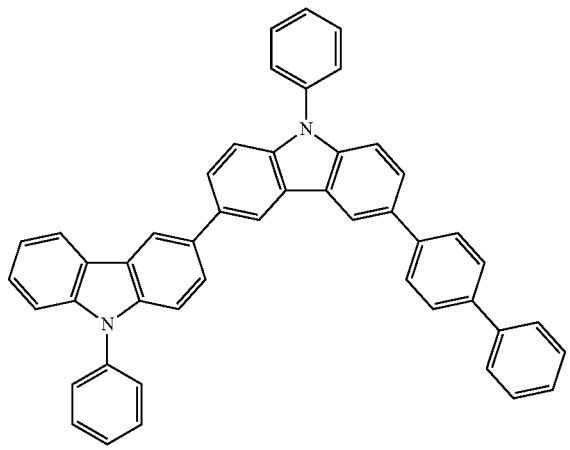
[B-136]
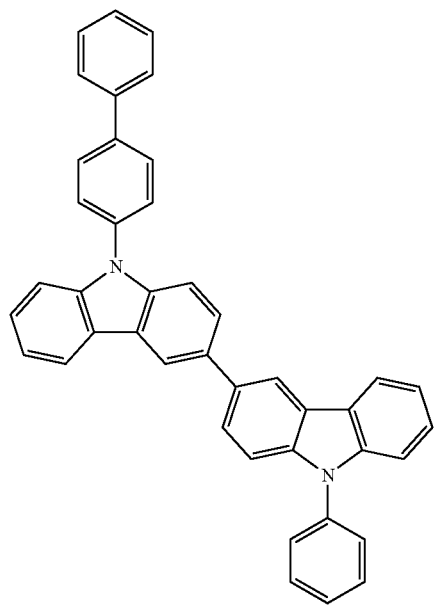
[B-137]
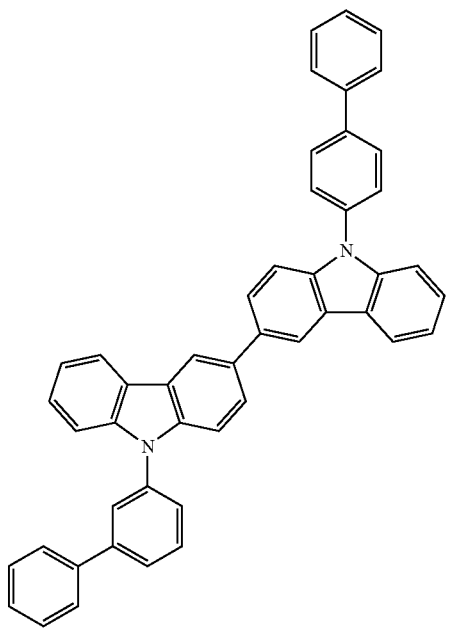

[B-138]
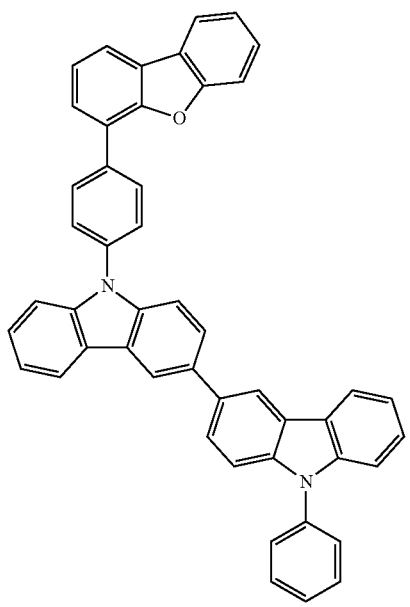
[B-139]
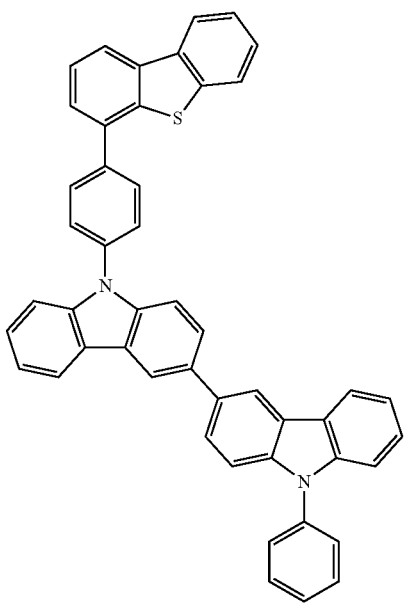
In an example embodiment, the second compound for an organic optoelectric device consisting of the combination of the moiety represented by Chemical Formula 3 and the moiety represented by Chemical Formula 4 may be represented by at least one of Chemical Formulae 3-I to 3-V.
[Chemical Formula 3-I]
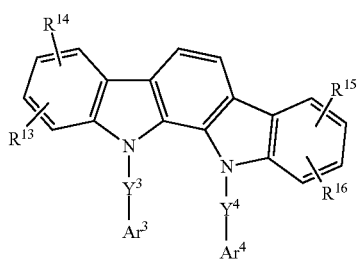
[Chemical Formula 3-II]
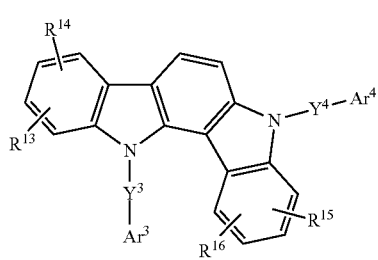
[Chemical Formula 3-III]
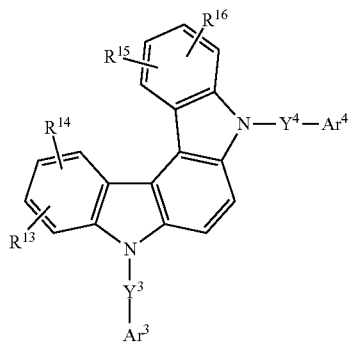
[Chemical Formula 3-IV]

[Chemical Formula 3-V]

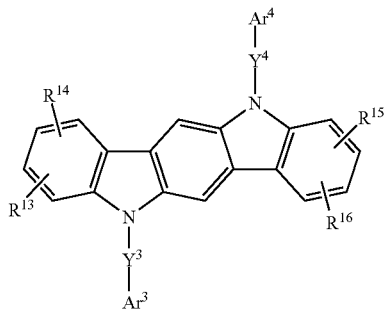

In Chemical Formulae 3-I to 3-V, $Y^3$, $Y^4$, $Ar^a$, $Ar^4$, and $R^{13}$ to $R^{16}$ are the same as described above.

In an example embodiment, $Y^3$ and $Y^4$ of Chemical Formulae 3-I to 3-V may be a single bond, a phenylene group, a biphenylene group, a pyridylene group, or a pyrimidinylene group.

In an example embodiment, $Ar^3$ and $Ar^4$ of Chemical Formulae 3-I to 3-V may be a substituted or unsubstituted phenyl group, a substituted or unsubstituted biphenyl group, a substituted or unsubstituted pyridyl group, a substituted or unsubstituted pyrimidinyl group, or a substituted or unsubstituted triazinyl group.

In an example embodiment, $R^{13}$ to $R^{16}$ of Chemical Formulae 3-I to 3-V may be hydrogen.

The second compound for an organic optoelectric device consisting of the combination of the moiety represented by Chemical Formula 3 and the moiety represented by Chemical Formula 4 may be for example compounds of Group 3, but is not limited thereto.

[Group 3]

[E-1]

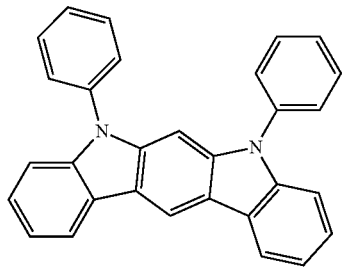

[E-2]

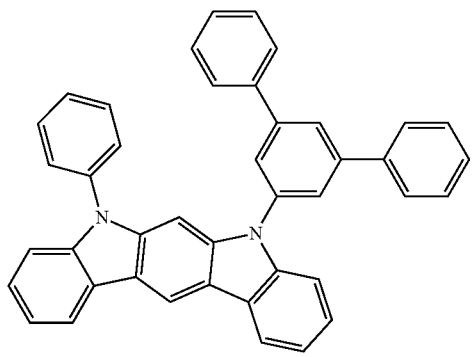

[E-3]

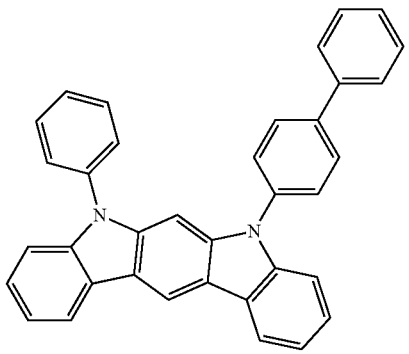

[E-4]

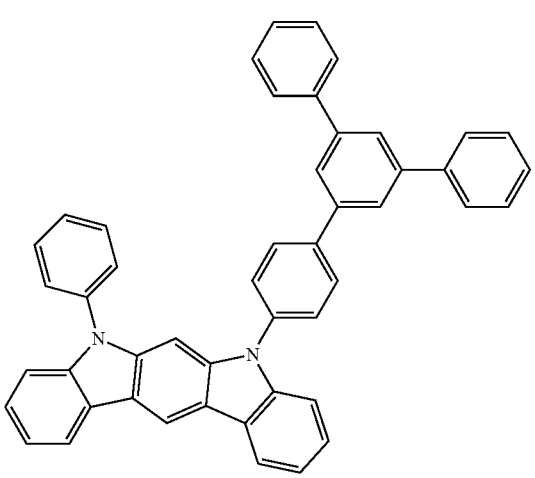

[E-5]

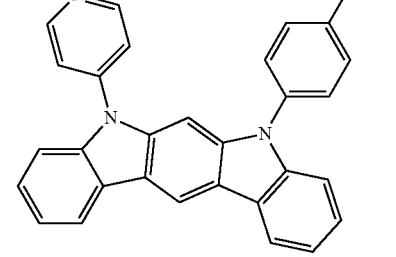

[E-6]

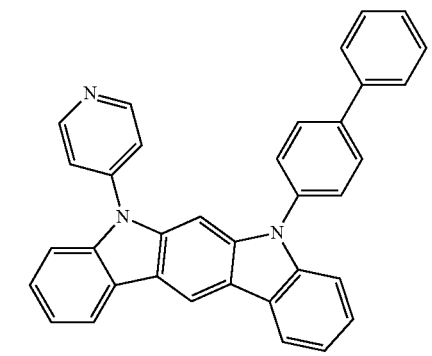

[E-7]
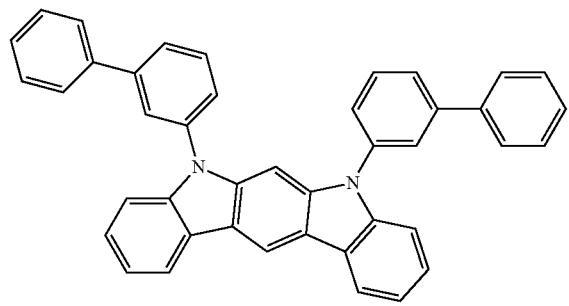
[E-8]
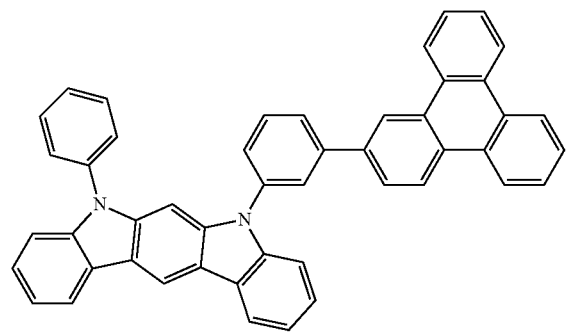
[E-9]
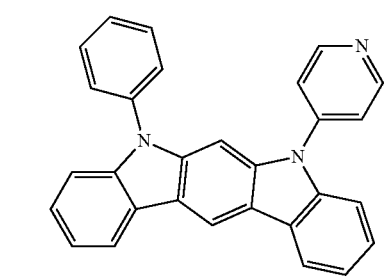
[E-10]
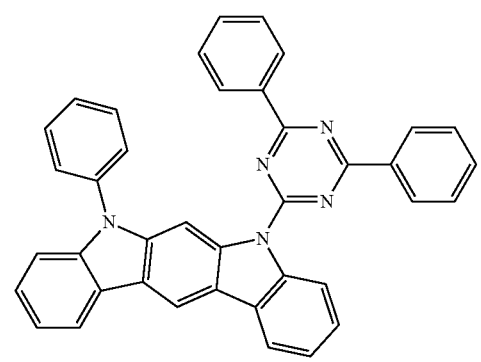
[E-11]
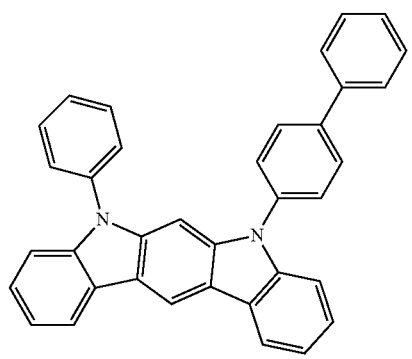
[E-12]
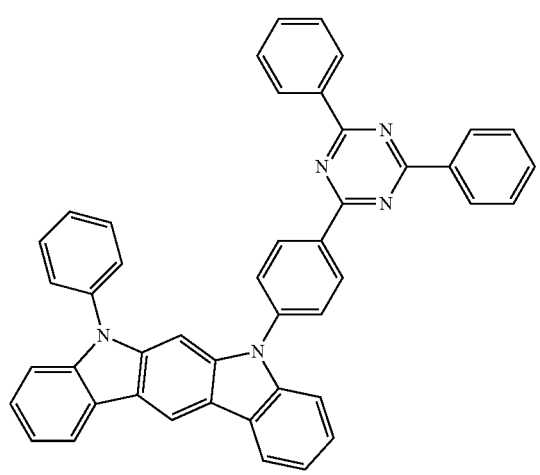
[E-13]
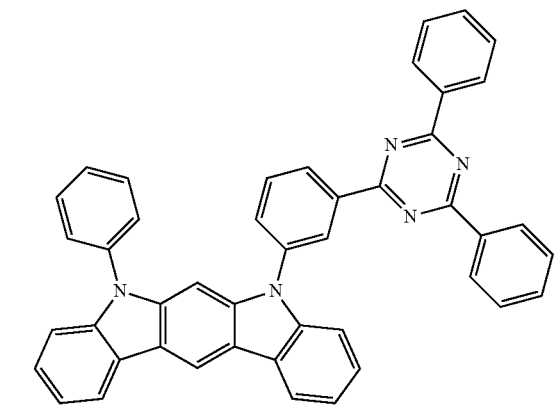
[E-14]
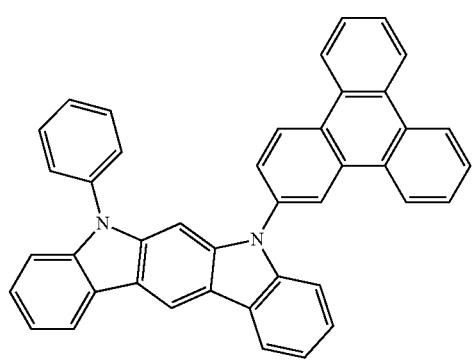

[E-15]
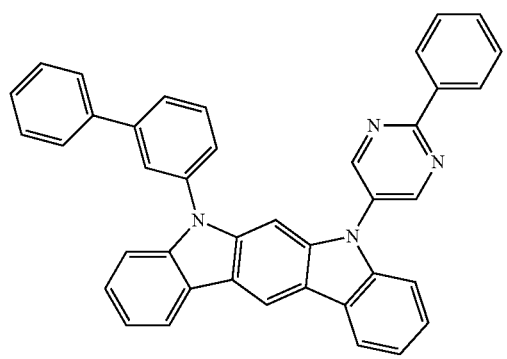
[E-16]
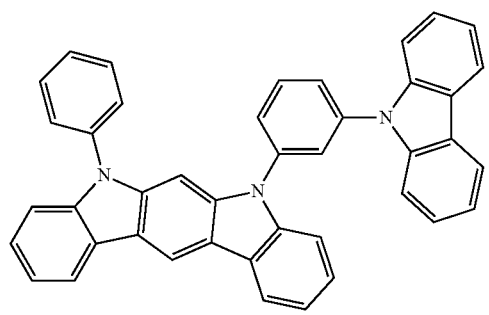
[E-17]
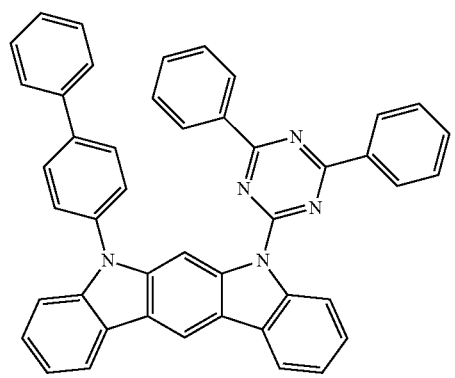
[E-18]
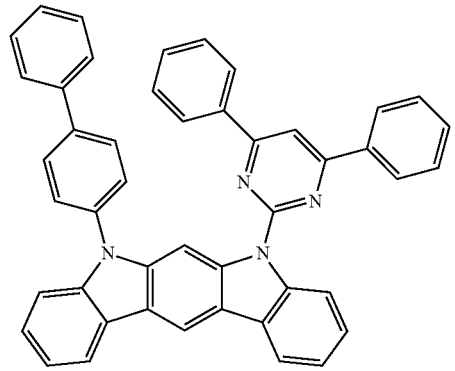
[E-19]
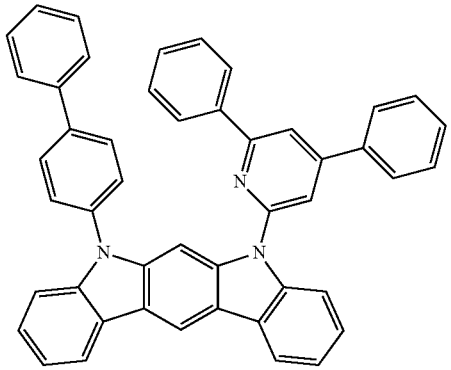
[E-20]
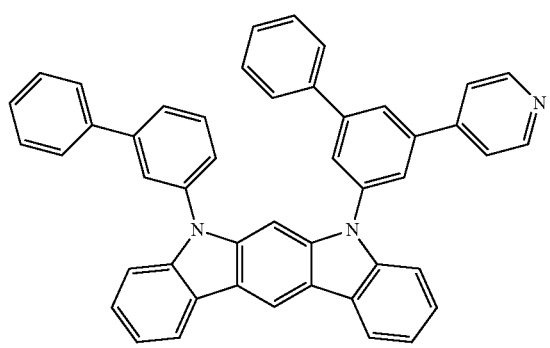
[E-21]
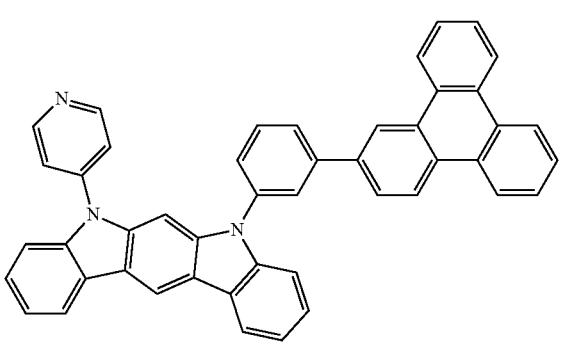
[E-22]
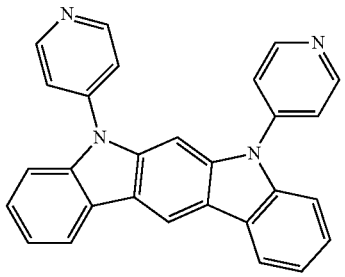
[E-23]
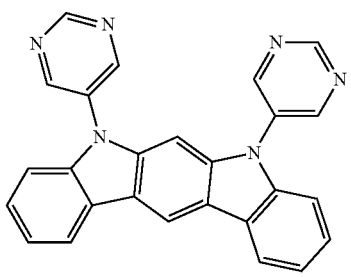

[E-24]
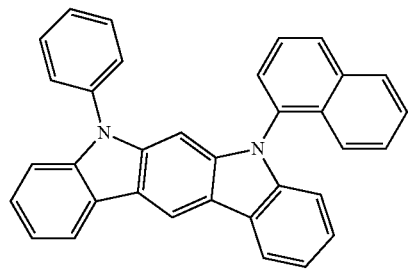
[E-28]
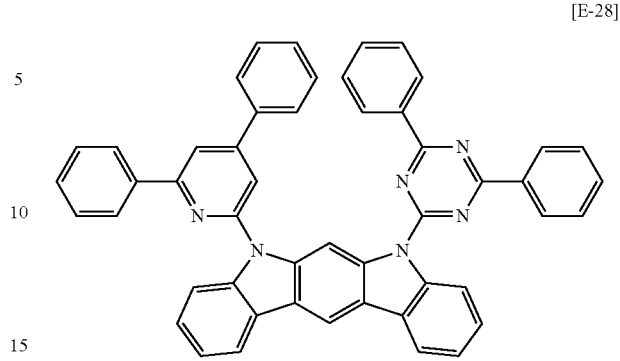
[E-25]
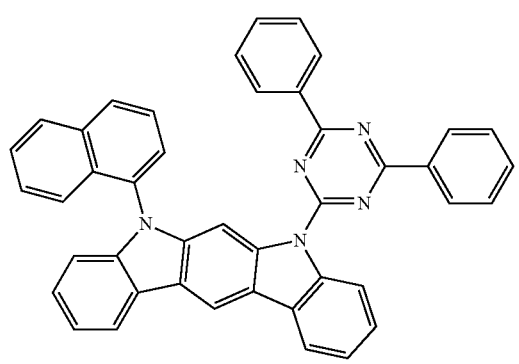
[E-29]
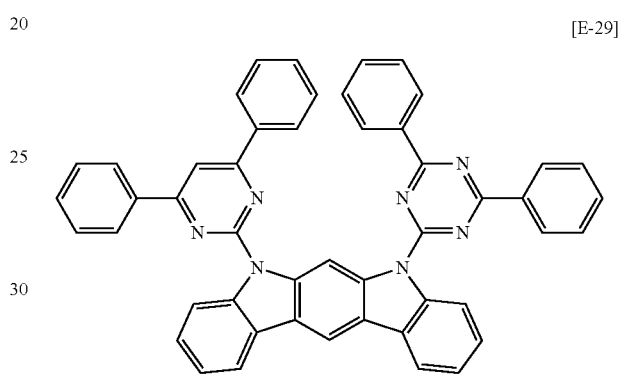
[E-26]
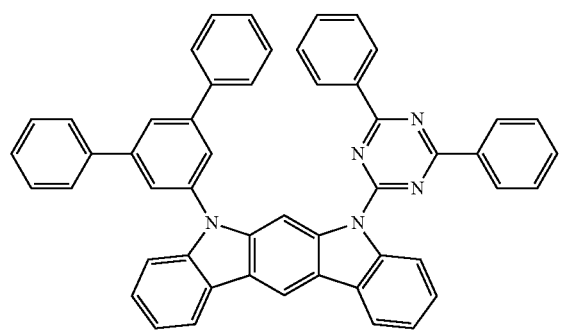
[E-30]
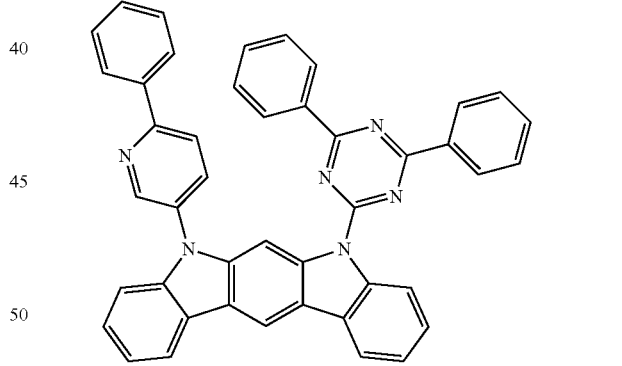
[E-27]
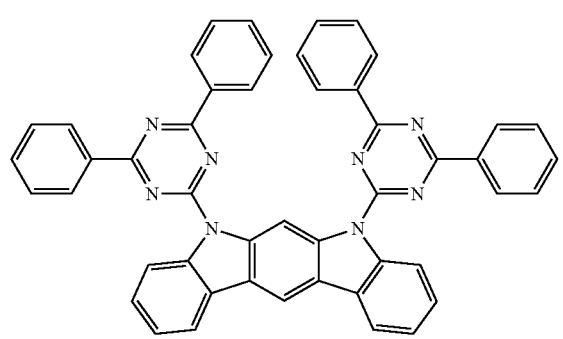
[E-31]
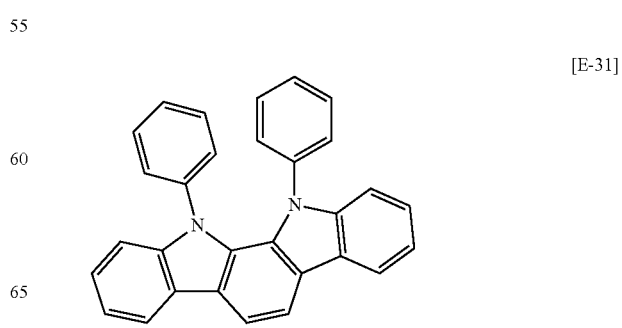

-continued
[E-32]
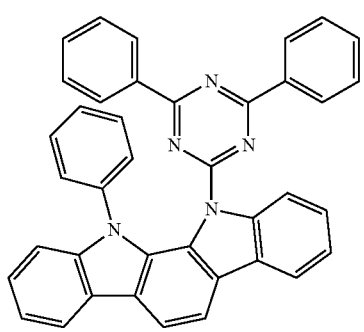
[E-33]
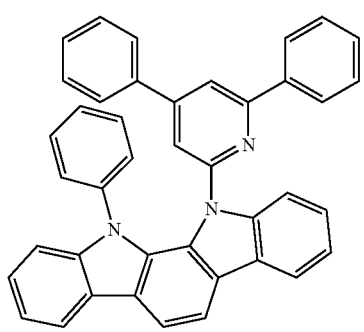
[E-34]
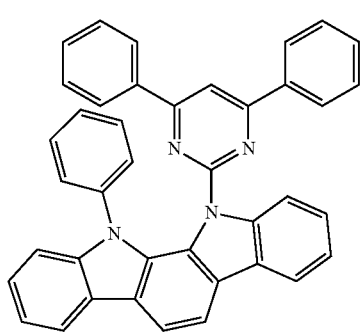
[E-35]
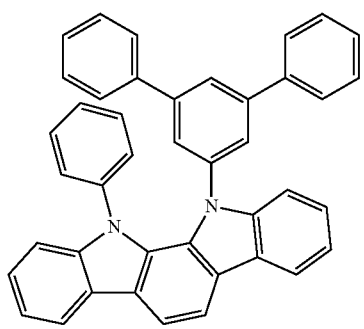
-continued
[E-36]
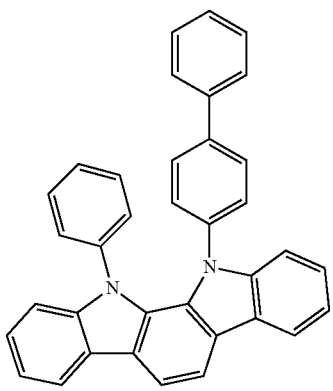
[E-37]
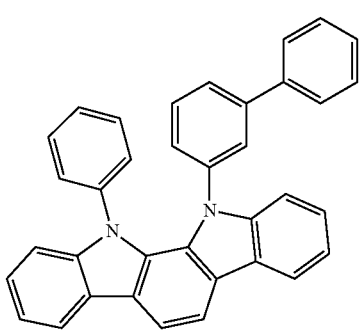
[E-38]
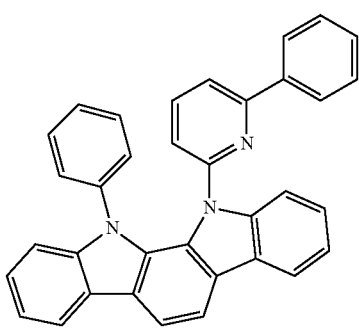
[E-39]
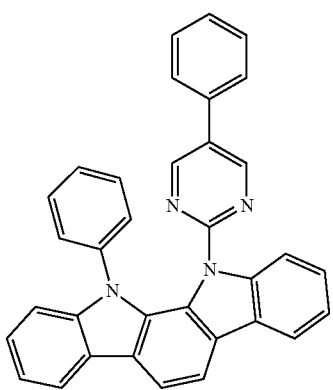

[E-40]

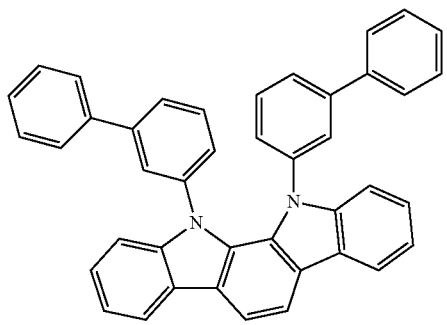

The second compound for an organic optoelectric device is used with the first compound for an organic optoelectric device in the light emitting layer and increases charge mobility and stability, and thereby luminous efficiency and life-span characteristics may be improved. In addition, a ratio of the second compound for an organic optoelectric device and the first compound for an organic optoelectric device may be adjusted and thereby charge mobility may be controlled.

When the composition of the present disclosure is used as a host, a combination ratio thereof may be different according to kinds and properties of a used dopant or when the composition of the present disclosure is used in an electron transport auxiliary layer, a combination ratio of compounds in the composition may be different according to kinds of a host and a dopant of an EML layer of an OLED device. For example, they may be included in a weight ratio of about 1:9 to about 9:1, specifically about 1:9 to about 8:2, about 1:9 to about 7:3, about 1:9 to about 6:4, or about 1:9 to about 5:5, or about 2:8 to about 8:2, about 2:8 to about 7:3, about 2:8 to about 6:4, or about 2:8 to about 5:5.

In addition, when the composition of the present disclosure is used as a host, the first compound for an organic optoelectric device and the second compound for an organic optoelectric device may be included in a weight ratio of about 1:9 to about 5:5, about 2:8 to about 5:5, or about 3:7 to about 5:5. For example, the first compound for an organic optoelectric device and the second compound for an organic optoelectric device may be included in a weight ratio of about 5:5. Within the ranges, efficiency and life-span may be simultaneously improved.

As one example of the composition for an organic optoelectric device, the first compound for an organic optoelectric device may be represented by Chemical Formula 1A and the second compound for an organic optoelectric device may be represented by Chemical Formula 1B or Chemical Formula 2.

For example, $R^{1a}$ and $R^{2a}$ of Chemical Formula 1A may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, at least one of $R^{1a}$ and $R^{2a}$ may be a substituted or unsubstituted pyrimidinyl group, a substituted or unsubstituted triazinyl group, a substituted or unsubstituted quinazolinyl group, a substituted or unsubstituted benzofuranpyrimidinyl group, or a substituted or unsubstituted benzothiophenepyrimidinyl group, $R^{1b}$ and $R^{2b}$ of Chemical Formula 1B may independently be a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, or a substituted or unsubstituted dibenzothiophenyl group, and Chemical Formula 2 may be represented by C-8 of Group III and *—$Y^1$—$Ar^1$ and *—$Y^2$—$Ar^2$ of Chemical Formula 2 may independently be selected from B-1 to B-3 of Group IV.

The composition may further include one or more organic compounds in addition to the first compound for an organic optoelectric device and the second compound for an organic optoelectric device.

The compound for an organic optoelectric device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectric device including the compound for an organic optoelectric device or the composition for an organic optoelectric device is described.

An organic optoelectric device according to another embodiment includes an anode and a cathode facing each other and at least one organic layer disposed between the anode and the cathode, wherein the organic layer includes the compound for an organic optoelectric device or the composition for an organic optoelectric device.

For example, the organic layer may include a light emitting layer and the light emitting layer may include the compound for an organic optoelectric device or the composition for an organic optoelectric device of the present disclosure.

Specifically, the compound for an organic optoelectric device or the composition for an organic optoelectric device may be included as a host, for example a red host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectric device or the composition for an organic optoelectric device.

The auxiliary layer may further include a hole transport auxiliary layer that is adjacent to the light emitting layer and the hole transport auxiliary layer may include the compound for an organic optoelectric device or the composition for an organic optoelectric device.

The organic optoelectric device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectric device is described referring to drawings.

Figure 2:
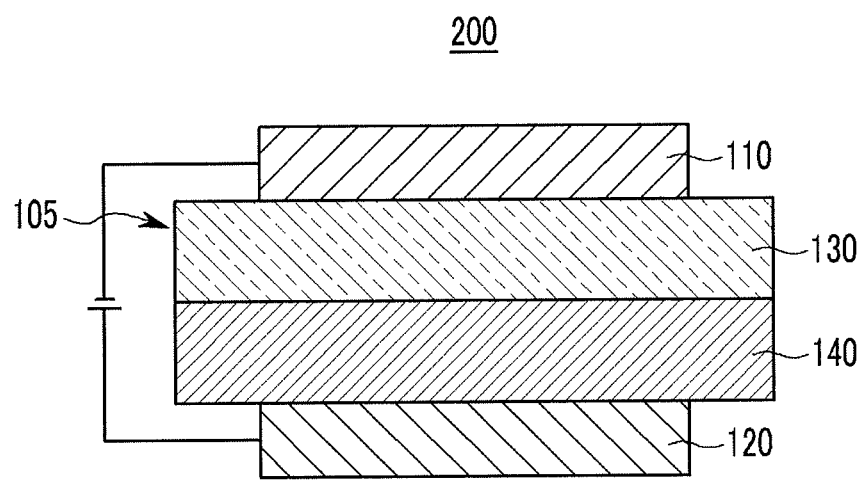

FIGS. 1 and 2 are cross-sectional views of an organic light emitting diode according to embodiments.

Referring to FIG. 1, an organic light emitting diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like, or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, LiO$_2$/Al, LiF/Ca, LiF/Al and BaF$_2$/Ca, but is not limited thereto.

The organic layer 105 includes a light emitting layer 130 including the compound or the composition for an organic optoelectric device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound or the composition for an organic optoelectric device of the present disclosure may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co., Ltd. or TCI Inc. as far as there in no particular comment or were synthesized by known methods.

(Preparation of Compound for Organic Optoelectric Device)

The compound as one specific examples of the present disclosure was synthesized through the following steps.

(First Compound for Organic Optoelectric Device)

Synthesis Example 1: Synthesis of Compound 2

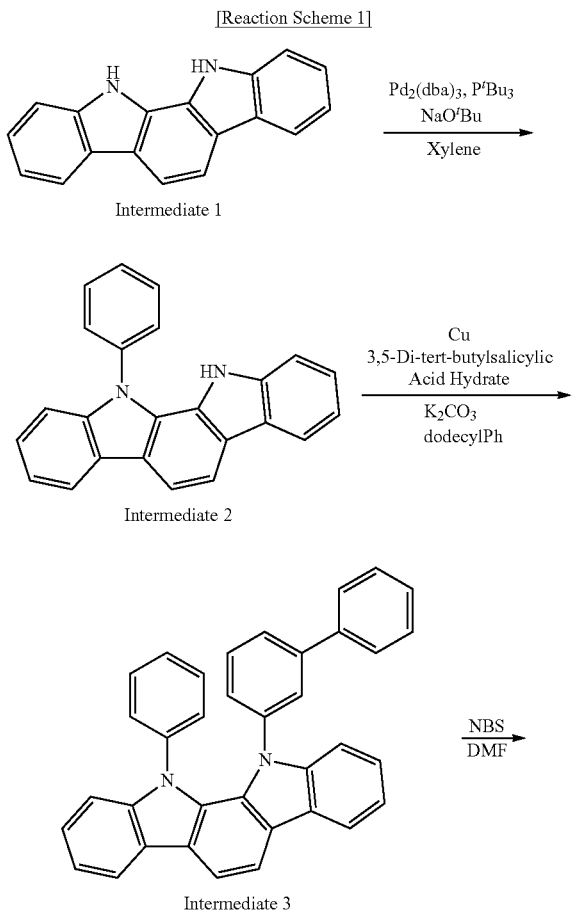

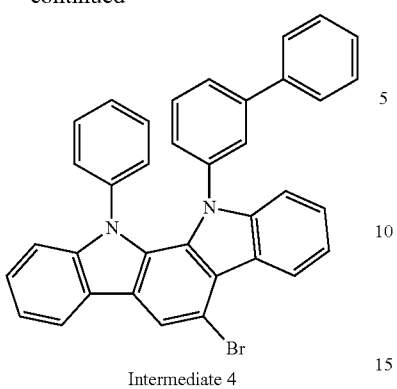

Intermediate 4

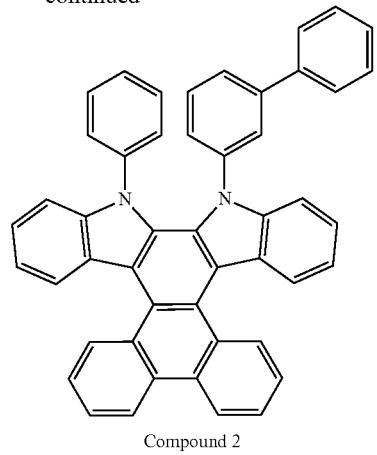

Compound 2

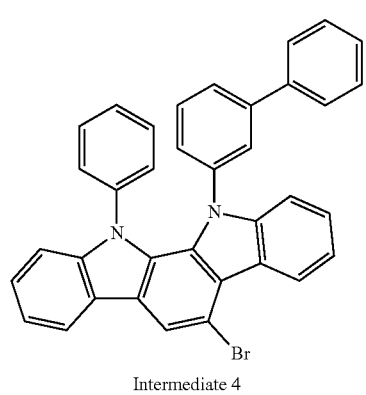

Intermediate 5

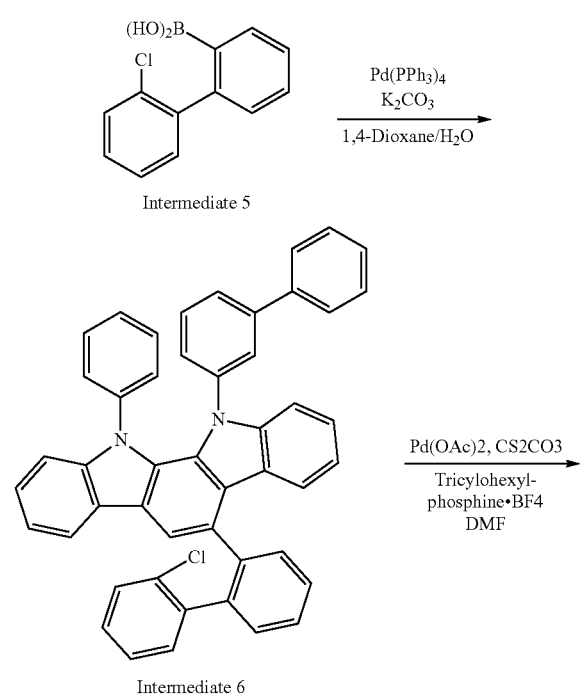

Intermediate 6

First Step: Synthesis of Intermediate 2

100.00 g (390.19 mmol) of Intermediate 1, 73.52 g, (468.23 mmol) of bromobenzene, 75.00 g (780.39 mmol) of sodium t-butoxide, 22.44 g (32.02 mmol) of tris(dibenzylideneacetone) dipalladium, and 31.58 g (50% in toluene) of tri t-butylphosphine were mixed with 1.5 L of xylene in a 3 L flask, and the mixture was heated and refluxed under a nitrogen flow for 24 hours. The obtained mixture was added to 4.5 L of methanol, and a solid crystallized therein was filtered, dissolved in monochlorobenzene, filtered with silica gel/Celite, and after removing an appropriate amount of an organic solvent, recrystallized with methanol to obtain 97.0 g of Intermediate 2 (a yield of 75%).

Second Step: Synthesis of Intermediate 3

20.00 g (60.17 mmol) of Intermediate 2, 16.83 g (72.20 mmol) of bromometabiphenyl, 0.77 g (12.03 mmol) of copper, 3.01 g (32.02 mmol) of 3,5-di-tert-butyl salicylic acid hydrate, and 12.47 g (90.25 mmol) of potassium carbonate were mixed with 200 ml of dodecylbenzene in a 500 mL flask, and the mixture was heated and refluxed under a nitrogen flow for 18 hours. The obtained mixture was added to 600 ml of methanol, and a solid crystallized therein was filtered, dissolved in monochlorobenzene, filtered with silica gel/Celite, and after removing an appropriate amount of an organic solvent, recrystallized with methanol to obtain 23.4.0 g of Intermediate 3 (a yield of 80%).

Third Step: Synthesis of Intermediate 4

23.0 g (47.46 mol) of Intermediate 3 was mixed with 230 ml of N,N-dimethylformamide in a 500 ml flask, and the mixture was internally cooled down to −10° C. The internal temperature was maintained at −10° C., while 9.29 g (52.21 mol) of N-bromosuccinimide was slowly added thereto. When a reaction was complete, a resultant obtained after removing a solvent was treated through column chromatography to obtain 17.4 g of Intermediate 4 (a yield of 65%).

Fourth Step: Synthesis of Intermediate 6

15.0 g (26.62 mmol) of Intermediate 4, 7.43 g (31.94 mmol) of Intermediate 5, 9.20 g (66.55 mmol) of potassium carbonate, and 0.92 g (0.8 mmol) of tetrakis(triphenylphosphine) palladium (0) were mixed with 80 mL of 1,4-dioxane and 40 mL of water in a 250 ml flask, and the mixture was heated at 100° C. under a nitrogen flow for 24 hours. An organic layer was separated therefrom and volatilized and then, added to 400 ml of methanol, and a solid crystallized therein was filtered, dissolved in monochlorobenzene, filtered with silica gel/Celite, and after removing an appropriate amount of an organic solvent, recrystallized with monochlorobenzene to obtain 11.9 g of Intermediate 6 (a yield of 67%).

Fifth Step: Synthesis of Compound 2

10.0 g (14.90 mmol) of Intermediate 6, 0.34 g (1.49 mmol) of palladium acetate, 14.57 g (44.71 mmol) of cesium carbonate, and 1.10 g (2.98 mmol) of tricyclohexylphosphine-tetrafluoroborate were mixed with 45 mL of N,N-dimethylacetamide in a 100 ml flask, and the mixture was heated under a nitrogen flow for 12 hours. When a reaction was complete, the resultant was added to 300 mL of water, and a solid crystallized therein was filtered, dissolved in dichlorobenzene, filtered with silica gel/Celite, and after removing an appropriate amount of an organic solvent, recrystallized with methanol to obtain Compound 2 (8.1 g, a yield of 87%). calcd. C48H30N2: C, 90.82; H, 4.76; N, 4.41; found: C, 90.82; H, 4.76; N, 4.41.

Synthesis Example 2: Synthesis of Compound 3

Compound 3 (6.5 g, a yield of 85%) was obtained according to the same method as Synthesis Example 1 except for using bromoparabiphenyl instead of the bromometabiphenyl used in Step 2 of Synthesis Example 1. calcd. C48H30N2: C, 90.82; H, 4.76; N, 4.41; found: C, 90.81; H, 4.76; N, 4.41.

Synthesis Example 3: Synthesis of Compound 5

Compound 5 (4.9 g, a yield of 80%) was obtained according to the same method as Synthesis Example 1 except for using bromometabiphenyl as the bromobenzene in the same moles as above instead of the bromobenzene used in Step 1 of Synthesis Example 1. calcd. C54H34N2: C, 91.24; H, 4.82; N, 3.94; found: C, 91.24; H, 4.82; N, 3.94.

Synthesis Example 4: Synthesis of Compound 6

Compound 6 (6.0 g, a yield of 83%) was obtained according to the same method as Synthesis Example 1 except for using bromoparabiphenyl instead of the bromobenzene used in Step 1 of Synthesis Example 1 and bromoparabiphenyl instead of bromometabiphenyl in Step 2 thereof. calcd. C54H34N2: C, 91.24; H, 4.82; N, 3.94; found: C, 91.24; H, 4.82; N, 3.94.

Synthesis Example 5: Synthesis of Compound 14

Compound 14 (10.3 g, a yield of 89%) was obtained according to the same method as Synthesis Example 1 except for using N-phenyl3-bromocarbazole instead of the bromometabiphenyl in Step 2 of Synthesis Example 1. calcd. C54H33N3: C, 89.60; H, 4.60; N, 5.81; found: C, 89.60; H, 4.60; N, 5.81.

Synthesis Example 6: Synthesis of Compound 26

Compound 26 (5.6 g, a yield of 87%) was obtained according to the same method as Synthesis Example 1 except for using N-phenyl3-bromoparabiphenyl instead of the bromobenzene in Step 1 of Synthesis Example 1 and 3-bromodibenzothiophene in Step 2 thereof. calcd. C54H32N2S: C, 87.54; H, 4.35; N, 3.78; S, 4.33; found: C, 87.54; H, 4.35; N, 3.78; S, 4.33.

Synthesis Example 7: Synthesis of Compound 27

Compound 27 (7.2 g, a yield of 85%) was obtained according to the same method as Synthesis Example 1 except for using N-phenyl3-bromoparabiphenyl instead of the bromobenzene in Step 1 of Synthesis Example 1 and 3-bromodibenzofuran in Step 2 thereof calcd. C54H32N2O: C, 89.48; H, 4.45; N, 3.86; 0, 2.21; found: C, 89.48; H, 4.45; N, 3.86; O, 2.20.

Synthesis Example 8: Synthesis of Compound 33

Compound 33 (8.7 g, a yield of 89%) was obtained according to the same method as Synthesis Example 1 except for using 3-(4-bromophenyl)dibenzofuran instead of the bromometabiphenyl in Step 2 of Synthesis Example 1. calcd. C54H32N2O: C, 89.48; H, 4.45; N, 3.86; O, 2.21; found: C, 89.48; H, 4.45; N, 3.86; O, 2.21.

Synthesis Example 9: Synthesis of Compound 34

Compound 34 (6.7 g, a yield of 84%) was obtained according to the same method as Synthesis Example 1 except for using 3-(4-bromophenyl)dibenzothiophene instead of the bromometabiphenyl in Step 2 of Synthesis Example 1. calcd. C54H32N2S: C, 87.54; H, 4.35; N, 3.78; S, 4.33; found: C, 87.54; H, 4.35; N, 3.78; S, 4.33.

Synthesis Example 10: Synthesis of Compound 41

Compound 41 (5.32 g, a yield of 75%) was obtained according to the same method as Synthesis Example 1 except for using 2-bromo-4-phenylquinazoline instead of the bromometabiphenyl in Step 2 of Synthesis Example 1. calcd. C50H30N4: C, 87.44; H, 4.40; N, 8.16; found: C, 87.44; H, 4.40; N, 8.16.

Synthesis Example 11: Synthesis of Compound 42

Compound 42 (5.21 g, a yield of 74%) was obtained according to the same method as Synthesis Example 1 except for using 4-(biphenyl-4-yl)-2-bromoquinazoline instead of the bromometabiphenyl in Step 2 of Synthesis Example 1. calcd. C56H34N4: C, 88.16; H, 4.49; N, 7.34; found: C, 88.16; H, 4.49; N, 7.34.

Synthesis Example 12: Synthesis of Compound 43

Compound 43 (5.62 g, a yield of 79%) was obtained according to the same method as Synthesis Example 1 except for using 4-(biphenyl-3-yl)-2-bromoquinazoline instead of the bromometabiphenyl in Step 2 of Synthesis Example 1. calcd. C56H34N4: C, 88.16; H, 4.49; N, 7.34; found: C, 88.16; H, 4.49; N, 7.34.

Synthesis Example 13: Synthesis of Compound 46

Compound 46 (5.14 g, a yield of 72%) was obtained according to the same method as Synthesis Example 1 except for using 4-(dibenzofuran-3-yl)-2-bromoquinazoline instead of the bromometabiphenyl in Step 2 of Synthesis

Example 1. calcd. C56H32N4O: C, 86.58; H, 4.15; N, 7.21; O, 2.06; found: C, 86.58; H, 4.15; N, 7.21; O, 2.06.

Synthesis Example 14: Synthesis of Compound 47

Compound 47 (5.02 g, a yield of 71%) was obtained according to the same method as Synthesis Example 1 except for using 4-(dibenzothiophene-3-yl)-2-bromoquinazoline instead of the bromometabiphenyl in Step 2 of Synthesis Example 1. calcd. C56H32N4S: C, 84.82; H, 4.07; N, 7.07; S, 4.04; found: C, 84.82; H, 4.07; N, 7.07; S, 4.04.

Synthesis Example 15: Synthesis of Compound 49

Compound 49 (5.49 g, a yield of 74%) was obtained according to the same method as Synthesis Example 1 except for using 2-bromo-4,6-diphenyl-1,3,5-triazine instead of the bromometabiphenyl in Step 2 of Synthesis Example 1. calcd. C51H31N5: C, 85.81; H, 4.38; N, 9.81; found: C, 85.81; H, 4.38; N, 9.81.

Synthesis Example 16: Synthesis of Compound 59

Compound 59 (5.11 g, a yield of 70%) was obtained according to the same method as Synthesis Example 1 except for using "benzo-2-chloro-4-phenyl-thieno[3,2-d]pyrimidine" (synthesized according to Synthesis Example 1 of Korean Patent Laid-Open Publication KR 2015-0083786A) instead of the bromometabiphenyl in Step 2 of Synthesis Example 1. calcd. C52H30N4S: C, 84.07; H, 4.07; N, 7.54; S, 4.32; found: C, 84.07; H, 4.07; N, 7.54; S, 4.32.

(Synthesis of Second Compound for Organic Optoelectric Device)

Synthesis Example 17: Synthesis of Compound B-130

[Reaction Scheme 2]

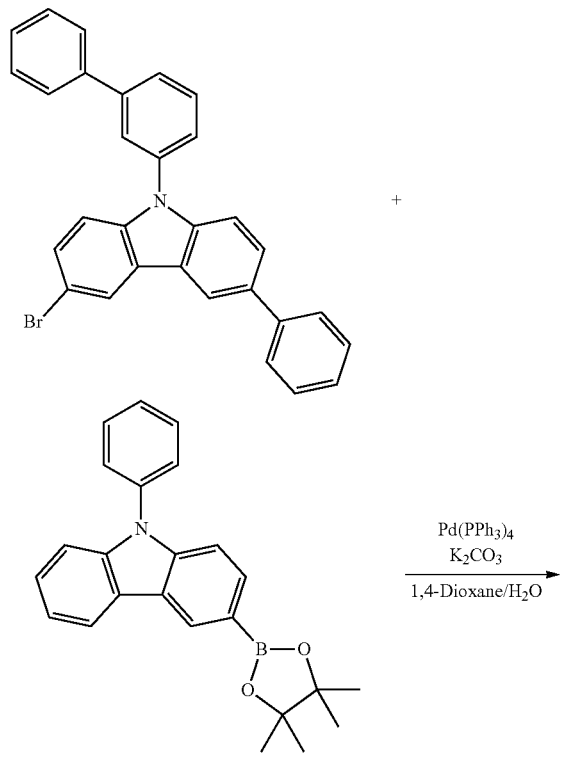

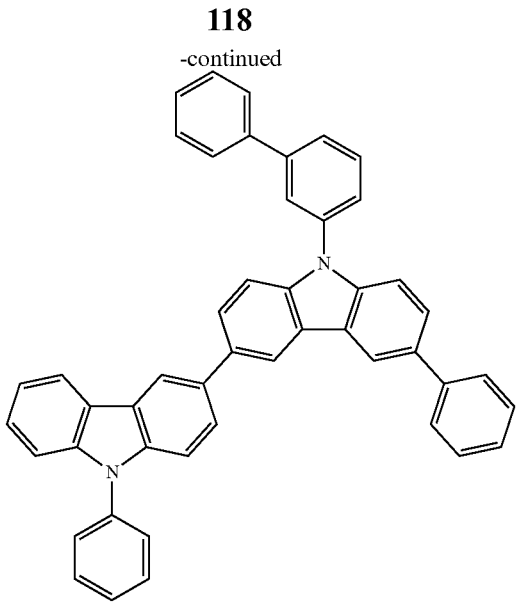

Compound B-130

20.00 g (42.16 mmol) of 3-bromo-6-phenyl-N-metabiphenylcarbazole, 17.12 g (46.38 mmol) of N-phenylcarbazole-3-boronic ester, and 175 mL of tetrahydrofuran and toluene (1:1) and 75 mL of a 2M-potassium carbonate aqueous solution under a nitrogen atmosphere in a 500 mL round-bottomed flask equipped with a stirrer, 1.46 g (1.26 mmol) of tetrakistriphenyl phosphine palladium (0) was added thereto, and the mixture was heated and refluxed under a nitrogen flow for 12 hours. When a reaction was complete, the reactant was poured into methanol, and a solid produced therein was filtered and then, sufficiently washed with water and methanol and dried. The obtained resulting material was heated with 700 mL of chlorobenzene and dissolved therein, and the solution was filtered with silica gel, and after completely removing the solvent, a solid obtained therefrom was heated with 400 mL of chlorobenzene and dissolved therein and then, recrystallized to obtain 18.52 g of Compound B-130 (a yield of 69%). calcd. $C_{42}H_{32}N_2$: C, 90.54; H, 5.07; N, 4.40; found: C, 90.54; H, 5.07; N, 4.40.

Manufacture of Organic Light Emitting Diode (I) (Light Emitting Layer Device-Single Host)

Example 1

An organic light emitting diode was manufactured by using Compound 41 obtained in Synthesis Example 10 as a host and $(piq)_2Ir(acac)$ as a dopant.

As for an anode, 1000 Å-thick ITO was used, and as for a cathode, 1000 Å-thick aluminum was used. Specifically, illustrating a method of manufacturing the organic light emitting diode, the anode is manufactured by cutting an ITO glass substrate having 15 Ω/cm² of a sheet resistance into a size of 50 mm×50 mm×0.7 mm, ultrasonic wave-cleaning them in each acetone, isopropyl alcohol, and pure water for 15 minutes respectively, and UV ozone cleaning them for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of $650\times10^{-7}$ Pa at a deposition rate of 0.1 to 0.3 nm/s. Subsequently, a 300 Å-thick light emitting layer was formed by using Compound 41 of Synthesis Example 3 under the same vacuum deposition condition, and a phosphorescent dopant of (piq)$_2$Ir(acac) was simultaneously deposited. Herein, the phosphorescent dopant was deposited to be 3 wt % based on 100 wt % of a total weight of the light emitting layer by adjusting the deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 200 Å-thick electron transport layer was formed by depositing Alq3 under the same vacuum deposition condition. On the electron transport layer, a cathode was formed by sequentially depositing LiF and Al to manufacture an organic light emitting diode.

A structure of the organic light emitting diode was ITO/NPB (80 nm)/EML (Compound 41 (97 wt %)+(piq)$_2$Ir(acac) (3 wt %), 30 nm)/Balq (5 nm)/Alq3 (20 nm)/LiF (1 nm)/Al (100 nm).

Examples 2 to 7

Organic light emitting diodes according to Examples 2 to 7 were respectively manufactured according to the same method as Example 1 except for using each of Compounds 42, 43, 46, 47, and 59 instead of Compound 41 as a host for forming a light emitting layer.

Comparative Example

An organic light emitting diode according to Comparative Example 1 was manufactured according to the same method as Example 1 except for using a compound of Comparative Structure Example 1 instead of Compound 41 as a host for forming a light emitting layer.

A result of comparing simulation data of Compound of the present disclosure with the compound of Comparative Structure Example 1 is shown in Table 1.

Comparative Structure Example 1

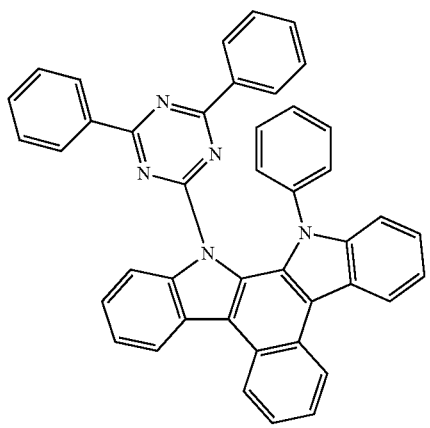

TABLE 1

|  | HOMO (eV) | LUMO (eV) | T1 (eV) | S1 (eV) |
|---|---|---|---|---|
| Comparative Structure Example 1 | −5.112 | −1.938 | 2.364 | 2.715 |
| Compound 49 | −5.062 | −1.945 | 2.425 | 2.631 |

Referring to Table 1, Compound 49 showed a more shallow HOMO Level than that of Comparative Structure Example 1. The reason is that the HOMO level of Compound 49 is closer to that of a dopant than that of Comparative Structure Example 1, and thus holes may be more injected. Accordingly, Compound 49 may have a better balance between holes and electrons and thus have a fast driving voltage and show high efficiency, long life-span device characteristics.

Evaluation Example 1: Characteristics Evaluation (I) of Organic Light Emitting Diode Luminous efficiency and life-span characteristics of each organic light emitting diode according to Examples 1 to 7 and Comparative Example 1 were evaluated.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000 A), while the voltages of the organic light emitting diodes were increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Driving Voltage

A driving voltage of each diode was measured using a current-voltage meter (Keithley 2400) at 15 mA/cm$^2$.

TABLE 2

| No. | Compounds | Dopant | Driving voltage (V) | Current efficiency (cd/A) | Color (EL color) |
|---|---|---|---|---|---|
| Example 1 | 41 | (piq)$_2$Ir(acac) | 4.4 | 20.2 | red |
| Example 2 | 42 | (piq)$_2$Ir(acac) | 4.1 | 20.7 | red |
| Example 3 | 43 | (piq)$_2$Ir(acac) | 4.2 | 20.5 | red |
| Example 4 | 46 | (piq)$_2$Ir(acac) | 4.1 | 20.7 | red |
| Example 5 | 47 | (piq)$_2$Ir(acac) | 4.2 | 20.6 | red |
| Example 6 | 49 | (piq)$_2$Ir(acac) | 4.3 | 20.5 | red |
| Example 7 | 59 | (piq)$_2$Ir(acac) | 4.5 | 20.6 | red |
| Comparative Example 1 | Comparative Structure Example 1 | (piq)$_2$Ir(acac) | 5.6 | 17.3 | red |

Referring to Table 2, the organic light emitting diodes of Examples 1 to 7 of the present disclosure showed a low driving voltage and high efficiency compared with that of Comparative Example 1.

Accordingly, the compound according to the present disclosure have excellent charge the characteristics and well overlapping with an absorption spectrum of the dopant as a phosphorescent host material and thus may improve performance such as an efficiency increase and a driving voltage decrease and exhibit maximized capability as an OLED material.

Manufacture of Organic Light Emitting Diode (II) (Light Emitting Layer Device-Mixed Host)

Example 8

An organic light emitting diode was manufactured according to the same method as Example 1 except for forming a 400 Å-thick light emitting layer by codepositing $(piq)_2Ir(acac)$ (a dopant), Compound 41 (a first host), and Compound B-137 (a second host) in a weight ratio of 3:48.5:48.5 on a hole transport layer.

Examples 9 to 14

Organic light emitting diodes according to Examples 9 to 14 were respectively manufactured according to the same method as Example 8 except for using each of Compounds 42, 43, 46, 47, 49, and 59 instead of Compound 41 as the first host to form the light emitting layer.

Example 15

An organic light emitting diode was manufactured according to the same method as Example 1 except for codepositing $(piq)_2Ir(acac)$ (dopant), Compound 42 (a first host), and Compound B-99 (a second host) in a weight ratio of 3:48.5:48.5 to form a 400 Å-thick light emitting layer on a hole transport layer.

Examples 16 to 19

Organic light emitting diodes according to Examples 16 to 19 were manufactured according to the same method as Example 15 except for using each of Compounds 3, 6, 14, and 27 as the second host instead of Compound B-99 to form a light emitting layer.

Example 20

An organic light emitting diode was manufactured according to the same method as Example 1 except for codepositing $(piq)_2Ir(acac)$ (a dopant), Compound 46 (a first host), and Compound B-99 (a second host) in a weight ratio of 3:48.5:48.5 on a hole transport layer to form a 400 Å-thick light emitting layer.

Examples 21 to 24

Organic light emitting diodes according to Examples 21 to 24 were respectively manufactured according to the same method as Example 20 except for using each of Compounds 3, 6, 14, and 27 as a second host instead of Compound B-98 to form a light emitting layer.

Evaluation Example 2: Characteristics Evaluation (II) of Organic Light Emitting Diode A driving voltage, efficiency, luminance, and a life-span of each organic light emitting diode according to Examples 8 to 24 and Comparative Example 1 were measured by supplying power from a current voltage meter (Kethley SMU 236) and using a luminance meter, PR650 Spectroscan Source Measurement Unit (Photo Research Inc.), and the results are shown in Table 3. A $T_{95}$ life-span was evaluated as time (hr) taken until 95% of luminance relative to 100% of initial luminance was obtained.

TABLE 3

| Examples | First host | Second host | Driving Voltage (V) | Current efficiency (cd/A) | Color (EL color) |
|---|---|---|---|---|---|
| 8 | 41 | B-137 | 4.2 | 21.2 | red |
| 9 | 42 | B-137 | 3.9 | 21.4 | red |
| 10 | 43 | B-137 | 4.0 | 21.3 | red |
| 11 | 46 | B-137 | 3.8 | 21.5 | red |
| 12 | 47 | B-137 | 4.0 | 21.3 | red |
| 13 | 49 | B-137 | 4.2 | 21.2 | red |
| 14 | 59 | B-137 | 4.2 | 21.4 | red |
| 15 | 42 | B-99 | 3.8 | 21.7 | red |
| 16 | 42 | 3 | 4.2 | 21.3 | red |
| 17 | 42 | 6 | 4.0 | 21.6 | red |
| 18 | 42 | 14 | 3.9 | 21.6 | red |
| 19 | 42 | 27 | 3.9 | 21.5 | red |
| 20 | 46 | B-99 | 3.7 | 21.7 | red |
| 21 | 46 | 3 | 4.1 | 21.4 | red |
| 22 | 46 | 6 | 3.9 | 21.5 | red |
| 23 | 46 | 14 | 3.8 | 21.6 | red |
| 24 | 46 | 27 | 3.8 | 21.6 | red |
| Comparative Example 1 | Comparative Structure Example 1 | | 5.6 | 17.3 | red |

Referring to Table 3, the organic light emitting diodes of Examples 8 to 24 using both first and second host materials which were the compounds of the present disclosure showed low driving voltages or high efficiency.

DESCRIPTION OF SYMBOLS 100, 200: organic light emitting diode

105: organic layer

110: cathode

120: anode

130: light emitting layer

140: hole auxiliary layer

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectric device represented by Chemical Formula 1:

[Chemical Formula 1]

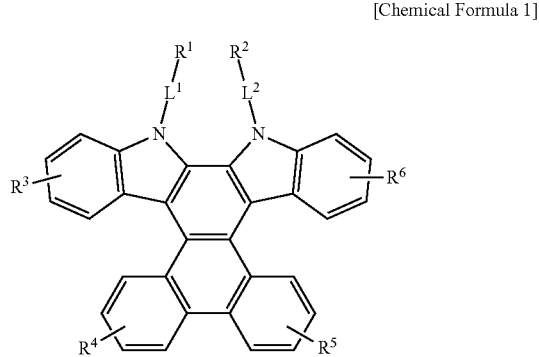

[Chemical Formula 1A]

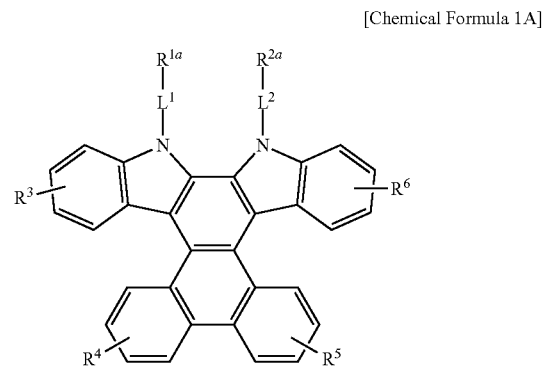

wherein, in Chemical Formula 1, $R^1$ and $R^2$ are independently a substituted or unsubstituted C6 to C30 aryl group, a substituted or unsubstituted C2 to C30 heterocyclic group, or a combination thereof, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, $L^1$ and $L^2$ are independently a single bond, a substituted or unsubstituted C6 to C30 arylene group, a substituted or unsubstituted C2 to C30 heteroarylene group, or a combination thereof, and the "substituted" refers to replacement of at least one hydrogen by deuterium, a C1 to C4 alkyl group, a C6 to C18 aryl group, or a C2 to C18 heteroaryl group.

2. The compound for an organic optoelectric device as claimed in claim 1, wherein $R^1$ and $R^2$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group(naphthyridinyl), a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, or a substituted or unsubstituted benzonaphthothiophenyl group, or a substituted or unsubstituted benzoquinazolinyl group.

3. The compound for an organic optoelectric device as claimed in claim 1, wherein the compound is represented by Chemical Formula 1A:

wherein, in Chemical Formula 1A, $R^{1a}$ and $R^{2a}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, a substituted or unsubstituted benzothiophenepyrimidinyl group, a substituted or unsubstituted benzonaphthofuranyl group, a substituted or unsubstituted benzonaphthothiophenyl group, or a substituted or unsubstituted benzoquinazolinyl group, at least one of $R^{1a}$ and $R^{2a}$ is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted phenanthrolinyl group, a substituted or unsubstituted benzofuranpyrimidinyl group, or a substituted or unsubstituted benzoquinazolinyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

4. The compound for an organic optoelectric device as claimed in claim 1, wherein the compound is represented by Chemical Formula 1B:

[Chemical Formula 1B]

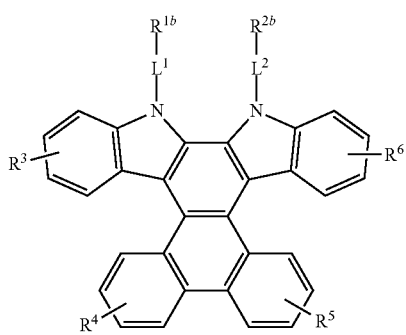

wherein, in Chemical Formula 1B, $R^{1b}$ and $R^{2b}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

5. The compound for an organic optoelectric device as claimed in claim 1, wherein $R^1$ and $R^2$ are independently selected from substituents of Group I:

[Group I]

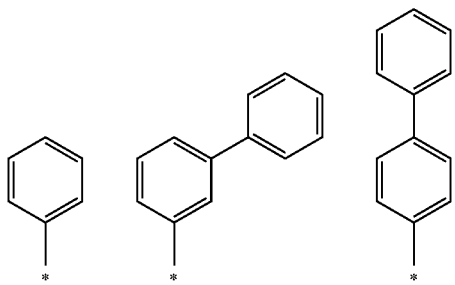

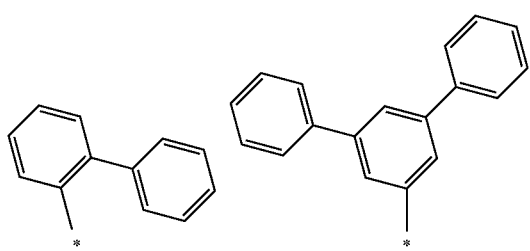

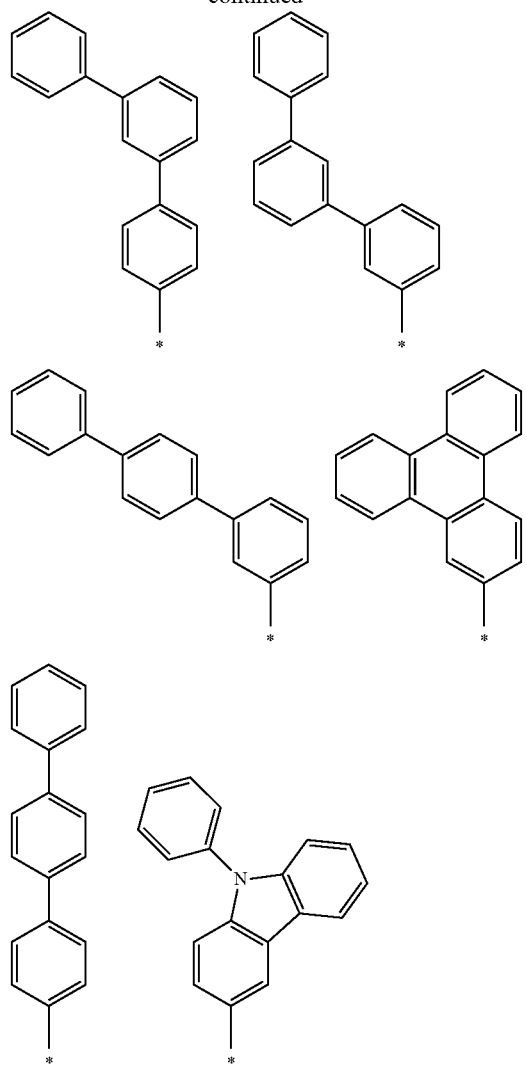

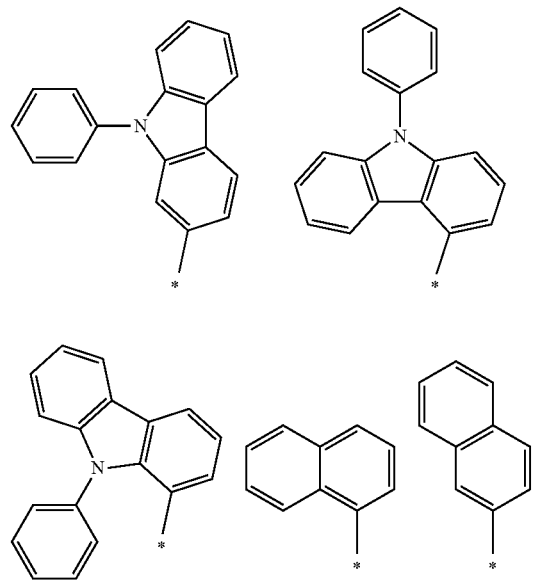

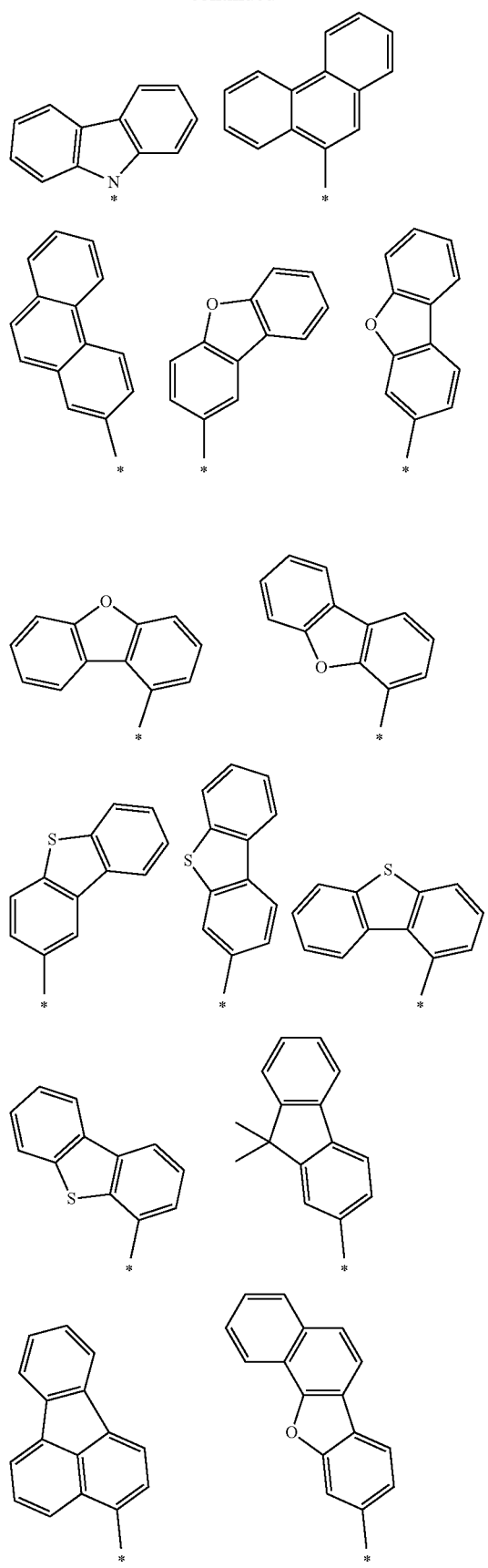
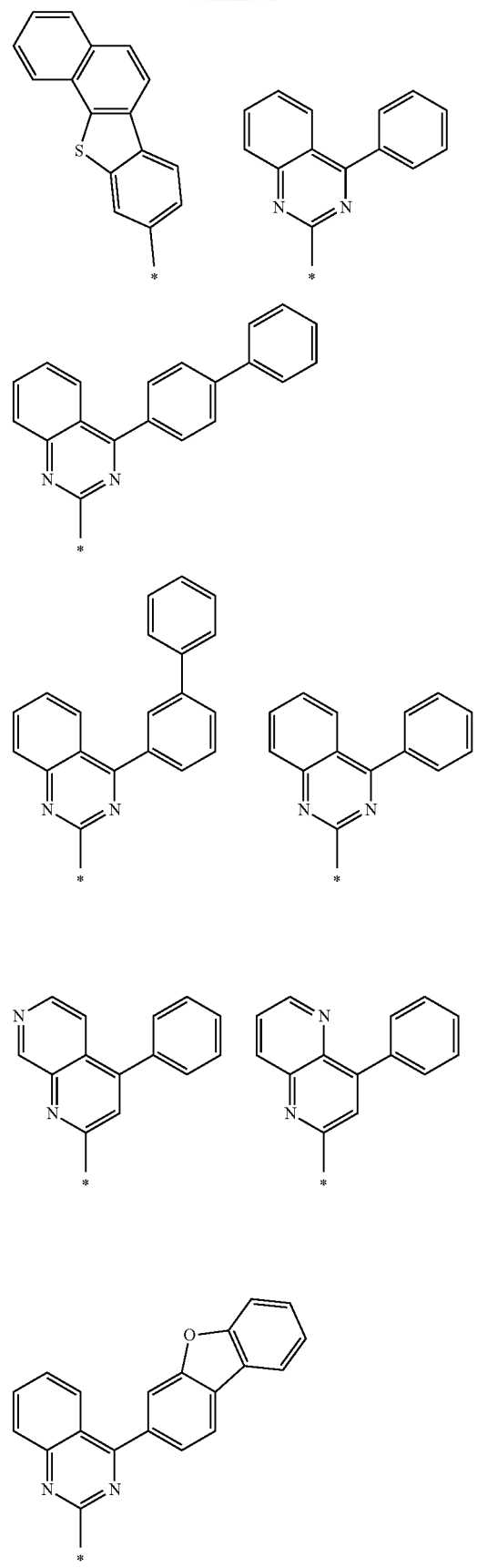

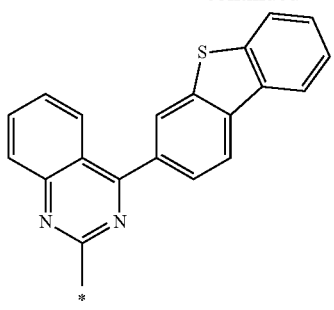
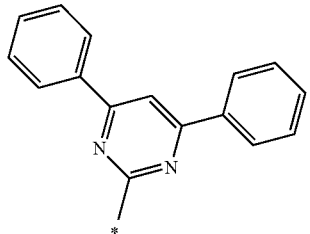
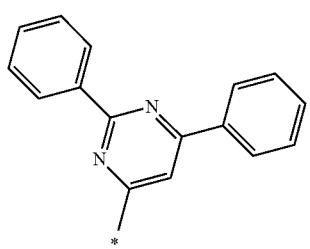
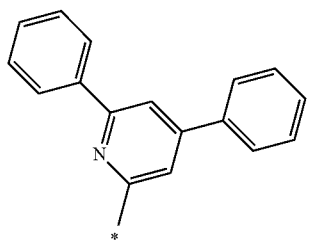
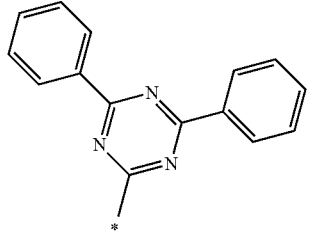
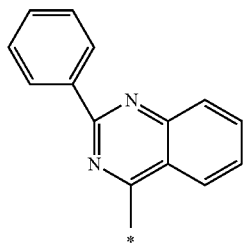
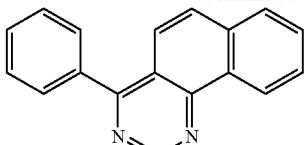
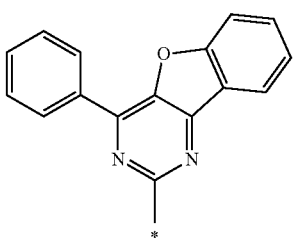
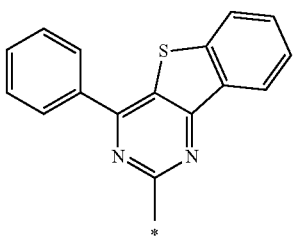
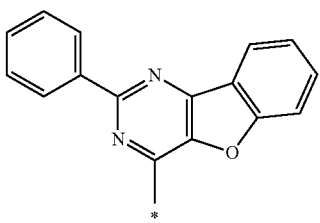
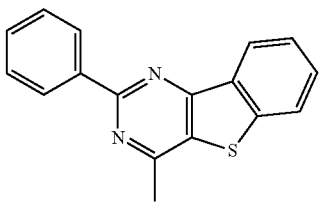
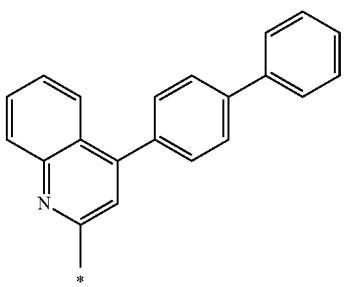
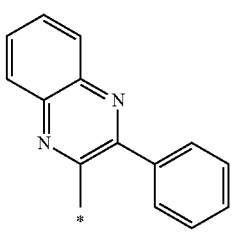
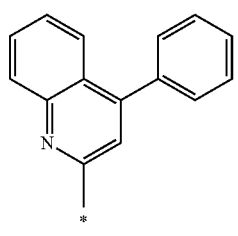

wherein, in Group I, * is a binding site with an adjacent atom.

6. The compound for an organic optoelectric device as claimed in claim 1, wherein $L^1$ and $L^2$ are independently a single bond, a substituted or unsubstituted phenylene group, a substituted or unsubstituted biphenylene group, or a substituted or unsubstituted terphenylene group.

7. The compound for an organic optoelectric device as claimed in claim 1, wherein:
$R^1$ and $R^2$ are independently a substituted or unsubstituted phenyl group, a substituted or unsubstituted p-biphenyl group, a substituted or unsubstituted m-biphenyl group, a substituted or unsubstituted carbazolyl group, a substituted or unsubstituted dibenzofuranyl group, a substituted or unsubstituted dibenzothiophenyl group, a substituted or unsubstituted pyrimidinyl group, a substituted or unsubstituted triazinyl group, a substituted or unsubstituted quinazolinyl group, or a substituted or unsubstituted benzofuranpyrimidinyl group, or a substituted or unsubstituted benzothiophenepyrimidinyl group,
$L^1$ and $L^2$ are independently a single bond, or phenylene group,
$R^3$ to $R^6$ are all hydrogen, and
the "substituted" refers to replacement of at least one hydrogen by deuterium, a C1 to C4 alkyl group, a phenyl group, a biphenyl group, a dibenzofuranyl group, or a dibenzothiophenyl group.

8. The compound for an organic optoelectric device as claimed in claim 1, wherein the compound is selected from compounds of Group 1:

[Group 1]

1

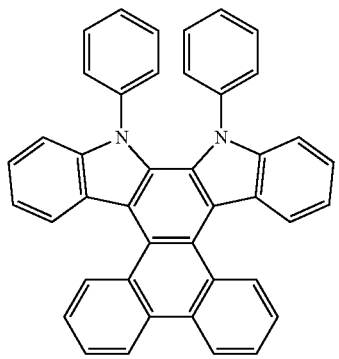

2

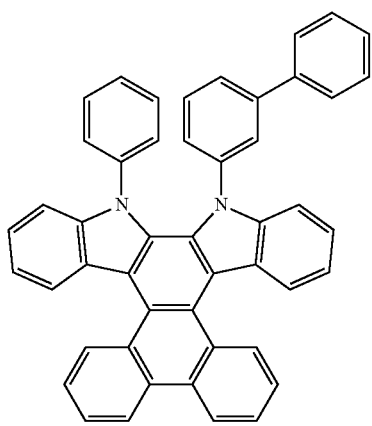

-continued

3

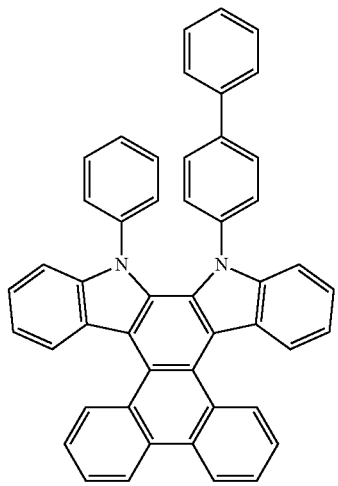

4

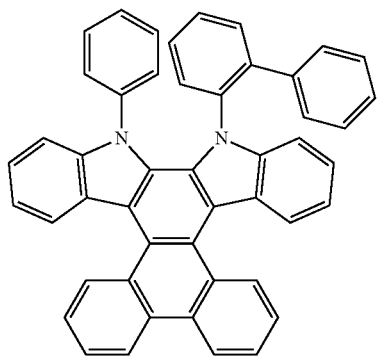

5

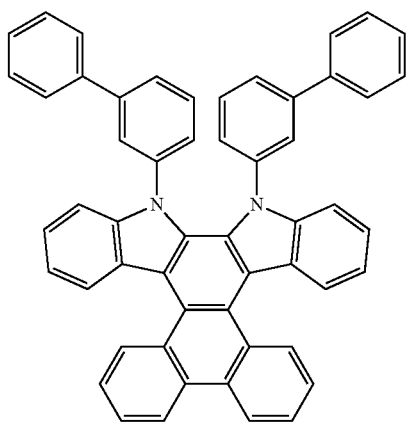

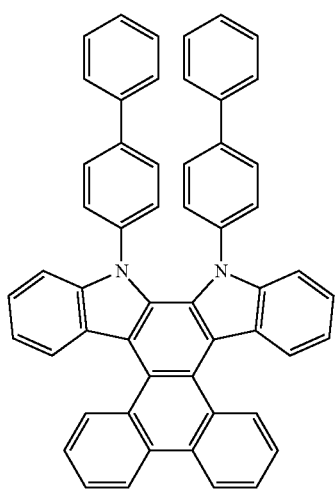
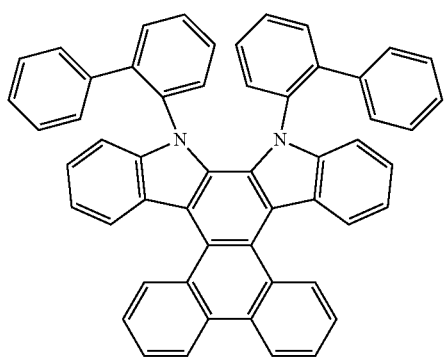
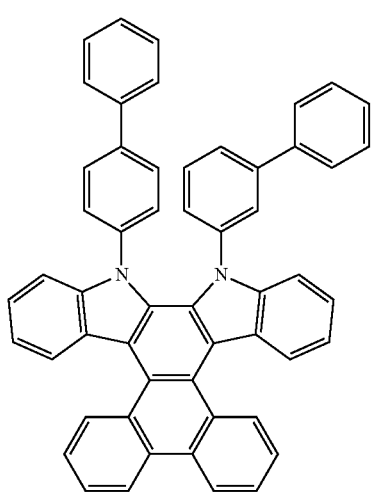
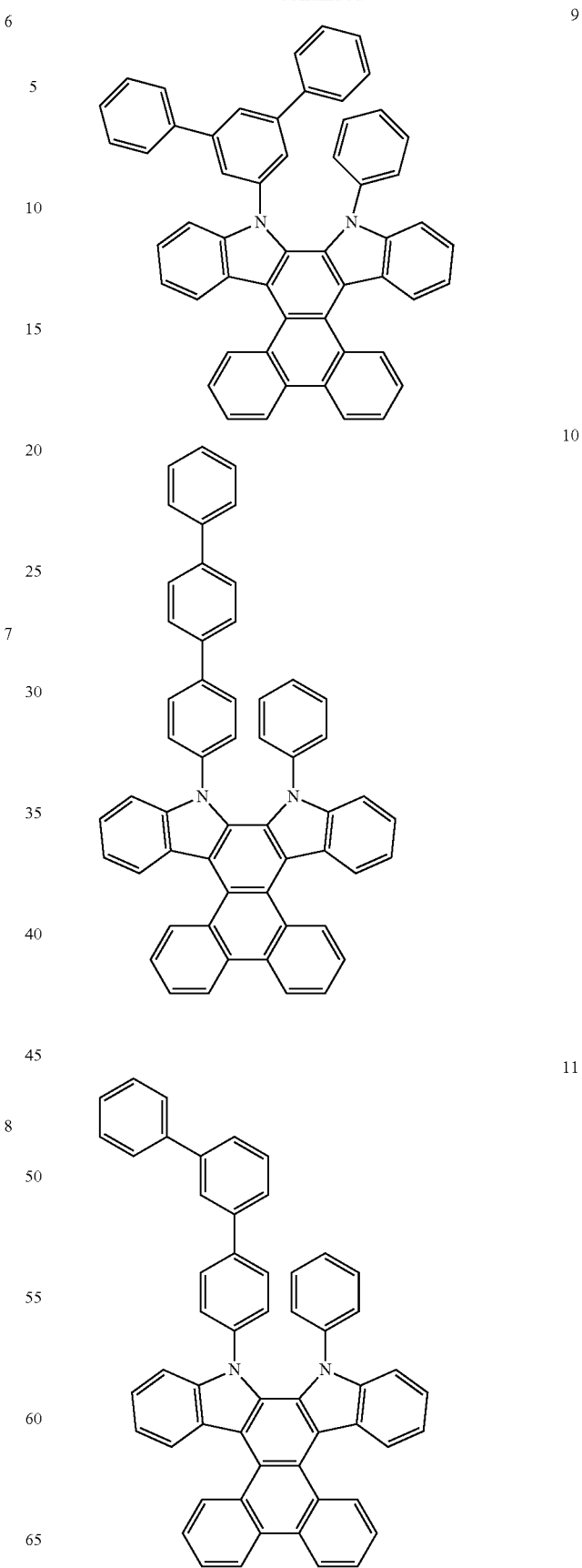

12
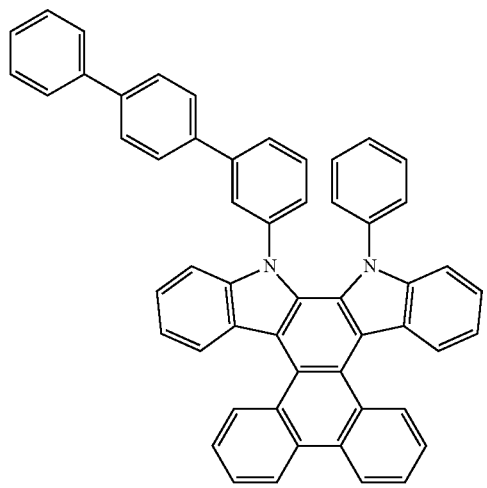
13
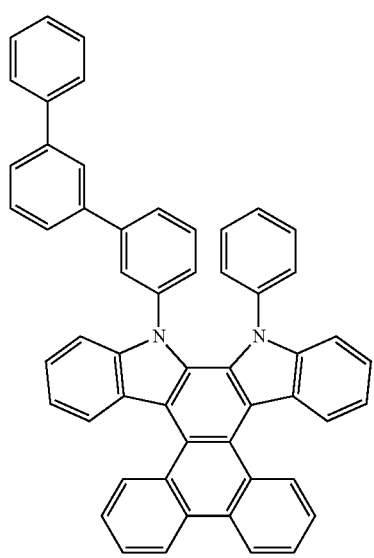
14
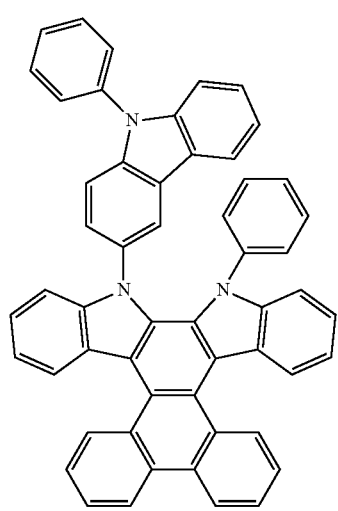
15
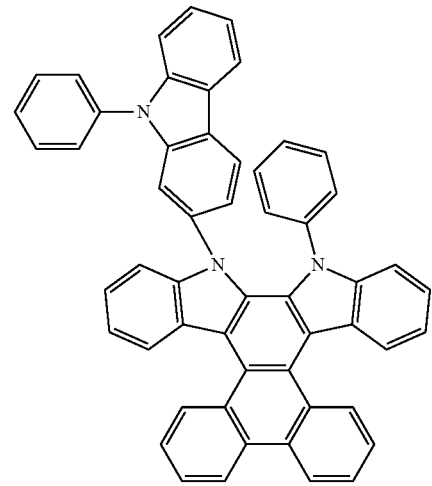
16
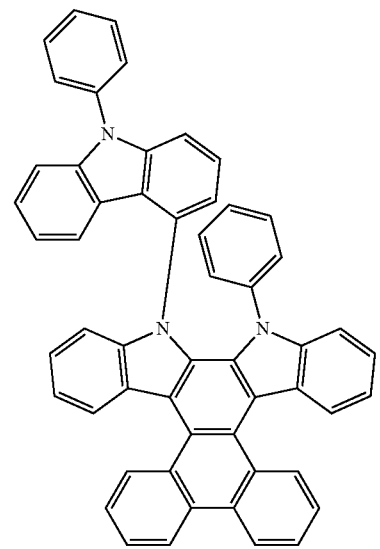
17
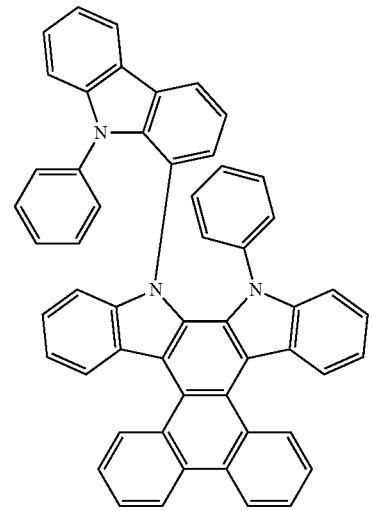

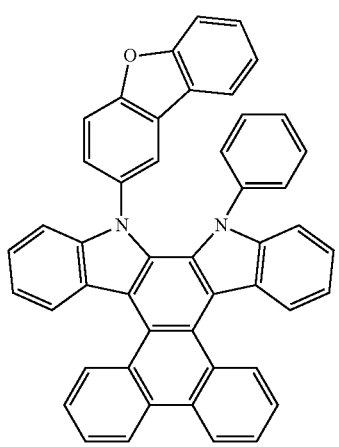
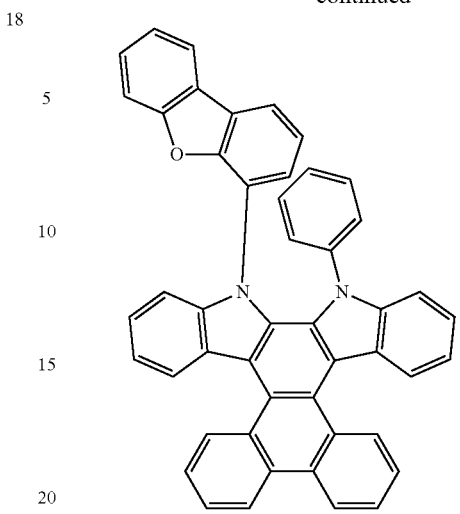
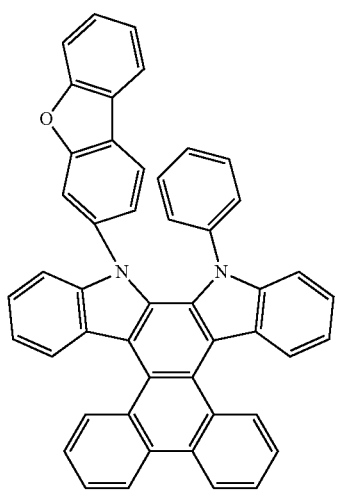
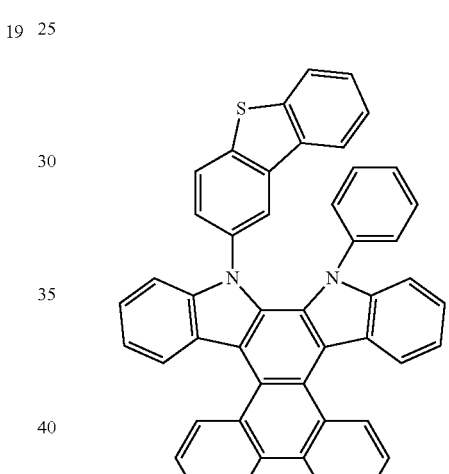
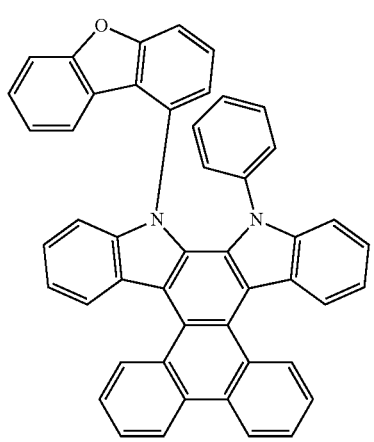
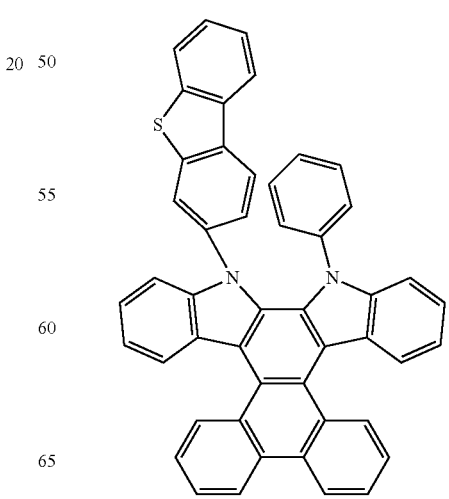

24
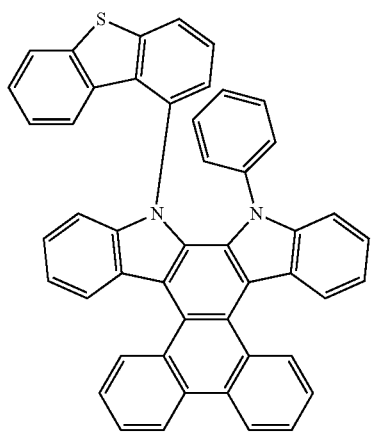
5
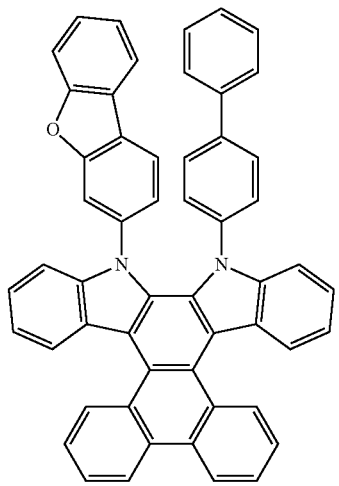
27
10
15
20
25
25
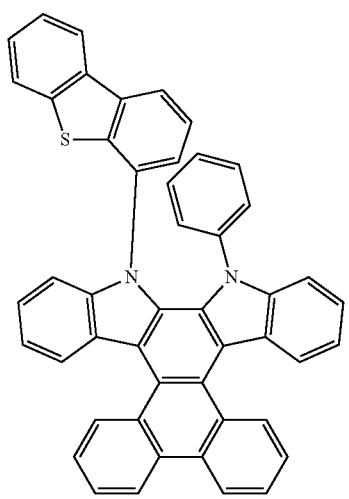
30
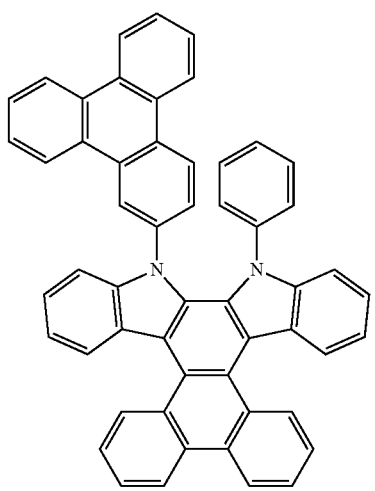
28
35
40
45
26
50
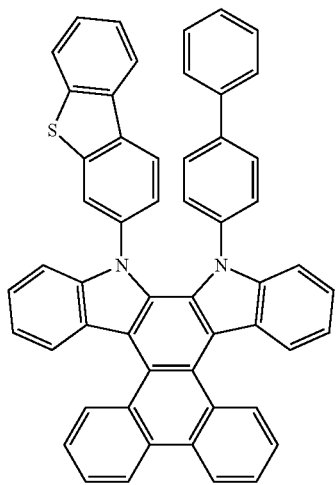
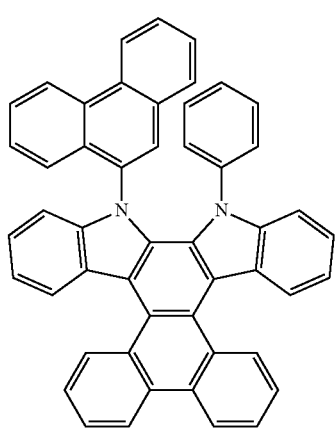
29
55
60
65

141
-continued
30
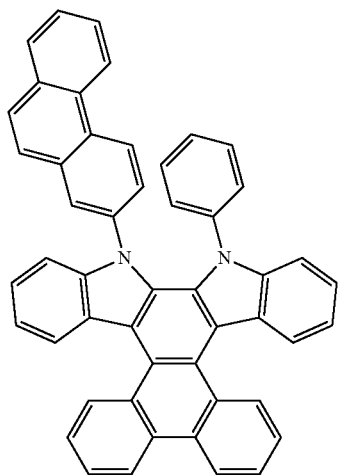
31
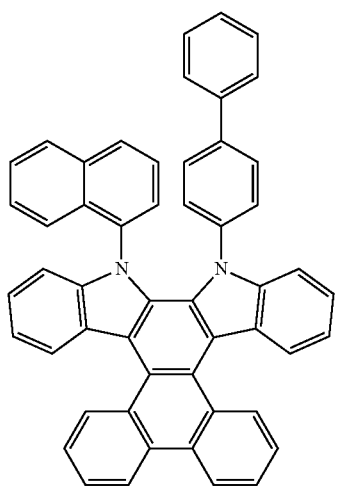
32
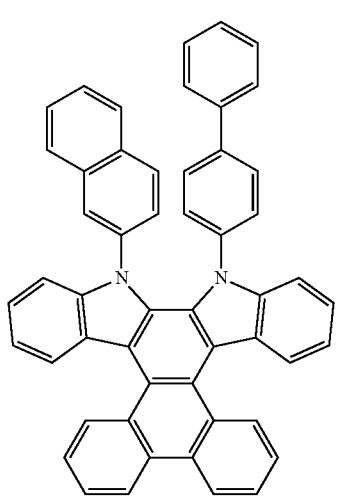
142
-continued
33
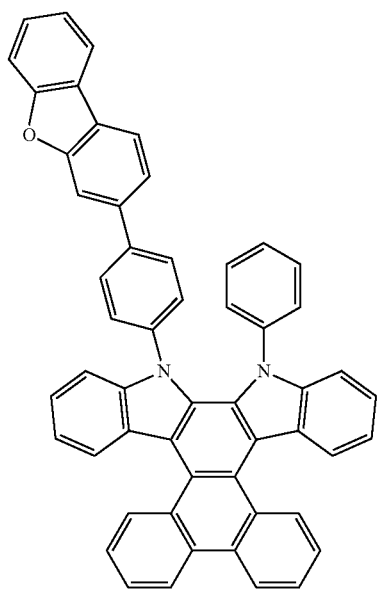
34
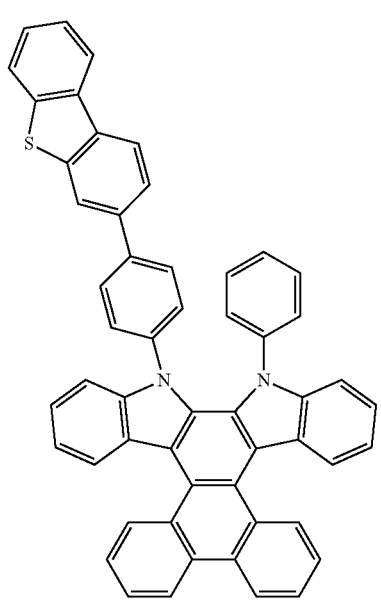
35
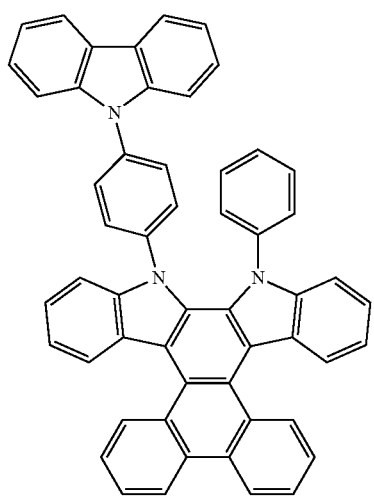

36
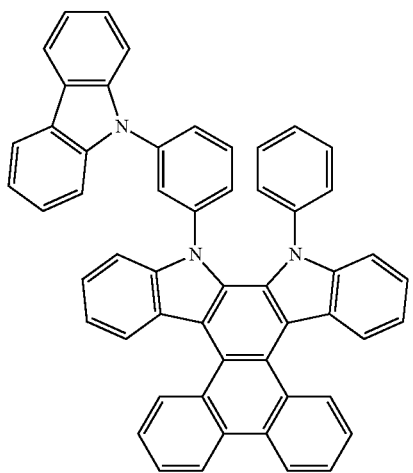
37
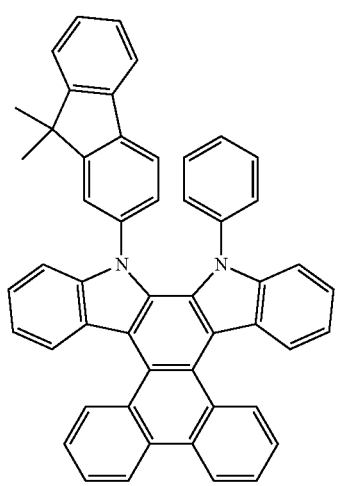
38
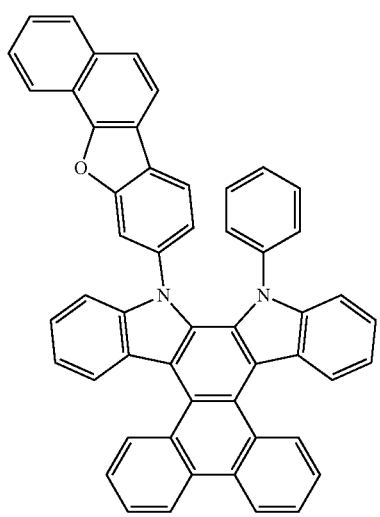
39
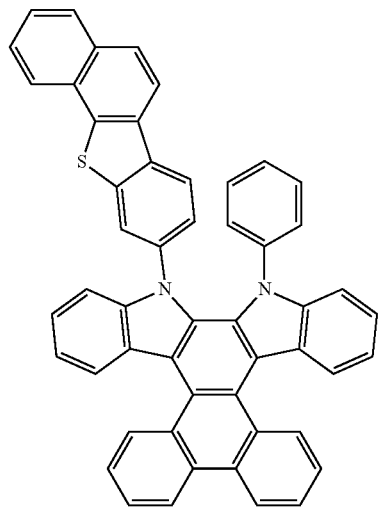
40
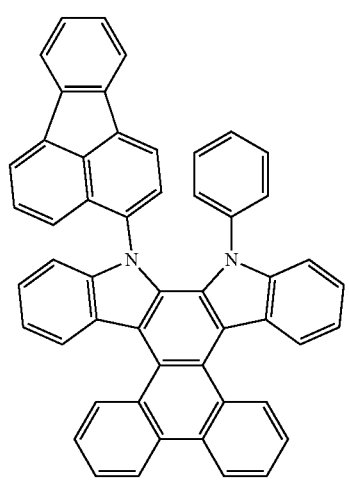
41
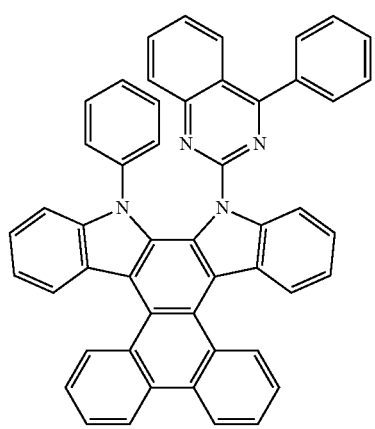

-continued
42
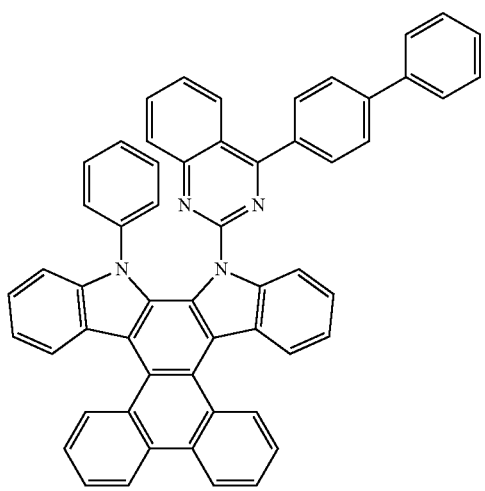
43
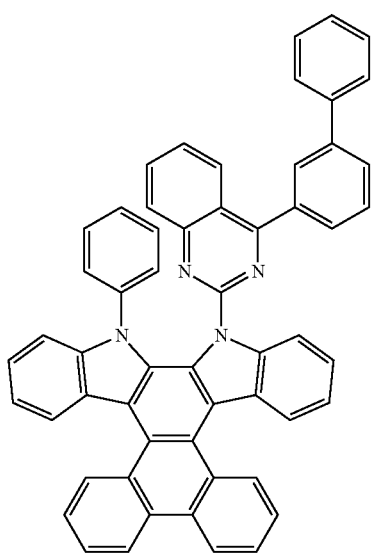
43
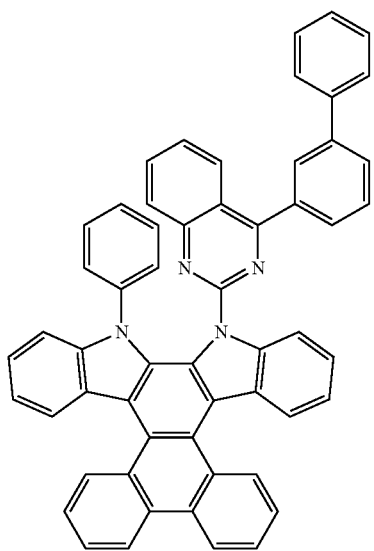
-continued
44
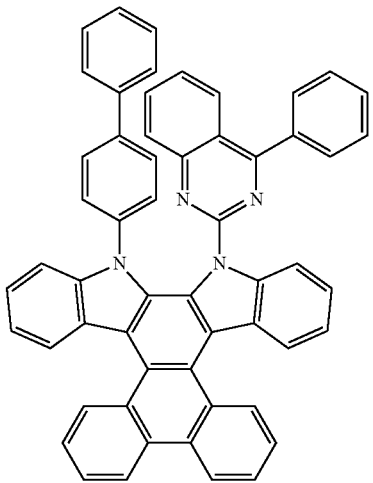
45
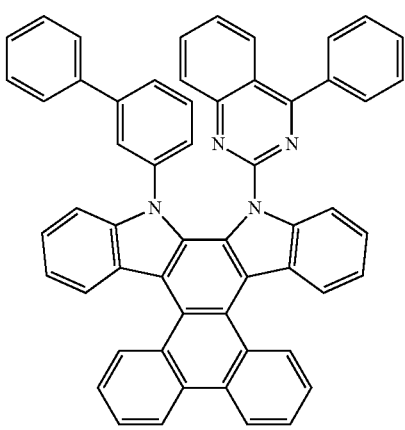
46
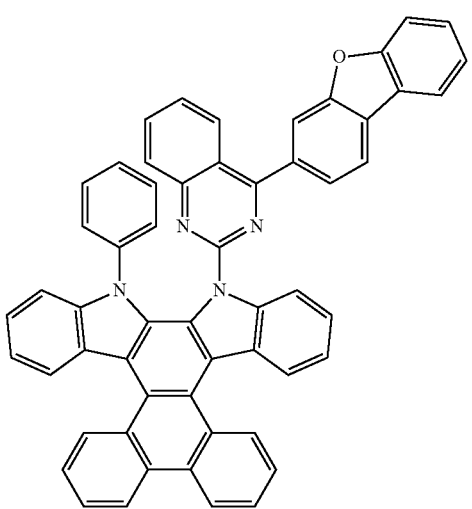

147
-continued
47
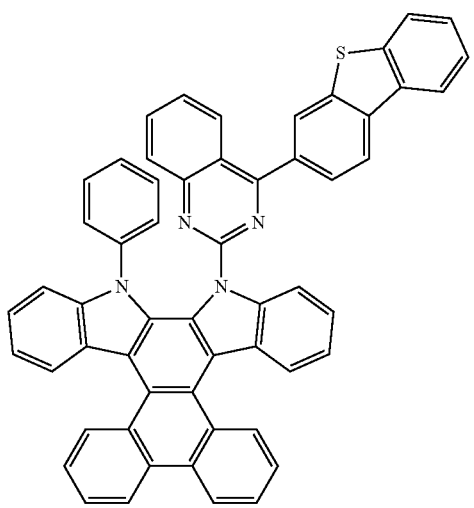
48
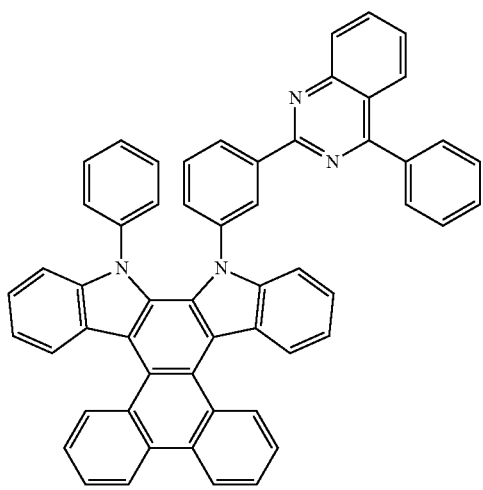
49
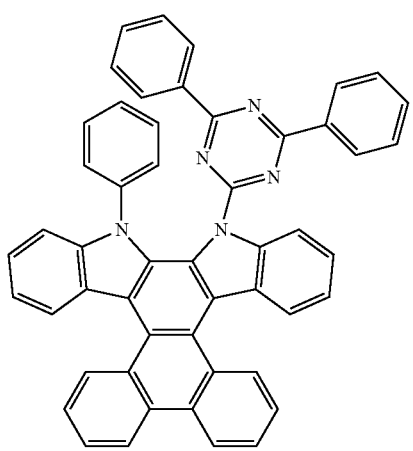
148
-continued
50
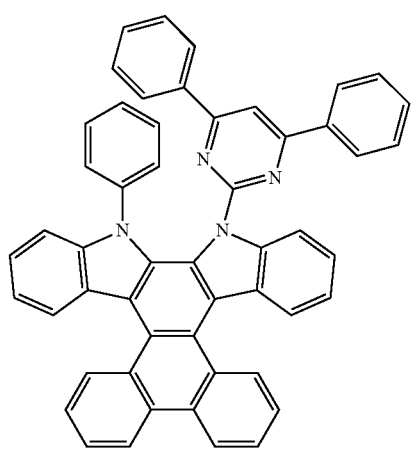
51
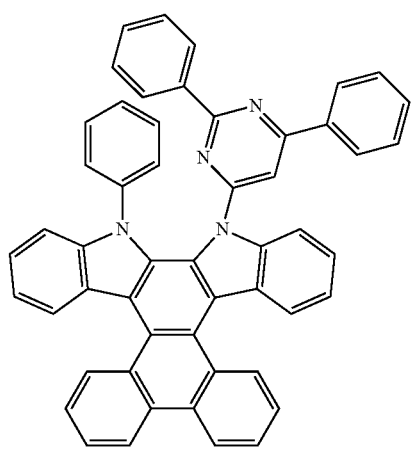
52
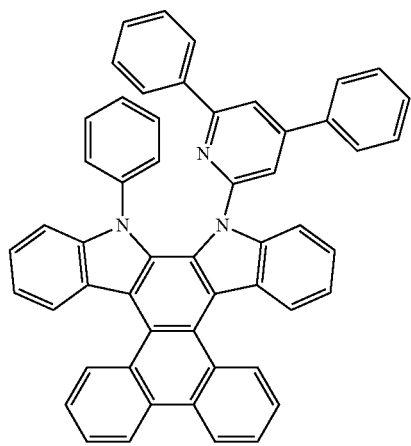

53
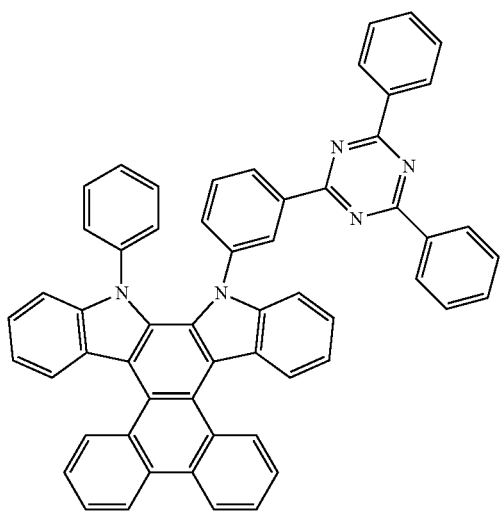
54
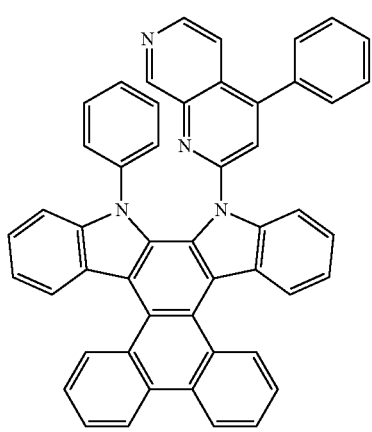
55
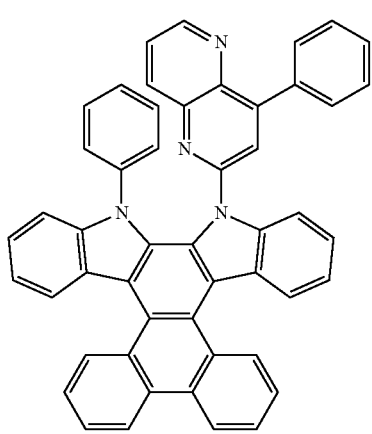
56
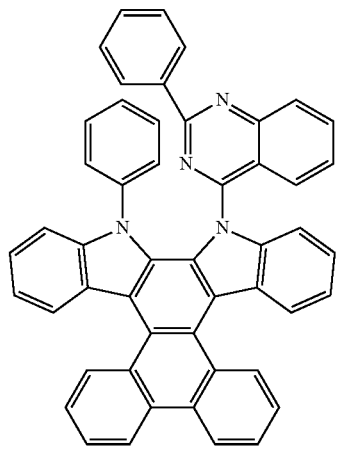
57
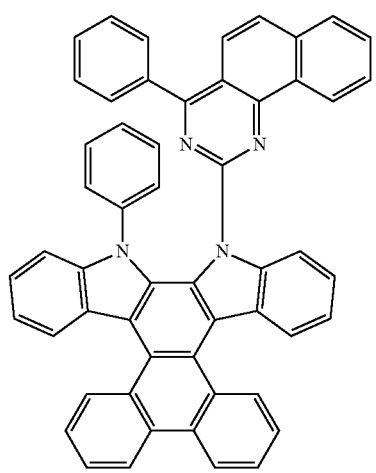
58
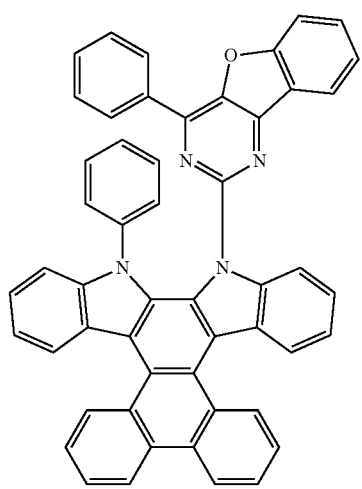

59
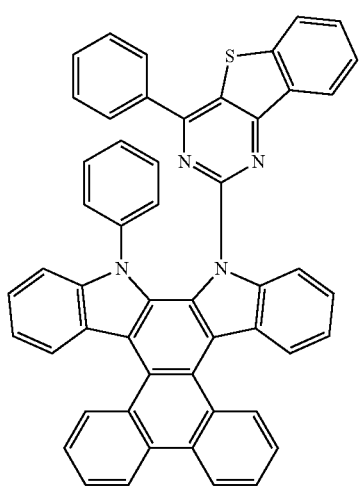
60
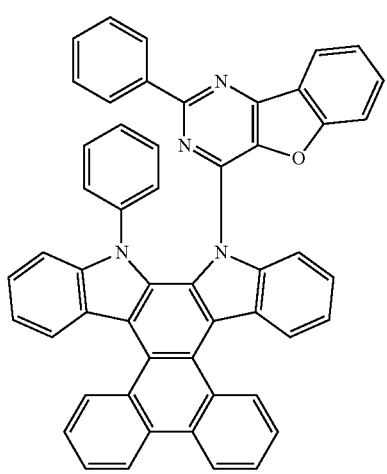
61
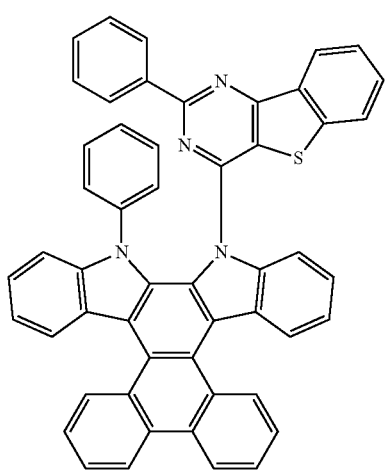
62
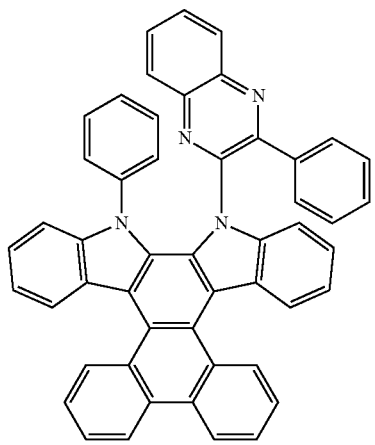
63
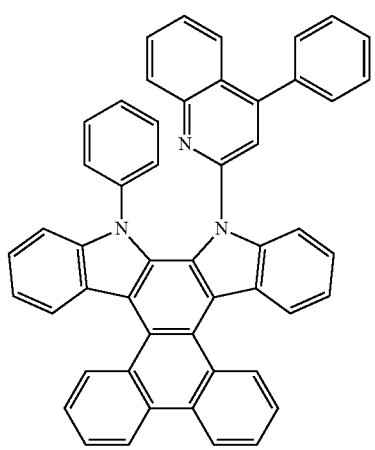
64
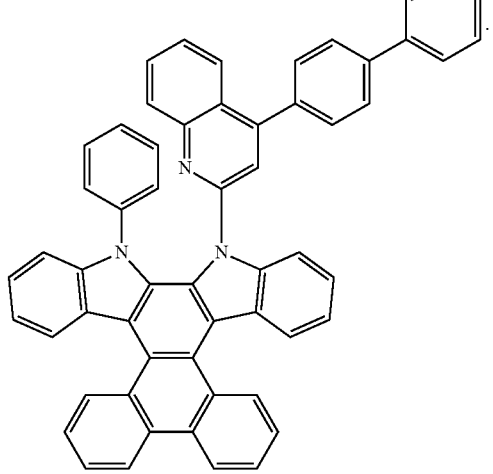
9. A composition for an organic optoelectric device, comprising:
  the compound for an organic optoelectric device as claimed in claim 3 as a first compound; and
  a compound represented by Chemical Formula 1B as a second compound,

[Chemical Formula 1B]

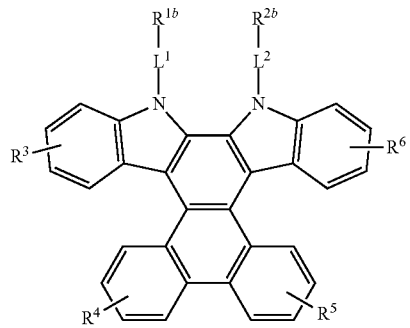

[Chemical Formula 2]

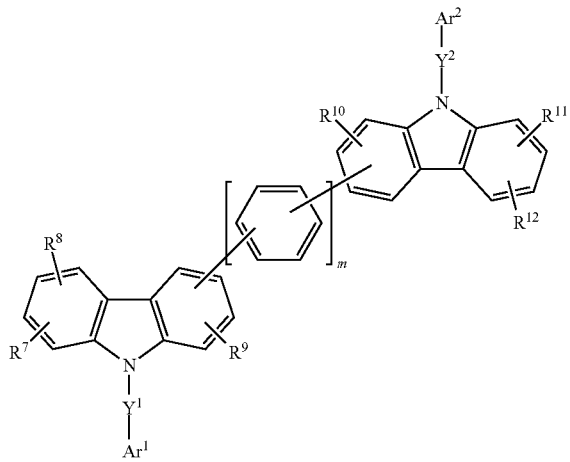

wherein, in Chemical Formula 1B $R^{1b}$ and $R^{2b}$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, a substituted or unsubstituted fluoranthenyl group, a substituted or unsubstituted carbazolyl group, a substituted or unsubstituted dibenzofuranyl group, a substituted or unsubstituted dibenzothiophenyl group, a substituted or unsubstituted benzonaphthofuranyl group, or a substituted or unsubstituted benzonaphthothiophenyl group, $R^3$ to $R^6$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and $L^1$ and $L^2$ are independently a single bond, a substituted or unsubstituted C6 to C30 arylene group, or a combination thereof.

10. A composition for an organic optoelectric device, comprising:

a first compound that is the compound for an organic optoelectric device as claimed in claim 1; and at least one second compound for an organic optoelectric device selected from a compound represented by Chemical Formula 2 and a compound consisting of a combination of a moiety represented by Chemical Formula 3 and a moiety represented by Chemical Formula 4:

wherein, in Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^1$ and $Ar^e$ are independently a substituted or unsubstituted C6 to C30 aryl group, a substituted or unsubstituted C2 to C30 heterocyclic group, or a combination thereof, $R^7$ to $R^{12}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and m is an integer of 0 to 2;

[Chemical Formula 3]

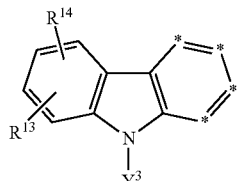

[Chemical Formula 4]

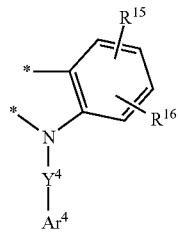

wherein, in Chemical Formulae 3 and 4, $Y^3$ and $Y^4$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^{13}$ to $R^{16}$ are independently hydrogen, deuterium, a substituted or unsubstituted C1 to C20 alkyl group, a substituted or unsubstituted C6 to C50 aryl group, a substituted or unsubstituted C2 to C50 heterocyclic group, or a combination thereof, two adjacent *'s of Chemical Formula 3 are C bound to two adjacent *'s of Chemical Formula 4 to provide a fused ring and *'s of not providing the fused ring in Chemical Formula 3 are independently $CR^a$, and $R^a$ is hydrogen, deuterium, a substituted or unsubstituted C1 to C10 alkyl group, a substituted or unsubstituted C6 to C12 aryl group, a substituted or unsubstituted C2 to C12 heterocyclic group, or a combination thereof;

wherein the "substituted" refers to replacement of at least one hydrogen by deuterium, a C1 to C4 alkyl group, a C6 to C18 aryl group, or a C2 to C18 heteroaryl group.

11. The composition for an organic optoelectric device as claimed in claim 10, wherein $Ar^1$ and $Ar^2$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

12. The composition for an organic optoelectric device as claimed in claim 10, wherein:

Chemical Formula 2 includes one of structures of Group III, and the moieties *—$Y^1$—$Ar^1$ and *—$Y^2$—$Ar^2$ of Chemical Formula 2 are independently one of substituents of Group IV,

[Group III]

C-1

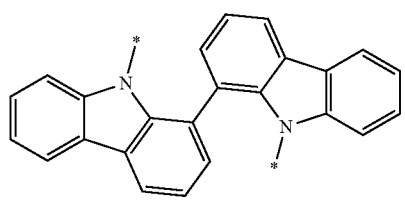

C-2

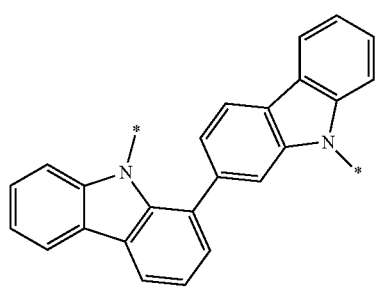

C-3

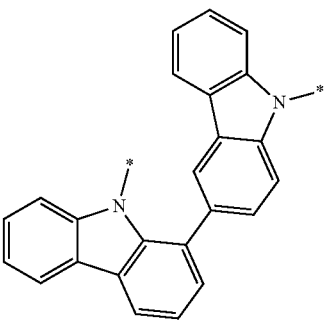

C-4

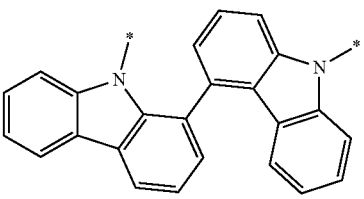

C-5

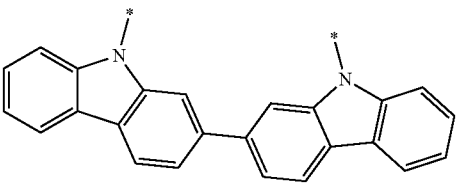

C-6

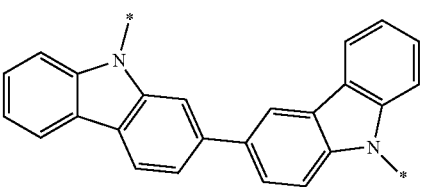

C-7

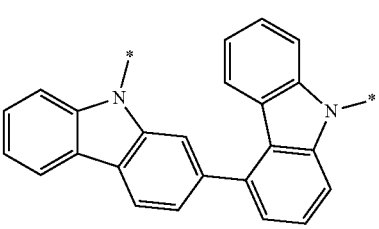

C-8

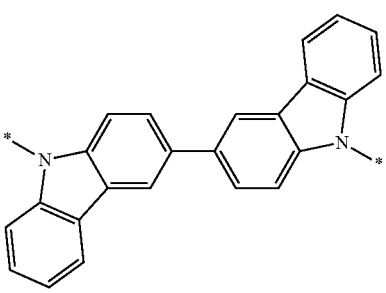

C-9

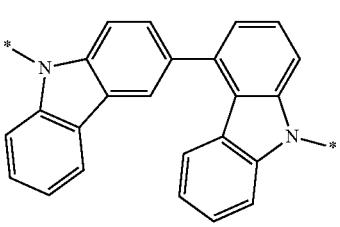

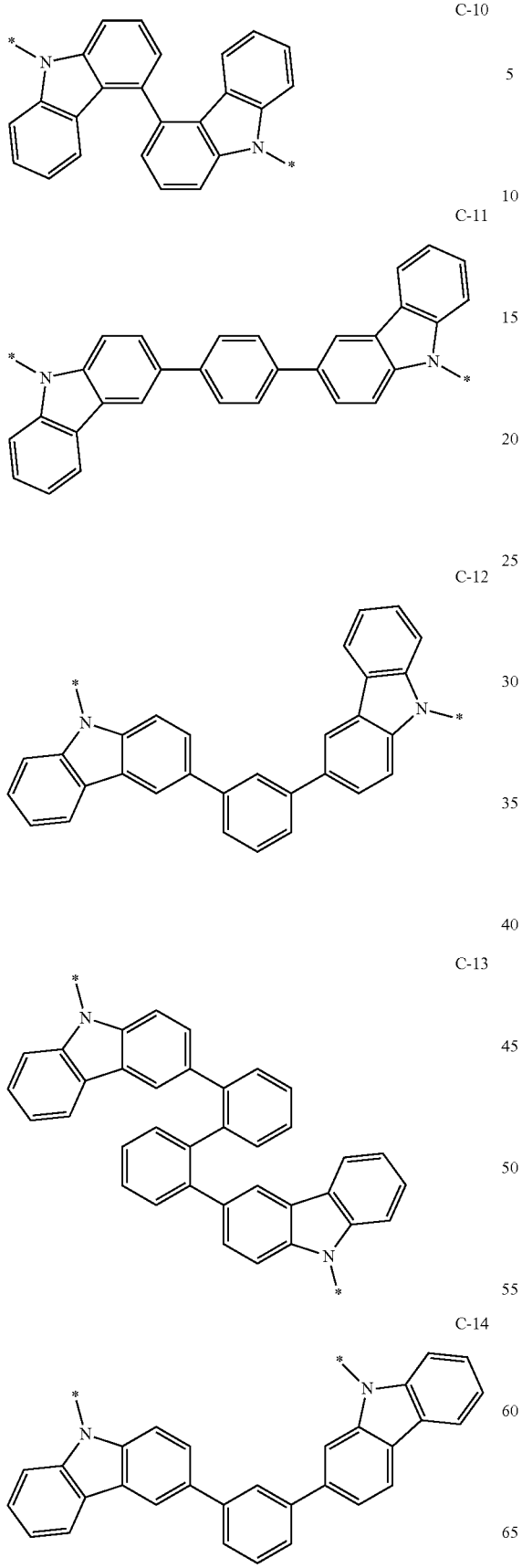
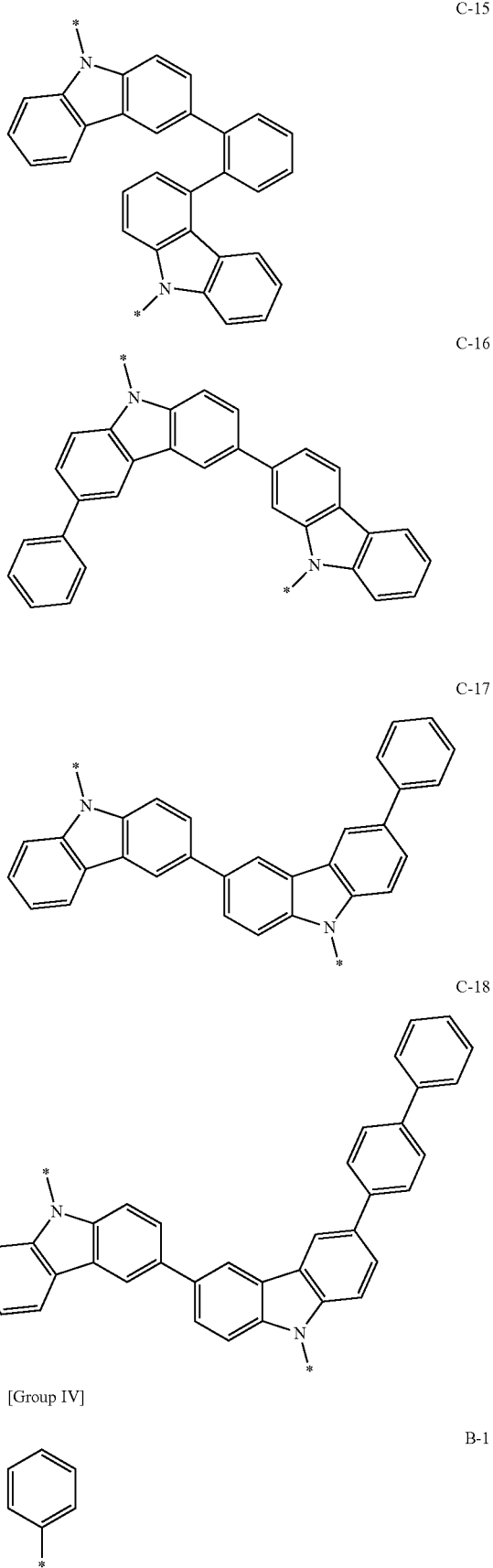

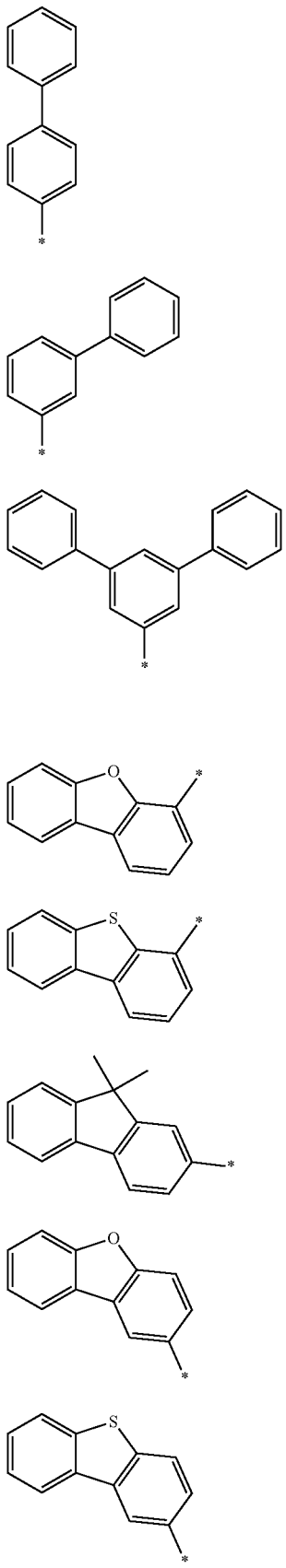

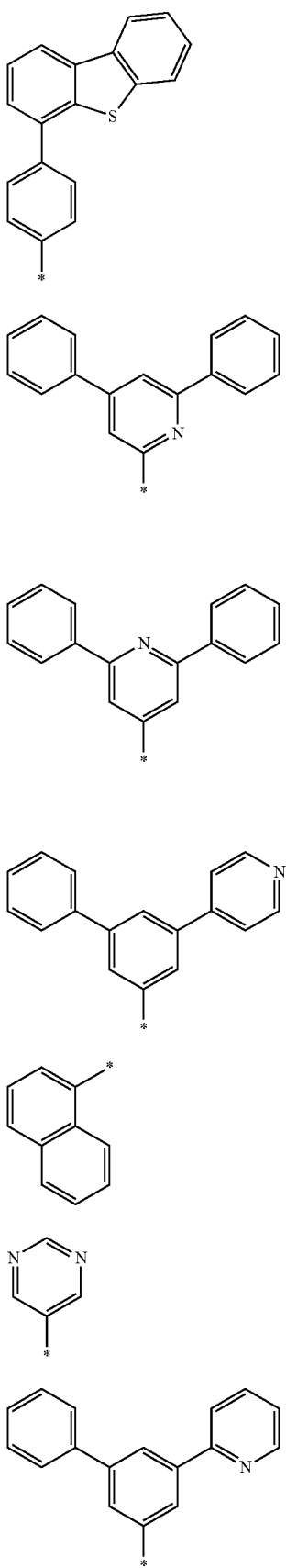

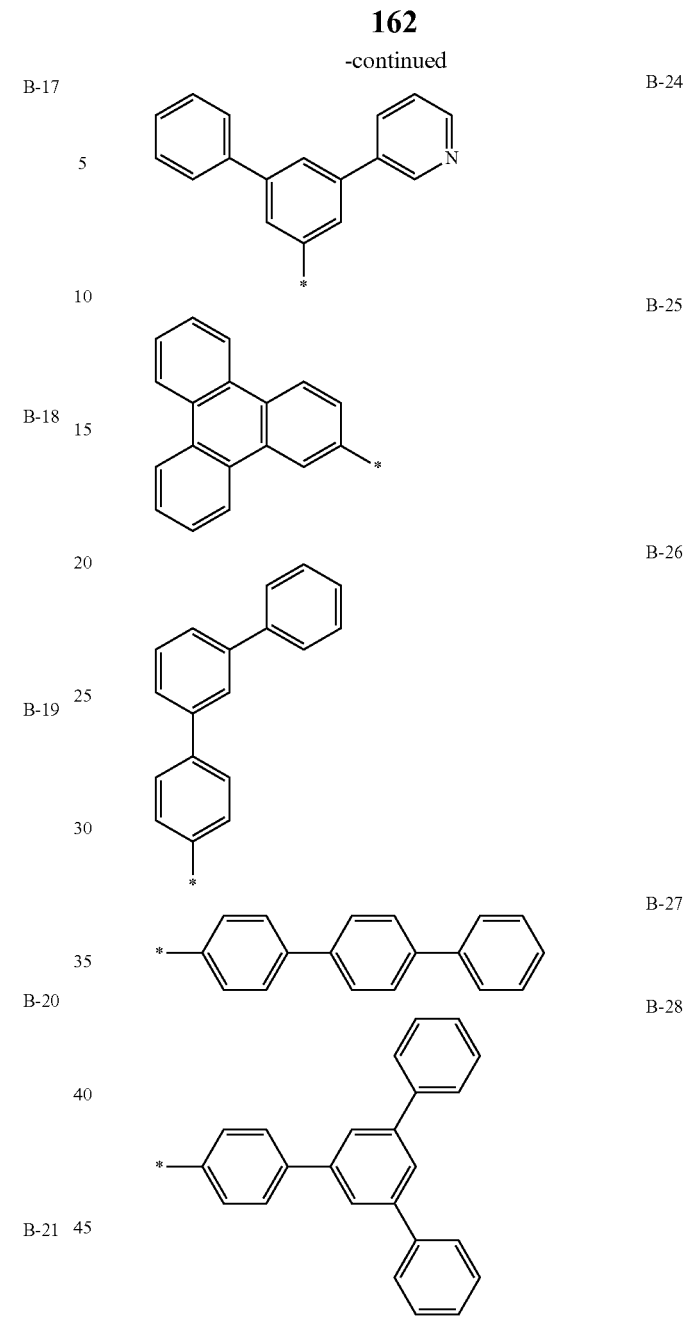

wherein, in Group III and Group IV, * is a linking point.

13. An organic optoelectric device, comprising:
an anode and a cathode facing each other, and
an organic layer between the anode and the cathode,
wherein the organic layer includes the compound for an organic optoelectric device as claimed in claim 1.

14. The organic optoelectric device of claim 13, wherein:
the organic layer includes a light emitting layer, and
the compound for an organic optoelectric device is included as a host of the light emitting layer.

15. The organic optoelectric device as claimed in claim 14, wherein:
the organic layer further includes a hole transport auxiliary layer adjacent to the light emitting layer, and
the hole transport auxiliary layer includes the compound for an organic optoelectric device.

16. An organic optoelectric device, comprising:
an anode and a cathode facing each other, and
an organic layer between the anode and the cathode,
wherein the organic layer includes the composition for an organic optoelectric device of claim 9.

17. The organic optoelectric device of claim 16, wherein:
the organic layer includes a light emitting layer, and
the composition for an organic optoelectric device is included as a host of the light emitting layer.

18. The organic optoelectric device as claimed in claim 17, wherein:
the organic layer further includes a hole transport auxiliary layer adjacent to the light emitting layer, and
the hole transport auxiliary layer includes the composition for an organic optoelectric device.

19. An organic optoelectric device, comprising:
an anode and a cathode facing each other, and
an organic layer between the anode and the cathode,
wherein the organic layer includes the composition for an organic optoelectric device of claim 10.

20. The organic optoelectric device of claim 19, wherein:
the organic layer includes a light emitting layer, and
the composition for an organic optoelectric device is included as a host of the light emitting layer.

21. The organic optoelectric device as claimed in claim 20, wherein:
the organic layer further includes a hole transport auxiliary layer adjacent to the light emitting layer, and
the hole transport auxiliary layer includes the composition for an organic optoelectric device.

* * * * *